United States Patent
Doppalapudi et al.

(10) Patent No.: US 12,365,704 B2
(45) Date of Patent: Jul. 22, 2025

(54) NUCLEIC ACID-POLYPEPTIDE COMPOSITIONS AND USES THEREOF

(71) Applicant: Avidity Biosciences, Inc., San Diego, CA (US)

(72) Inventors: Venkata Ramana Doppalapudi, La Jolla, CA (US); Michael Caramian Cochran, La Jolla, CA (US); David Sai-Ho Chu, La Jolla, CA (US); Joel Daniel Arias, La Jolla, CA (US); Rob Burke, La Jolla, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 209 days.

(21) Appl. No.: 18/067,975

(22) Filed: Dec. 19, 2022

(65) Prior Publication Data

US 2023/0234978 A1    Jul. 27, 2023

Related U.S. Application Data

(63) Continuation of application No. 16/894,589, filed on Jun. 5, 2020, now Pat. No. 11,578,090.

(60) Provisional application No. 62/858,285, filed on Jun. 6, 2019.

(51) Int. Cl.
| | | |
|---|---|---|
| C07F 9/40 | (2006.01) | |
| C07F 9/6512 | (2006.01) | |
| C07F 9/6558 | (2006.01) | |
| C12N 15/113 | (2010.01) | |

(52) U.S. Cl.
CPC .......... *C07F 9/4006* (2013.01); *C07F 9/6512* (2013.01); *C07F 9/65583* (2013.01); *C12N 15/113* (2013.01); *C12N 2310/14* (2013.01); *C12N 2310/351* (2013.01); *C12N 2310/3513* (2013.01)

(58) Field of Classification Search
None
See application file for complete search history.

(56) References Cited

U.S. PATENT DOCUMENTS

| | | |
|---|---|---|
| 5,142,047 A | 8/1992 | Summerton et al. |
| 5,185,444 A | 2/1993 | Summerton et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,821,783 B1 | 11/2004 | Comely et al. |
| 6,884,869 B2 | 4/2005 | Senter et al. |
| 7,498,298 B2 | 3/2009 | Doronina et al. |
| 7,850,975 B2 | 12/2010 | Mullis |
| 7,943,762 B2 | 5/2011 | Weller et al. |
| 8,288,352 B2 | 10/2012 | Doronina et al. |
| 8,501,930 B2 | 8/2013 | Rozema et al. |
| 8,591,910 B2 | 11/2013 | Mullis |
| 8,604,184 B2 | 12/2013 | Mullis et al. |
| 8,609,105 B2 | 12/2013 | Senter et al. |
| 8,697,688 B2 | 4/2014 | Howard et al. |
| 8,927,513 B2 | 1/2015 | Manoharan et al. |
| 8,936,910 B2 | 1/2015 | Mitsch et al. |
| 9,089,614 B2 | 7/2015 | Lin et al. |
| 9,127,033 B2 | 9/2015 | Prakash et al. |
| 9,481,905 B2 | 11/2016 | Chen et al. |
| 9,725,474 B2 | 8/2017 | Murata et al. |
| 9,809,817 B2 | 11/2017 | Khvorova et al. |
| 10,881,743 B2 | 1/2021 | Geall et al. |
| 11,084,844 B2 | 8/2021 | Prakash et al. |
| 11,110,180 B2 | 9/2021 | Geall et al. |
| 11,208,429 B2 | 12/2021 | Takahashi et al. |
| 11,364,302 B1 | 6/2022 | Geall et al. |
| 11,578,090 B2 | 2/2023 | Doppalapudi et al. |
| 12,006,499 B2 | 6/2024 | Doppalapudi et al. |
| 2004/0012626 A1 | 1/2004 | Brookins |
| 2007/0004665 A1 | 1/2007 | McSwiggen et al. |
| 2011/0293512 A1 | 12/2011 | Violette et al. |
| 2012/0065169 A1 | 3/2012 | Hanson et al. |
| 2012/0157511 A1 | 6/2012 | Manoharan et al. |
| 2013/0028919 A1 | 1/2013 | Howard et al. |
| 2013/0116420 A1 | 5/2013 | Prakash et al. |
| 2013/0309256 A1 | 11/2013 | Lyon et al. |
| 2013/0323836 A1 | 12/2013 | Manoharan et al. |
| 2014/0127239 A1 | 5/2014 | Howard |
| 2014/0194610 A1 | 7/2014 | Verdine et al. |

(Continued)

FOREIGN PATENT DOCUMENTS

| | | |
|---|---|---|
| CN | 109526222 A | 3/2019 |
| EP | 0532423 A1 | 3/1993 |

(Continued)

OTHER PUBLICATIONS

Habus et al. Oligonucleotides containing acyclic nucleoside analogues with carbamate internucleoside linkages. Nucleosides, Nucleotides & Nucleic Acids 14(9-10):1853-1859 (1995).

Karlsen et al. Pyrene-modified unlocked nucleic acids: synthesis, thermodynamic studies, and fluorescent properties. Chembiochem 13(4):590-601 (2012).

Karlsen et al. Synthesis of an unlocked nucleic acid terpyridine monomer and binding of divalent metal ion in nucleic acid duplexes. J Org Chem 74(22):8838-8841 (2009).

Prakash et al. Identification of metabolically stable 5'-phosphate analogs that support single-stranded siRNA activity. Nucleic Acids Res. 43(6):2993-3011 (2015).

(Continued)

*Primary Examiner* — Brian J Davis
(74) *Attorney, Agent, or Firm* — WILSON SONSINI GOODRICH & ROSATI

(57) ABSTRACT

Disclosed herein are compositions and pharmaceutical formulations that comprise a binding moiety conjugated to a modified polynucleic acid molecule and a polymer. Also described herein include methods for treating a cancer which utilize a composition or a pharmaceutical formulation comprising a binding moiety conjugated to a polynucleic acid molecule and a polymer.

13 Claims, 15 Drawing Sheets

Specification includes a Sequence Listing.

(56) References Cited

U.S. PATENT DOCUMENTS

| | | |
|---|---|---|
| 2014/0286970 A1 | 9/2014 | Jeffrey et al. |
| 2014/0294851 A1 | 10/2014 | Nguyen |
| 2014/0296321 A1 | 10/2014 | Iversen |
| 2015/0037360 A1 | 2/2015 | Smith |
| 2015/0064181 A1 | 3/2015 | Armstrong |
| 2015/0080457 A1 | 3/2015 | Manoharan et al. |
| 2015/0105539 A1 | 4/2015 | Miao et al. |
| 2015/0105540 A1 | 4/2015 | Miao et al. |
| 2015/0211006 A1 | 7/2015 | Butler et al. |
| 2016/0016983 A1 | 1/2016 | Murata et al. |
| 2016/0046939 A1 | 2/2016 | Prakash et al. |
| 2016/0186185 A1 | 6/2016 | Prakash et al. |
| 2016/0376577 A1 | 12/2016 | Madison et al. |
| 2017/0035796 A1 | 2/2017 | Wooddell et al. |
| 2017/0051286 A1 | 2/2017 | Smith |
| 2017/0081425 A1 | 3/2017 | Colletti et al. |
| 2017/0281795 A1 | 10/2017 | Geall et al. |
| 2019/0240346 A1 | 8/2019 | Sugo et al. |
| 2020/0385725 A1 | 12/2020 | Doppalapudi et al. |
| 2021/0095283 A1 | 4/2021 | Geall et al. |
| 2022/0395580 A1 | 12/2022 | Geall et al. |
| 2022/0395589 A1 | 12/2022 | Geall et al. |
| 2024/0301419 A1 | 9/2024 | Doppalapudi et al. |

FOREIGN PATENT DOCUMENTS

| | | | |
|---|---|---|---|
| EP | 1579015 A2 | 9/2005 | |
| EP | 1068241 B1 | 10/2007 | |
| EP | 2344637 B1 | 12/2014 | |
| EP | 2421971 B1 | 7/2016 | |
| EP | 2486141 B1 | 1/2018 | |
| JP | 2005504020 A | 2/2005 | |
| JP | 2005508634 A | 4/2005 | |
| JP | 2018529732 A | 10/2018 | |
| KR | 20130105294 A | 9/2013 | |
| WO | WO-9207065 A1 | 4/1992 | |
| WO | WO-9315187 A1 | 8/1993 | |
| WO | WO-9734631 A1 | 9/1997 | |
| WO | WO-9813526 A1 | 4/1998 | |
| WO | WO-03004602 A2 | 1/2003 | |
| WO | WO-03037909 A1 | 5/2003 | |
| WO | WO-2008036127 A2 | 3/2008 | |
| WO | WO-2008147824 A2 | 12/2008 | |
| WO | WO-2009061941 A2 | 5/2009 | |
| WO | WO-2009099942 A2 | 8/2009 | |
| WO | WO-2009126933 A2 | 10/2009 | |
| WO | WO-2011005860 A2 | 1/2011 | |
| WO | WO-2011139699 A2 | 11/2011 | |
| WO | WO-2011139702 A2 | 11/2011 | |
| WO | WO-2011150408 A2 | 12/2011 | |
| WO | WO-2012031243 A2 | 3/2012 | |
| WO | WO-2013166155 A1 | 11/2013 | |
| WO | WO-2014080251 A1 | 5/2014 | |
| WO | WO-2014100505 A1 | 6/2014 | |
| WO | WO-2014140317 A2 | 9/2014 | |
| WO | WO-2014145090 A1 | 9/2014 | |
| WO | WO-2014177042 A1 | 11/2014 | |
| WO | WO-2014197854 A1 | 12/2014 | |
| WO | WO-2015038426 A1 | 3/2015 | |
| WO | WO-2015057699 A2 | 4/2015 | |
| WO | WO-2015069587 A2 | 5/2015 | |
| WO | WO-2015107425 A2 | 7/2015 | |
| WO | WO-2016028649 A1 | 2/2016 | |
| WO | WO-2016187425 A1 | 11/2016 | |
| WO | WO-2017059223 A2 | 4/2017 | |
| WO | WO-2017148879 A1 | 9/2017 | |
| WO | WO-2017173304 A1 | 10/2017 | |
| WO | WO-2017173408 A1 | 10/2017 | |
| WO | WO 2017/214112 A1 * | 12/2017 | ............ C07H 21/02 |
| WO | WO-2017221883 A1 | 12/2017 | |
| WO | WO-2018045317 A1 | 3/2018 | |
| WO | WO-2018129384 A1 | 7/2018 | |
| WO | WO-2019071028 A1 | 4/2019 | |
| WO | WO-2019136180 A2 | 7/2019 | |
| WO | WO-2020247782 A1 | 12/2020 | |
| WO | WO-2020247818 A1 | 12/2020 | |

OTHER PUBLICATIONS

U.S. Appl. No. 16/894,648 Office Action dated Jul. 3, 2023.
U.S. Appl. No. 17/364,765 Office Action dated May 17, 2023.
U.S. Appl. No. 17/364,765 Office Action dated Oct. 23, 2023.
Vaish et al. Improved specificity of gene silencing by siRNAs containing unlocked nucleobase analogs. Nucleic Acids Res 39(5):1823-1832 (2011).
Watts et al. Chemically modified siRNA: tools and applications. Drug Discov Today 13(19-20):842-855 (2008).
U.S. Appl. No. 17/364,765 Office Action dated May 20, 2024.
U.S. Appl. No. 17/364,765 Office Action dated Sep. 19, 2024.
Abramova et al. Novel oligonucleotide analogues based on morpholino nucleoside subunits-antisense technologies: new chemical possibilities. Indian Journal of Chemistry 48B:1721-1726 (2009).
Agarwal et al. A Pictet-Spengler ligation for protein chemical modification. PNAS 110(1):46-51 (2013).
Albarran et al. Efficient intracellular delivery of a pro-apoptotic peptide with a pH-responsive carrier. React Funct Polym 71:261-265 (2011).
Augustyns et al., Incorporation of hexose nucleoside analogues into oligonucleotides: synthesis, base-pairing properties and enzymatic stability. Nucleic Acids Research 20(18):4711-4716 (1992).
Axup et al. Synthesis of site-specific antibody-drug conjugates using unnatural amino acids. PNAS 109(40):16101-16106 (2012).
Bell et al. Epidermal Growth Factor Receptor Mutations and Gene Amplification in Non-Small-Cell Lung Cancer: Molecular Analysis of the IDEAL/INTACT Gefitinib Trials. J Clin Oncol 23(31):8081-8092 (2005).
Berge et al. Pharmaceutical Salts. Journal of Pharmaceutical Sciences 66(1):1-19 (Jan. 1977).
Bird et al. Single-chain antigen-binding proteins. Science 242:423-442 (1988).
Blaney et al. Traceless solid-phase organic synthesis. Chem. Rev. 102:2607-2024 (2002.
Bulmus et al. A new pH-responsive and glutathione-reactive, endosomal membrane-disruptive polymeric carrier for intracellular delivery of biomolecular drugs. J Controlled Release 93:105-120 (2003).
Burke et al. siRNA-mediated knockdown of P450 oxidoreductase in rats: a tool to reduce metabolism by CYPs and increase exposure of high clearance compounds. Pharm. Res. 31(12):3445-3460 (2014).
Casi et al. Site-specific traceless coupling of potent cytotoxic drugs to recombinant antibodies for pharmacodelivery. J Am Chem Soc 134(13):5887-5892 (2012).
Castaneda et al. Acid-cleavable thiomaleamic acid linker for homogeneous antibody-drug conjugation, Chem. Commun. 49:8187-8189 (2013).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Collis, AEC. The synthesis of vinylphosphonate-linked RNA. [Ph. D. Thesis] Retrieved from http://eprints.nottingham.ac.uk/10541/1/Alana_Collis_Thesis.pdf (2008).
Crouse et al. Expression and amplification of engineered mouse dihydrofolate reductase minigenes. Mol Cell Biol 3(2):257-266 (1983).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).

(56) References Cited

OTHER PUBLICATIONS

Debacker et al. Improving gene silencing oligonucleotides by incorporation of peptide nucleic acids. Thesis (Doctoral) (Sep. 1, 2017) Retrieved from the Internet: URL:https://eprints.soton.ac.uk/422159/ [retrieved on Jul. 26, 2021].
Dimasi et al. Development of a trispecific antibody designed to simultaneously and efficiently target three different antigens on tumor cells. Mol Pharm 12(9):3490-3501 (2015).
Donner et al. Co-administration of an excipient oligonucleotide helps delineate pathways of productive and nonproductive uptake of phosphorothioate antisense oligonucleotides in the liver. Nucleic Acid Therapeutics 27(4): 209-220 (2017).
Duncan et al. A polymer-Triton X-100 conjugate capable of pH-dependent red blood cell lysis: a model system illustrating the possibility of drug delivery within acidic intracellular compartments. J Drug Target 2:341-347 (1994).
Elkayam et al., siRNA carrying an (E)-vinylphosphonate moiety at the 5' end of the guide strand augments gene silencing by enhanced binding to human Argonaute-2. Nucleic Acids Research 45(6):3528-3536 (2017).
El-Sayed et al. Rational design of composition and activity correlations for pH-responsive and glutathione-reactive polymer therapeutics. J Control Release 104:417-427 (2005).
Flanary et al. Antigen delivery with poly(propylacrylic acid) conjugation enhanced MHC-1 presentation and T-cell activation. Bioconjugate Chem. 20:241-248 (2009).
Goldspiel et al. Human gene therapy. Clin Pharm 12:488-505 (1993).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Haraszti et al. 5'-Vinylphosphonate improves tissue accumulation and efficacy of conjugated siRNAs in vivo. Nucleic Acids Res. 45(13):7581-7592 (2017).
Haringsma et al. mRNA knockdown by single strand RNA is improved by chemical modifications. Nucleic Acids Res 40(9):4125-4136 (2012).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85:5879-5883 (1988).
Jones et al. Poly(2-alkylacrylic acid) polymers deliver molecules to the cytosol by pH-sensitive disruption of endosomal vesicles. Biochem J 372:65-75 (2003).
Kang et al. HER2 RNA Aptamer- and Cell Penetrating Peptide-Mediated Delivery of Multimeric Antisense Strands of siRNAs for Gene Silencing: Multimeric antisense strands of siRNAs. Bull. Korean Chem. Soc. 37(9):1440-1444 (2016).
Khormaee et al. Endosomolytic anionic polymer for the cytoplasmic delivery of siRNAs in localized in vivo applications. Adv Funct Mater 23:565-574 (2013).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kozbor et al. The production of monoclonal antibodies from human lymphocytes. Immunology Today 4:72-79 (1983).

Kumar et al. 5'-Morpholino modification of the sense strand of an siRNA makes it a more effective passenger. Chemical Comm 55(35):5139-5142 (2019) Retrieved from the Internet: URL:https://pubs.rsc.org/en/content/articlepdf/2019/cc/c9cc00977a.
Kutmeier et al. Assembly of humanized antibody genes from synthetic oligonucleotides using a single-round PCR. BioTechniques 17:242 (1994).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
McEnaney et al. Antibody-recruiting molecules: an emerging paradigm for engaging immune function in treating human disease. ACS Chem Biol. 7(7):1139-1151 (2012).
Miller et al., Stabilin-mediated cellular internalization of phosphorothioate-modified antisense oligonucleotides (ASOs). https://digitalcommons.unl.edu/cgi/viewcontent.cgi?filename=0&article=1019&context=ucareresearch (2016).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science. 260(5110):926-932 (1993).
Naisbitt et al. Disposition of amodiaquine and related antimalarial agents in human neutrophils: implications for drug design. J Pharmacol Exp Ther 280:884-893 (1997).
Neuberger et al. Recombinant antibodies possessing novel effector functions. Nature 312(5995):604-608 (1984).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
Parmar et al. 5'-(E)-Vinylphosphonate: A Stable Phosphate Mimic Can Improve the RNAi Activity of siRNA-GalNAc Conjugates. Chembiochem 17(11):985-989 (2016).
PCT/US2018/054444 International Search Report and Written Opinion dated Feb. 15, 2019.
PCT/US2019/012223 International Search Report and Written Opinion dated Jul. 5, 2019.
PCT/US2020/036369 International Search Report and Written Opinion dated Oct. 20, 2020.
PCT/US2020/036420 International Search Report and Written Opinion dated Oct. 5, 2020.
Pei et al. Quantitative evaluation of siRNA delivery in vivo. RNA 16:2553-2563 (2010).
Prakash et al. Synergistic effect of phosphorothioate, 5'-vinylphosphonate and GalNAc modifications for enhancing activity of synthetic siRNA. Bioorg Med Chem Lett 26(12):2817-2820 (2016).
Pubchem CID 89552245. Feb. 13, 2015, pp. 1-10. Retrieved from the Internet <url: https://pubchem.ncbi.nlm.nih.gov/compound/89552245</url:.
Santerre et al. Expression of prokaryotic genes for hygromycin B and G418 resistance as dominant-selection markers in mouse L cells. Gene 30(1-3):147-156 (1984).
Shukla et al. Exploring Chemical Modifications for siRNA Therapeutics: A Structural and Functional Outlook. ChemMedChem 5(3):328-349 (2010).
Skerra et al. Assembly of a functional Immunoglobulin Fv fragment in *Escherichia coli*. Science 240(4855):1038-1041 (1988).
Strop et al. Location matters: site of conjugation modulates stability and pharmacokinetics of antibody drug conjugates. Chem Biol 20(2):161-167 (2013).
Suriano et al. Beta-catenin (CTNNB1) gene amplification: a new mechanism of protein overexpression in cancer. Genes Chromosomes Cancer 42(3):238-246 (2005).

(56) References Cited

OTHER PUBLICATIONS

Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Talasila et al. EGFR Wild-type Amplification and Activation Promote Invasion and Development of Glioblastoma Independent of Angiogenesis. Acta Neuropathol. 125(5):683-698 (2013).
Tolstoshev. Gene Therapy, Concepts, Current Trials and Future Directions. Ann. Rev. Pharmacol. Toxicol. 32:573-596 (1993).
U.S. Appl. No. 16/152,324 Office Action dated Oct. 16, 2020.
U.S. Appl. No. 16/894,589 Office Action dated Feb. 9, 2022.
U.S. Appl. No. 16/894,589 Office Action dated Jul. 18, 2022.
U.S. Appl. No. 17/364,754 Office Action dated Oct. 29, 2021.
Valtorta et al. KRAS gene amplification in colorectal cancer and impact on response to EGFR-targeted therapy. Int J Cancer 133:1259-1266 (2013).
Walker et al. Improved cellular delivery of antisense oligonucleotides using transferrin receptor antibody-oligonucleotide conjugates. Pharmaceutical research 12(10):1548-1553 (1995).
Ward et al. Binding activities of a repertoire of single immunoglobulin variable domains secreted from *Escherichia coli*. Nature 341(6242):544-546 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wu et al. Building complex glycopeptides: Development of a cysteine-free native chemical ligation protocol. Angew. Chem. Int. Ed. 45:4116-4125 (2006).
Wu et al. Delivery systems for gene therapy. Biotherapy 3:87-95 (1991).
Wu et al. Site-specific chemical modification of recombinant proteins produced in mammalian cells by using the genetically encoded aldehyde tag. PNAS USA 106(9):3000-3005 (2009).
Yessine et al. Characterization of the membrane-destabilizing properties of different pH-sensitive methacrylic acid copolymers. Biochimica et Biophysica Acta 1613:28-38 (2003).
Zhang et al. A remote arene-binding site on prostate specific membrane antigen revealed by antibody-recruiting small molecules. J Am Chem Soc. 132(36):12711-12716 (2010).
Zhang et al. RNA interference in mammalian cells by siRNAs modified with morpholino nucleoside analogues. Bioorg Med Chem 17(6):2441-2446 (2009).

\* cited by examiner

NUCLEIC ACID-POLYPEPTIDE COMPOSITIONS AND USES THEREOF

CROSS-REFERENCE

This application is a continuation of U.S. patent application Ser. No. 16/894,589, filed Jun. 5, 2020, which claims benefit of U.S. Provisional Patent Application No. 62/858,285 filed Jun. 6, 2019, each of which is incorporated herein by reference in its entirety.

SEQUENCE LISTING

The instant application contains a Sequence Listing which has been submitted electronically in XML format and is hereby incorporated by reference in its entirety. Said XML copy, created on Dec. 16, 2022, is named 45532-734_301_SL.xml and is 17,412,395 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

SUMMARY OF THE DISCLOSURE

Disclosed herein, in certain embodiments, are compositions and pharmaceutical formulations that comprise a binding moiety conjugated to a polynucleic acid molecule and optionally a polymer. In some embodiments, also described herein include methods for treating a disease or condition (e.g., cancer) that utilize a composition or a pharmaceutical formulation comprising a binding moiety conjugated to a polynucleic acid molecule and a polymer.

Disclosed herein, in certain embodiments, is a compound according to Formula (II):

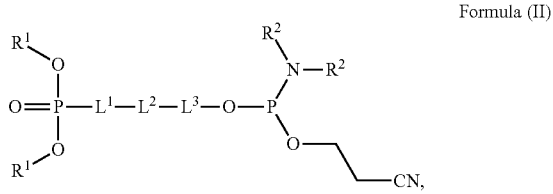

Formula (II)

wherein,
each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl;
each $R^2$ is independently hydrogen, deuterium, substituted or unsubstituted $C_1$-$C_6$ alkyl, or substituted or unsubstituted $C_1$-$C_6$ heteroalkyl;
or two $R^2$ are taken together with the nitrogen atom to which they are attached to form a substituted or unsubstituted $C_2$-$C_{10}$ heterocycloalkyl;
$L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;
$L^2$ is a bond, O, S, $NR^3$, substituted or unsubstituted $C_4$-$C_7$ cycloalkylene, substituted or unsubstituted $C_4$-$C_7$ heterocycloalkylene, substituted or unsubstituted $C_5$-$C_8$ arylene, or substituted or unsubstituted $C_4$-$C_8$ heteroarylene;
wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;
$L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene; and
wherein at least two of $L^1$, $L^2$ and $L^3$ are not a bond.

In some instances, L2 is a bond, O, S or NR3, substituted or unsubstituted C4-C7 cycloalkylene, substituted or unsubstituted C5-C8 arylene, phenylene, or cyclohexyl. In some instances, L1 is C1-C5 alkylene, C1-C3 alkenylene, or C1-C5 alkynylene, and L3 is C1-C5 alkylene, C1-C3 alkenylene, or C1-C5 alkynylene. In some instances, L1 is C1-C5 alkylene, and L3 is C1-C5 alkylene. In some embodiments, L2 is methylene, a bond, O, S or NR3.

In some instances, each R1 is independently substituted or unsubstituted $C_1$-$C_6$ alkyl. In some instances, each R2 is independently substituted or unsubstituted C1-$C_6$ alkyl, CH3, —CH2CH3, —CH2CH2CH3, or —CH2(CH3)2. In some instances, the compound is selected from the group consisting of:

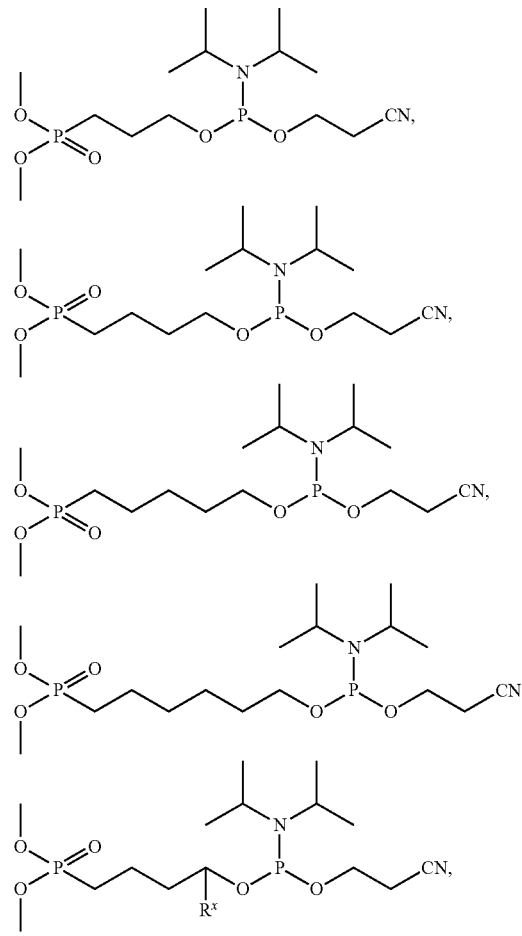

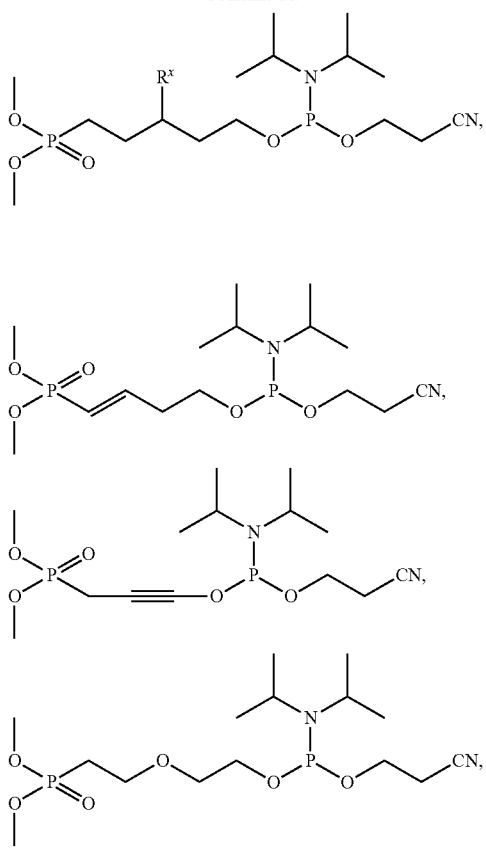

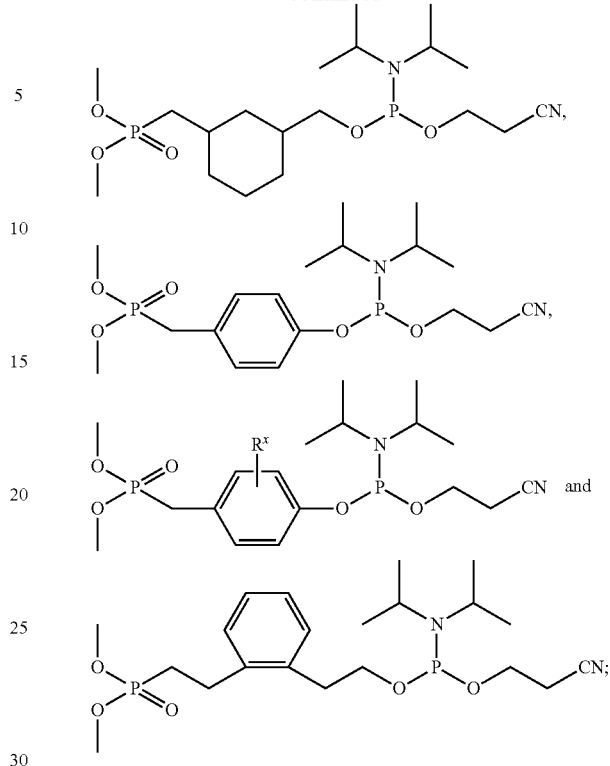

where $R^x$ is H, halogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, unsubstituted or substituted monocyclic heterocycle, —CN, —OH, —O-alkyl, —$CO_2H$, —$CO_2$-alkyl, —$CH_2CO_2H$, —$CH_2CO_2$-alkyl, —C(=O)$NH_2$, —C(=O)NH-alkyl, —$CH_2$C(=O)$NH_2$, —$CH_2$C(=O)NH-alkyl, $NH_2$, —NH-alkyl, —$CH_2NH_2$, —$CH_2$NH-alkyl, —NHC(=O)alkyl, —$CH_2$NHC(=O)alkyl. —SH, —S-alkyl, —S(=O)H, —S(=O)alkyl, —$SO_2H$, —$SO_2$-alkyl, —$SO_2NH_2$ or —$SO_2$NH-alkyl.

Also disclosed herein is an oligonucleotide comprising a compound of Formula (IIa) at one of the termini:

Formula (IIa)

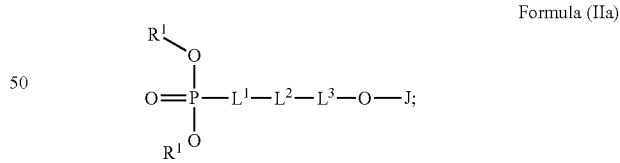

wherein each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl; $L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene; $L^2$ is a bond, O, S, $NR^3$, substituted or unsubstituted $C_4$-$C_7$ cycloalkylene, substituted or unsubstituted $C_4$-$C_6$ heterocycloalkylene, substituted or unsubstituted $C_5$-$C_8$ arylene, or substituted or unsubstituted $C_4$-$C_8$ heteroarylene; wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted

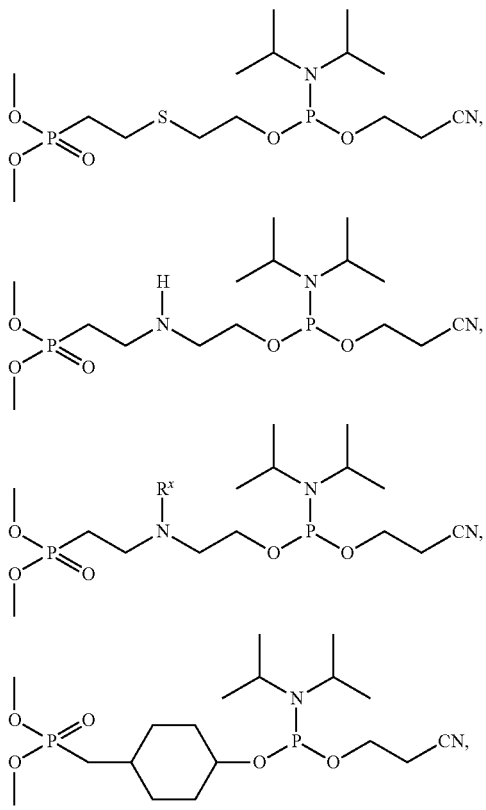

or substituted monocyclic carbocycle, and unsubstituted or substituted monocyclic heterocycle; $L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene; J is an internucleotide linking group linking to the adjacent nucleotide of the polynucleotide; and wherein at least two of $L^1$, $L^2$ and $L^3$ are not a bond.

In some instances, the oligonucleotide is an RNA oligonucleotide. In some instances, the oligonucleotide further comprises at least one modification, or at least one 2' modified nucleotide. In some embodiments, the oligonucleotide further comprises at least one 2' modified nucleotide selected from 2'-O-methyl, 2'-O-methoxyethyl (2'-O-MOE), 2'-deoxy, 2-deoxy-2'-fluoro, 2'-O-aminopropyl (2'-O-AP), 2'-O-dimethylaminoethyl (2'-O-DMAOE), 2'-O-dimethyl-aminopropyl (2'-O-DMAP), 2'-O-dimethylaminoethyloxy-ethyl (2'-O-DMAEOE), or 2'-O—N-methylacetamido (2'-O-NMA) modified nucleotide. In some embodiments, the oligonucleotide further comprises at least one 2' modified nucleotide selected from locked nucleic acid (LNA) or ethylene nucleic acid (ENA), at least one modified internucleotide linkage. In some embodiments, the oligonucleotide further comprises at least one modified internucleotide linkage selected from a phosphorothioate linkage, a phosphorodithioate linkage, a methylphosphonate linkage, a phosphotriester linkage or an amide linkage.

In some instances, the compound of Formula (IIa) is located at the 5'-terminus of the oligonucleotide. In some instances, the oligonucleotide is conjugated to a binding moiety. In some embodiments, the compound of Formula (IIa) is located at the 5'-terminus of the oligonucleotide, and the binding moiety is conjugated to the 3'-terminus of the oligonucleotide.

In some instances, the binding moiety comprises an antibody or a binding fragment thereof. In some embodiments, the antibody or the binding fragment thereof comprises a humanized antibody or binding fragment thereof, a chimeric antibody or binding fragment thereof, a monoclonal antibody or binding fragment thereof, a monovalent Fab', a divalent Fab2, a single-chain variable fragment (scFv), a diabody, a minibody, a nanobody, a single-domain antibody (sdAb), or a camelid antibody or binding fragment thereof. In some embodiments, the binding moiety comprises a peptide, an aptamer, or a small molecule.

In some instances, the oligonucleotide comprises from about 8 to about 50 nucleotides, or from about 10 to about 30 nucleotides.

In some instances, the oligonucleotide is an RNA oligonucleotide, is conjugated to a binding moiety, is from about 10 to about 30 nucleotides, comprises at least one 2' modified nucleotide, and comprises at least one modified internucleotide linkage. In some instances, the oligonucleotide hybridizes to at least 8 contiguous bases of a target gene sequence. In some instances, the oligonucleotide mediates RNA interference. In some embodiments, the oligonucleotide is a sense strand. In some embodiments, the oligonucleotide is hybridized with a second oligonucleotide to form a double-stranded oligonucleic acid molecule. In some embodiments, the second oligonucleotide is an antisense strand. In some embodiments, the second oligonucleotide is an RNA oligonucleotide. In some embodiments, the second oligonucleotide comprises at least one modification. In some embodiments, the second oligonucleotide comprises at least one 2' modified nucleotide. In some embodiments, the second oligonucleotide comprises at least one 2' modified nucleotide selected from 2'-O-methyl, 2'-O-methoxyethyl (2'-O-MOE), 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethyl-aminoethyloxyethyl (2'-O-DMAEOE), or 2'-O—N-methylacetamido (2'-O-NMA) modified nucleotide. In some embodiments, the second oligonucleotide comprises at least one 2' modified nucleotide selected from locked nucleic acid (LNA) or ethylene nucleic acid (ENA). In some embodiments, the second oligonucleotide comprises at least one modified internucleotide linkage. In some embodiments, wherein the second oligonucleotide comprises at least one modified internucleotide linkage selected from a phosphorothioate linkage, a phosphorodithioate linkage, a methylphosphonate linkage, a phosphotriester linkage or an amide linkage.

In some embodiments, the oligonucleotide comprises a polymer. In some embodiments, the oligonucleotide comprises polyethylene glycol.

In some embodiments, the oligonucleotide comprises a first strand and a second strand, wherein the first strand is a sense strand, is an RNA oligonucleotide, is conjugated to a binding moiety, a polymer, or a combination thereof, is from about 10 to about 30 nucleotides, comprises at least one 2' modified nucleotide, and comprises at least one modified internucleotide linkage; and the second strand is an antisense strand, an RNA oligonucleotide, is from about 10 to about 30 nucleotides, comprises at least one 2' modified nucleotide, and comprises at least one modified internucleotide linkage.

In another embodiment, disclosed herein is a an oligonucleotide conjugate of Formula (I):

A-B                                                                    Formula (I), wherein,
A is a binding moiety;
B is an oligonucleotide comprising a nucleotide compound of Formula (IIa), and

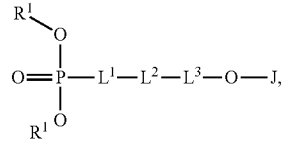

Formula (IIa)

wherein;
each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl;
$L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;
$L^2$ is a bond, O, S, $NR^3$, substituted or unsubstituted $C_4$-$C_7$ cycloalkylene, substituted or unsubstituted $C_4$-$C_7$ heterocycloalkylene, substituted or unsubstituted $C_5$-$C_8$ arylene, or substituted or unsubstituted $C_4$-$C_8$ heteroarylene;
wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;
$L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;

J is an internucleotide linking group linking to the adjacent nucleotide of the polynucleotide; and wherein at least two of $L^1$, $L^2$ and $L^3$ are not a bond.

In some instances, the oligonucleotide conjugate further comprises C to form a formula A-B-C          (Formula I-A)

Disclosed herein, in certain embodiments, is a method of inhibiting the expression of a target gene in a primary cell of a patient, comprising administering a molecule described above to the primary cell. In some embodiments, the method is an in vivo method. In some embodiments, the patient is a human. Also disclosed herein is a method of treating a subject having a disease or a condition characterized with a defective protein expression, comprising administering to the subject an oligonucleotide as described herein to modulate expression of a gene encoding the protein, thereby treating the disease or condition characterized with the defective protein expression. Also disclosed herein is a method of treating a subject having a disease or a condition characterized with a protein overexpression, comprising administering to the subject an oligonucleotide as described herein to modulate expression of a gene encoding the protein, thereby treating the disease or condition characterized with the protein overexpression. In some instances, the disease or the condition is a neuromuscular disease, a genetic disease, a muscle dystrophy, a muscle atrophy, a muscle wasting, cancer, a hereditary disease, or a cardiovascular disease of a human or a mammal.

Disclosed herein, in certain embodiments, is an immuno-oncology therapy comprising a molecule described above for the treatment of a disease or disorder in a patient in need thereof.

Disclosed herein, in certain embodiments, is a kit comprising a molecule, an oligonucleotide, or an oligonucleotide conjugate as described above.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 2A shows a plot of concentration (nM) vs % SSB mRNA in HCT116 cells transfected with SSB-siRNAs as described in molecular biology example 1. FIG. 2B shows a plot of concentration (nM) vs relative % SSB mRNA levels (% of untreated control) for DM1 control myoblasts transfected with SSB siRNAs as described in molecular biology example 2, and FIG. 2C shows a plot of concentration (nM) vs relative % SSB mRNA levels (% of untreated control) for SJCRH30 transfection with SSB siRNAs as described in molecular biology example 2.

FIG. 3A shows a plot of concentration (nM) vs relative MSTN mRNA levels (% of untreated control) for DM1 control myoblasts with MSTN siRNAs as described in molecular biology example 2 and FIG. 3B shows a plot of concentration (nM) vs relative MSTN mRNA levels (% of untreated control) for SJCRH30 transfection with MSTN siRNAs as described in molecular biology example 2.

FIG. 8A and FIG. 8B show in vivo MSTN mRNA downregulation and MSTN siRNA concentration in gastroc in one in vivo study measuring the concentration of mRNA in 7, 14, 21, 28, and 35 days, and FIG. 8C and FIG. 8D show in vivo MSTN mRNA downregulation and MSTN siRNA concentration in gastroc in another in vivo study measuring the concentration of mRNA in 7, 14, 21, 28, and 35 days

DETAILED DESCRIPTION OF THE DISCLOSURE

Figure 1:
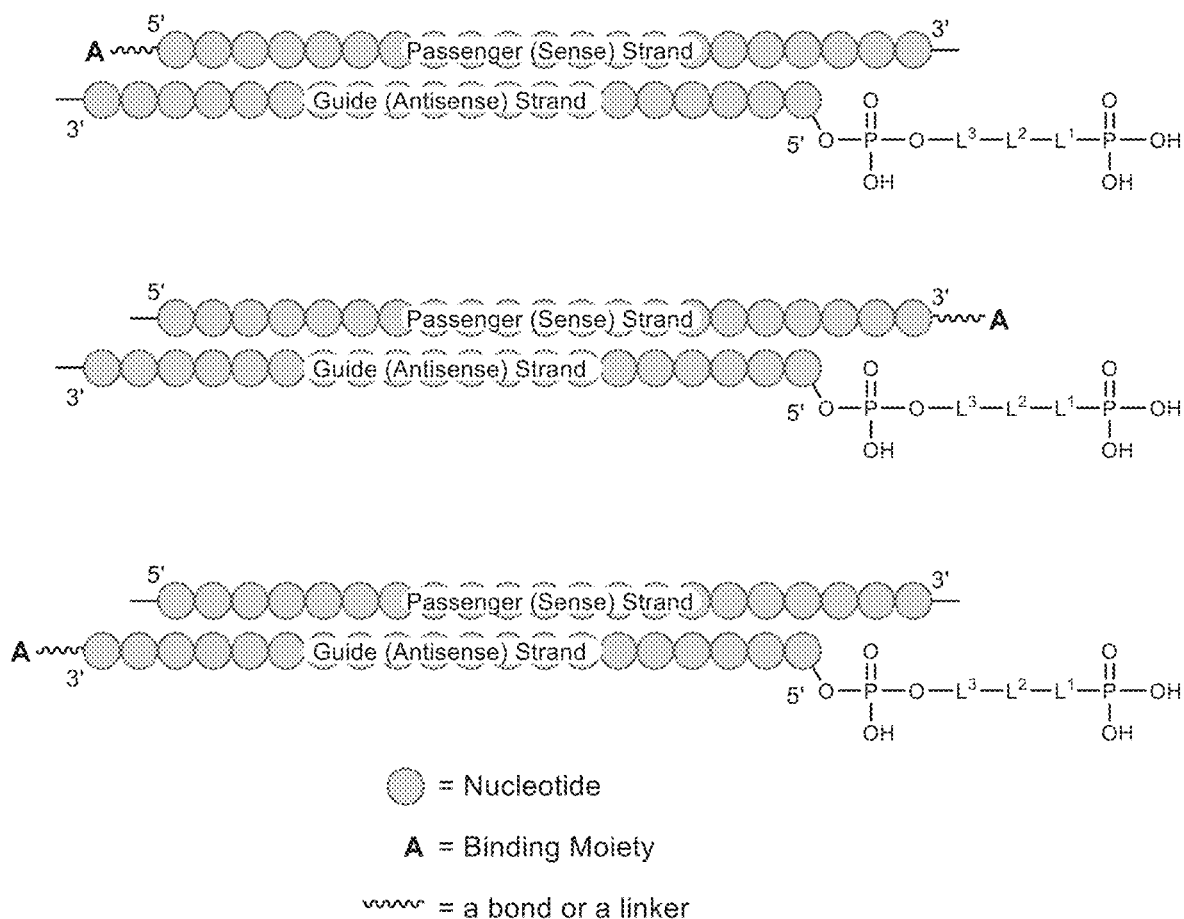
FIG. 1 shows a cartoon representation of a polynucleotide duplex, comprising a compound of formula (II) attached to the 5' end of the guide (antisense) strand, and further comprising a binding moiety A, which may be attached to the polynucleotide directly or via a linker, attached to the: 5' end of the passenger (sense) strand (top), 3' end of the passenger (sense) strand (middle), or the 3' end of the guide (antisense) strand (bottom).

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some embodiments, described herein include an oligonucleotide conjugate whose arrangement of the nucleic acid components effects intracellular uptake, stability, toxicity, efficacy, and/or non-specific immune stimulation. In some instances, the oligonucleotide conjugate comprises a binding moiety conjugated to a polynucleic acid molecule and a polymer. In some embodiments, the oligonucleotide conjugate comprises a compound according to Formula (II):

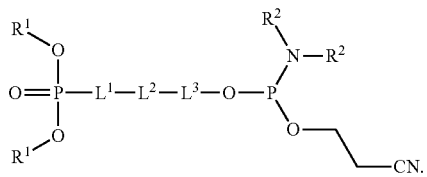

Formula (II)

In some embodiments, an oligonucleotide conjugate comprising a binding moiety conjugated to a polynucleic acid molecule and a polymer arranged as described herein enhances intracellular uptake, stability, and/or efficacy. In some instances, an oligonucleotide conjugate comprising a binding moiety conjugated to a polynucleic acid molecule and a polymer arranged as described herein reduces toxicity and/or non-specific immune stimulation. In some cases, the oligonucleotide conjugate comprises a compound according to Formula (II):

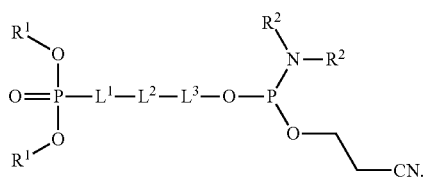

Formula (II)

In additional embodiments, described herein include a kit, which comprises one or more of the molecules described herein.

Therapeutic Molecule Platform

In some embodiments, an oligonucleotide conjugate (e.g., a therapeutic oligonucleotide conjugate) described herein comprises a binding moiety conjugated to a polynucleic acid molecule comprising one or more modified nucleotides and a polymer. In some embodiments, the oligonucleotide conjugate comprises a compound according to Formula (I) or Formula (I-A):

A-B      Formula (I), wherein,
A is a binding moiety; and
B is an oligonucleotide comprising a compound of Formula (II).

A-B-C      Formula (I-A);

wherein,
A is a binding moiety; and
B is an oligonucleotide comprising a compound of Formula (II) or (IIa)
C is optionally a polymer.

In some embodiments, the oligonucleotide comprises a compound according to Formula (II):

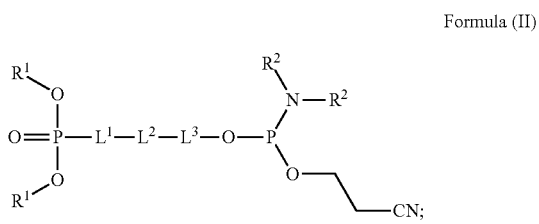

Formula (II)

wherein,
each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl;
each $R^2$ is independently hydrogen, deuterium, substituted or unsubstituted $C_1$-$C_6$ alkyl, or substituted or unsubstituted $C_1$-$C_0$ heteroalkyl;
or two $R^2$ are taken together with the nitrogen atom to which they are attached to form a substituted or unsubstituted $C_2$-$C_{10}$ heterocycloalkyl;
$L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;
$L^2$ is a bond, O, S, $NR^3$, substituted or unsubstituted $C_4$-$C_7$ cycloalkylene, substituted or unsubstituted $C_4$-$C_7$ heterocycloalkylene, substituted or unsubstituted $C_5$-$C_8$ arylene, or substituted or unsubstituted $C_4$-$C_8$ heteroarylene;
wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;
$L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene; and
wherein at least two of $L^1$, $L^2$ and $L^3$ are not a bond.

In some embodiments of the compound of Formula (II), $L^2$ is bond, O, S, or $NR^3$. In some embodiments, $L^2$ is O, S, or $NR^3$. In some embodiments, $L^2$ is $NR^3$. In some embodiments, $L^2$ is O. In some embodiments, $L^2$ is S. In some embodiments, $L^2$ is a bond.

In some embodiments of the compound of Formula (II), $L^2$ is substituted or unsubstituted $C_4$-$C_7$ cycloalkylene. In some embodiments, $L^2$ is substituted or unsubstituted $C_5$-$C_8$ arylene. In some embodiments, $L^2$ is unsubstituted $C_4$-$C_7$ cycloalkylene. In some embodiments, $L^2$ is phenylene. In some embodiments. $L^2$ is methylene. In some embodiments, $L^2$ is unsubstituted $C_5$-$C_8$ arylene. In some embodiments, $L^2$ is phenylene. In some embodiments. $L^2$ is methylene. In some embodiments, $L^2$ is cyclohexyl.

In some embodiments of the compound of Formula (II), $L^1$ is substituted or unsubstituted $C_1$-$C_5$ alkylene, substituted or unsubstituted $C_2$-$C_5$ alkenylene, or substituted or unsubstituted $C_2$-$C_5$ alkynylene; and $L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene. In some embodiments, $L^1$ is $C_1$-$C_5$ alkylene, $C_1$-$C_3$ alkylene, or $C_1$-$C_5$ alkynylene; and $L^3$ is $C_1$-$C_5$ alkylene, $C_1$-$C_3$ alkenylene, or $C_1$-$C_5$ alkynylene. In some embodiments. $L^1$ is $C_1$-$C_5$ alkylene; and $L^3$ is $C_1$-$C_5$ alkylene.

In some embodiments of the compound of Formula (II), at least two of $L^1$, $L^2$ and $L^3$ are not a bond. In some embodiments, $L^1$ is bond. In some embodiments, $L^3$ is bond.

In some embodiments of the compound of Formula (II), each $R^1$ is independently substituted or unsubstituted $C_1$-$C_6$ alkyl or substituted or unsubstituted $C_1$-$C_6$ heteroalkyl. In some embodiments, each $R^1$ is independently substituted or unsubstituted $C_1$-$C_6$ alkyl. In some embodiments, each $R^1$ is independently —$CH_3$, —$CH_2CH_3$, —$CH_2CH_2CH_3$, or —$CH_2(CH_3)_2$. In some embodiments, each $R^1$ is independently —$CH_3$, —$CH_2CH_2CH_3$, or —$CH_2(CH_3)_2$. In some embodiments, each $R^1$ is —$CH_3$.

In some embodiments of the compound of Formula (II), each $R^2$ is independently substituted or unsubstituted $C_1$-$C_6$ alkyl or substituted or unsubstituted $C_1$-$C_6$ heteroalkyl. In some embodiments, each $R^2$ is independently substituted or unsubstituted $C_1$-$C_6$ alkyl. In some embodiments, each $R^2$ is independently —CH, —$CH_2CH_3$, —$CH_2CH_2CH_3$, or —$CH_2(CH_3)_2$. In some embodiments, each $R^2$ is independently —$CH_3$, —$CH_2CH_2CH_3$, or —$CH_2(CH_3)_2$. In some embodiments, each $R^2$ is —$CH_2(CH_3)_2$.

In some embodiments of the compound of Formula (II), two $R^2$ are taken together with the nitrogen atom to which they are attached to form a substituted or unsubstituted $C_2$-$C_{10}$ heterocycloalkyl.

In some embodiments of the compound of Formula (II), $R^3$ is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl. In some embodiments, $R^3$ is selected from unsubstituted or substituted monocyclic carbocycle, and unsubstituted or substituted monocyclic heterocycle. In some embodiments, $R^3$ is hydrogen.

In some embodiments of Formula (II), the compound is selected from the group consisting of:

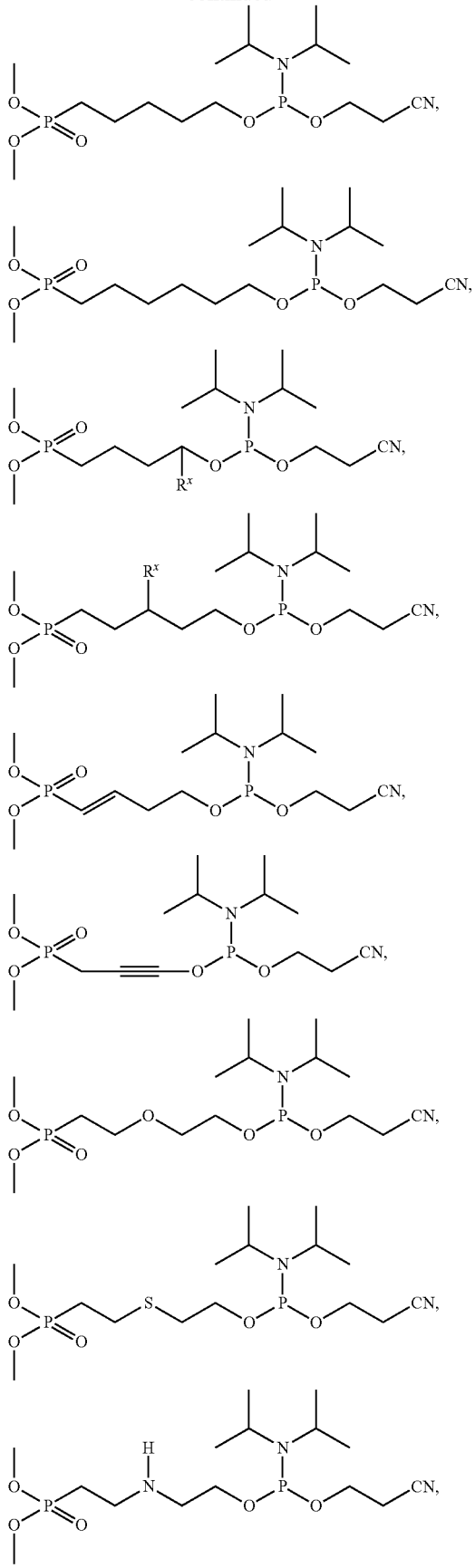

-continued

-continued

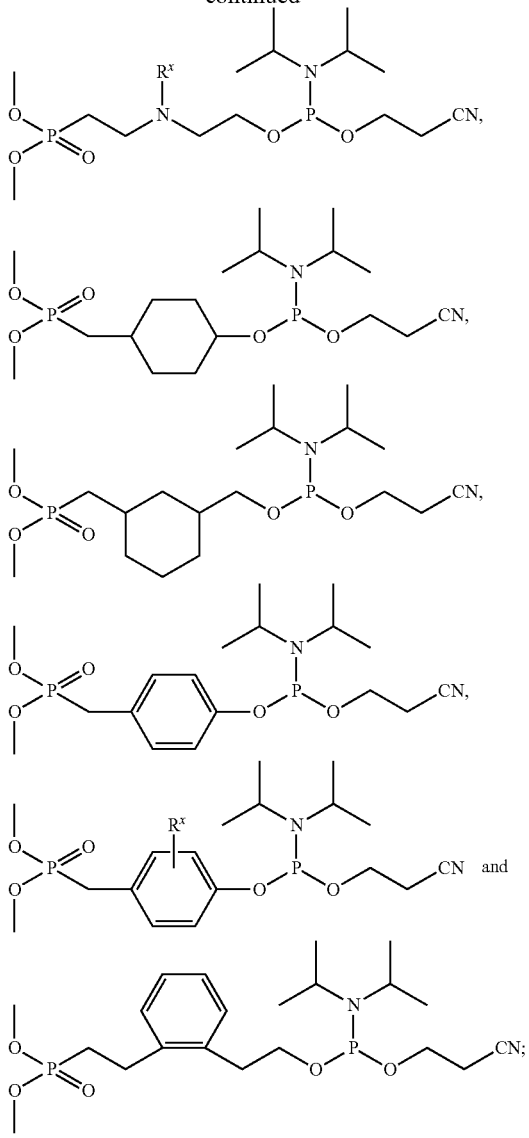

wherein R$^x$ is H, halogen, unsubstituted or substituted C$_1$-C$_6$alkyl, unsubstituted or substituted C$_1$-C$_6$fluoroalkyl, unsubstituted or substituted C$_1$-C$_6$heteroalkyl, unsubstituted or substituted monocyclic carbocycle, unsubstituted or substituted monocyclic heterocycle, —CN, —OH, —O— alkyl, —CO$_2$H, —CO$_2$-alkyl, —CH$_2$CO$_2$H, —CH$_2$CO$_2$-alkyl, —C(=O)NH$_2$, —C(=O)NH-alkyl, —CH$_2$C(=O)NH$_2$, —CH$_2$C(=O)NH-alkyl, NH$_2$, —NH-alkyl, —CH$_2$NH$_2$, —CH$_2$NH-alkyl, —NHC(=O)alkyl, —CH$_2$NHC(=O)alkyl, —SH, —S-alkyl, —S(=O)H, —S(=O)alkyl, —SO$_2$H, —SO$_2$-alkyl, —SO$_2$NH$_2$ or —SO$_2$NH-alkyl.

In some embodiments, R$^x$ is halogen, unsubstituted or substituted C$_1$-C$_6$alkyl, unsubstituted or substituted C$_1$-C$_6$fluoroalkyl, unsubstituted or substituted C$_1$-C$_6$heteroalkyl, unsubstituted or substituted monocyclic carbocycle, unsubstituted or substituted monocyclic heterocycle. In some embodiments, R$^x$ is H —CN, —OH, —O-alkyl, —CO$_2$H, —CO$_2$-alkyl, —CH$_2$CO$_2$H, —CH$_2$CO$_2$-alkyl, —C(=O)NH$_2$, —C(=O)NH-alkyl, —CH$_2$C(=O)NH$_2$, —CH$_2$C(=O)NH-alkyl, NH$_2$, —NH-alkyl, —CH$_2$NH$_2$, —CH$_2$NH-alkyl, —NHC(=O)alkyl, —CH$_2$NHC(=O)alkyl. —SH, —S-alkyl, —S(=O)H, —S(=O)alkyl, —SO$_2$H, —SO$_2$-alkyl, —SO$_2$NH$_2$ or —SO$_2$NH-alkyl. In some embodiments, R$^x$ is halogen. In some embodiments, R$^x$ is H.

In some embodiments, the oligonucleotide comprises a compound according to Formula (III):

Formula (III)

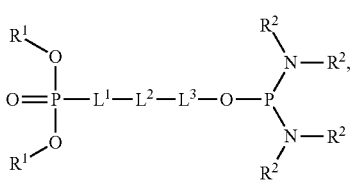

wherein,
each R$^1$ is independently substituted or unsubstituted C$_1$-C$_6$ alkyl, substituted or unsubstituted C$_1$-C$_6$ fluoroalkyl, or substituted or unsubstituted C$_1$-C$_6$ heteroalkyl;
each R$^2$ is independently hydrogen, deuterium, substituted or unsubstituted C$_1$-C$_6$ alkyl, or substituted or unsubstituted C$_1$-C$_6$ heteroalkyl;
or two R$^2$ are taken together with the nitrogen atom to which they are attached to form a substituted or unsubstituted C$_2$-C$_{10}$ heterocycloalkyl;
L$^1$ is a bond, substituted or unsubstituted C$_1$-C$_5$ alkylene, substituted or unsubstituted C$_2$-C$_5$ alkenylene, or substituted or unsubstituted C$_2$-C$_5$ alkynylene;
L$^2$ is a bond, O, S, NR$_3$, substituted or unsubstituted C$_4$-C$_7$ cycloalkylene, substituted or unsubstituted C$_4$-C$_7$ heterocycloalkylene, substituted or unsubstituted C$_5$-C$_8$ arylene, or substituted or unsubstituted C$_4$-C$_8$ heteroarylene;
wherein R$^3$, when present, is selected from hydrogen, unsubstituted or substituted C$_1$-C$_6$ alkyl, unsubstituted or substituted C$_1$-C$_6$ fluoroalkyl, unsubstituted or substituted C$_1$-C$_6$ heteroalkyl, unsubstituted or substituted monocyclic carbocycle, and unsubstituted or substituted monocyclic heterocycle;
L is a bond, substituted or unsubstituted C$_1$-C$_5$ alkylene, substituted or unsubstituted C$_2$-C$_5$ alkenylene, or substituted or unsubstituted C$_2$-C$_5$ alkynylene; and
wherein at least two of L$^1$, L$^2$ and L$^3$ are not a bond.

In some embodiments, B is an oligonucleotide comprising a 3'-terminus and a 5'-terminus, wherein one of the termini comprises a compound of Formula (IIa). In some embodiments, B is an oligonucleotide comprising a 3'-terminus and a 5'-terminus, wherein the 5'-termini comprises a compound of Formula (IIa).

Formula (IIa)

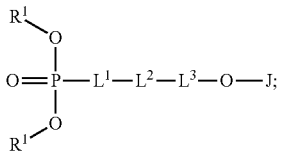

wherein;
each R$^1$ is independently substituted or unsubstituted C$_1$-C$_6$ alkyl, substituted or unsubstituted C$_1$-C$_6$ fluoroalkyl, or substituted or unsubstituted C$_1$-C$_6$ heteroalkyl;
L$^1$ is a bond, substituted or unsubstituted C$_1$-C$_5$ alkylene, substituted or unsubstituted C$_2$-C$_5$ alkenylene, or substituted or unsubstituted C$_2$-C$_5$ alkynylene;

L² is a bond, O, S, NR³, substituted or unsubstituted C₄-C₇ cycloalkylene, substituted or unsubstituted C₄-C₇ heterocycloalkylene, substituted or unsubstituted C₅-C₈ arylene, or substituted or unsubstituted C₄-C₈ heteroarylene;
  wherein R³, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;
L³ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;
J is an internucleotide linking group linking to the adjacent nucleotide of the polynucleotide; and
wherein at least two of L¹, L² and L are not a bond.

In some embodiments of the compound of Formula (IIa), L² is bond, O, S, or NR³. In some embodiments, L² is O, S, or NR³. In some embodiments, L² is NR³. In some embodiments, L² is O. In some embodiments, L² is S. In some embodiments, L² is a bond.

In some embodiments of the compound of Formula (IIa), L² is substituted or unsubstituted C₄-C₇ cycloalkylene. In some embodiments, L² is substituted or unsubstituted C₅-C₈ arylene. In some embodiments, L² is unsubstituted C₄—C, cycloalkylene. In some embodiments, L² is phenylene. In some embodiments, L² is methylene. In some embodiments, L² is unsubstituted C₅-C₈ arylene. In some embodiments, L² is phenylene. In some embodiments. L² is methylene. In some embodiments, L² is cyclohexyl.

In some embodiments of the compound of Formula (IIa), L¹ is substituted or unsubstituted $C_1$-$C_5$ alkylene, substituted or unsubstituted $C_2$-$C_5$ alkenylene, or substituted or unsubstituted $C_2$-$C_5$ alkynylene; and L³ is a bond, substituted or unsubstituted $C_1$-$C_5$ alkylene, substituted or unsubstituted $C_2$-$C_5$ alkenylene, or substituted or unsubstituted $C_2$-$C_5$ alkynylene. In some embodiments, L¹ is $C_1$-$C_5$ alkylene, $C_1$-$C_3$ alkenylene, or $C_1$-$C_5$ alkynylene; and L³ is $C_1$-$C_5$ alkylene, $C_1$-$C_3$ alkenylene, or $C_1$-$C_5$ alkynylene. In some embodiments, L¹ is $C_1$-$C_5$ alkylene; and L³ is $C_1$-$C_5$ alkylene.

In some embodiments of the compound of Formula (IIa), at least two of L¹, L² and L³ are not a bond. In some embodiments. L¹ is bond. In some embodiments. L is bond.

In some embodiments of Formula (IIa), each R¹ is independently substituted or unsubstituted $C_1$-$C_6$ alkyl or substituted or unsubstituted $C_1$-$C_6$ heteroalkyl. In some embodiments, each R¹ is independently substituted or unsubstituted $C_1$-$C_6$ alkyl. In some embodiments, each R¹ is independently —CH₃, —CH₂CH₃, —CH₂CH₂CH₃, or —CH₂(CH₃)₂. In some embodiments, each R¹ is independently —CH₃, —CH₂CH₂CH₃, or —CH₂(CH₃)₂. In some embodiments, each R¹ is —CH₃.

In some embodiments of Formula (IIa), each R² is independently substituted or unsubstituted $C_1$-$C_6$ alkyl or substituted or unsubstituted $C_1$-$C_6$ heteroalkyl. In some embodiments, each R² is independently substituted or unsubstituted $C_1$-$C_6$ alkyl. In some embodiments, each R² is independently —CH₃, —CH₂CH₃, —CH₂CH₂CH₃, or —CH₂(CH₃)₂. In some embodiments, each R² is independently —CH₃, —CH₂CH₂CH₃, or —CH₂(CH₃)₂. In some embodiments, each R² is —CH₂(CH₃)₂.

In some embodiments of Formula (IIa), two R² are taken together with the nitrogen atom to which they are attached to form a substituted or unsubstituted $C_2$-$C_{10}$ heterocycloalkyl.

In some embodiments of Formula (IIa), R¹ is selected from hydrogen, unsubstituted or substituted $C_1$-$C_6$alkyl, unsubstituted or substituted $C_1$-$C_6$ fluoroalkyl, unsubstituted or substituted $C_1$-$C_6$ heteroalkyl. In some embodiments, R³ is selected from unsubstituted or substituted monocyclic carbocycle, and unsubstituted or substituted monocyclic heterocycle. In some embodiments, R³ is hydrogen.

In some embodiments, the oligonucleotide comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, or more compounds of Formula (II) (e.g., Formula IIa). In some cases, the oligonucleotide comprises at least about 1, about 2, about 3, about 4, about 5, about 6, about 7, about 8, about 9, about 10, about 11, about 12, about 13, about 14, about 15, or more compounds of Formula (II) (e.g., Formula IIa). In some instances, the compounds of Formula (II) (e.g., Formula IIa) are in tandem within the oligonucleotide. In other instances, the compounds Formula (II) (e.g., Formula IIa) are interspersed within the oligonucleotide, with nucleotides modified by one or more additional modification described below.

In some instances, the oligonucleotide comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification, in which the modification is a compound of Formula (II) (e.g., Formula IIa). For example, where the oligonucleotide has 20 nucleosides, the oligonucleotide having about 60% modification comprises about 12 nucleosides substituted with 12 Formula (II) (e.g., Formula IIa) compounds.

Figure 10:
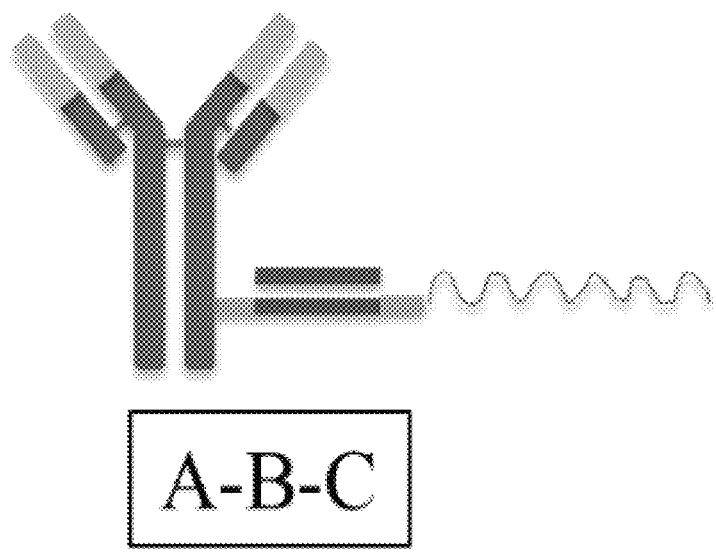
FIG. 10 illustrates an oligonucleotide conjugate with a formula A-B-C (Formula I-A), where A is a binding moiety. B is an oligonucleotide, and C is optionally a polymer.

In some embodiments, an oligonucleotide conjugate is a molecule as illustrated in FIG. 10.

Figure 11:
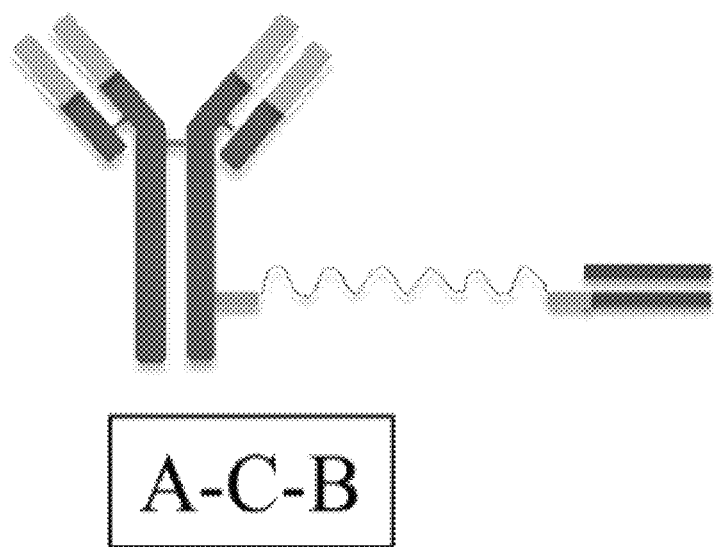
FIG. 11 illustrates an oligonucleotide conjugate with a formula A-C-B, where A is a binding moiety, B is an oligonucleotide, and C is optionally a polymer.

In some embodiments, an oligonucleotide conjugate is a molecule as illustrated in FIG. 11.

Figure 12:
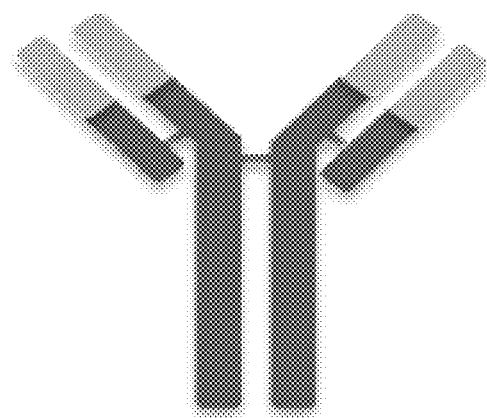
FIG. 12 illustrates an antibody of oligonucleotide conjugates as shown in FIG. 10 and FIG. 11.

The antibody (FIG. 12) as illustrated in FIG. 10 and FIG. 11 is for representation purposes only and encompasses a humanized antibody or binding fragment thereof, anti-human antibody, anti-murine antibody (e.g., anti-mouse antibody, anti-rat antibody, etc.), chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof Additional Modifications In some embodiments, the additional modifications include synthetic or artificial nucleotide analogues or bases comprising modifications at one or more of ribose moiety, phosphate moiety, nucleoside moiety, or a combination thereof.

In some embodiments, a modification at a 2' hydroxyl group include 2'-deoxy, 2'-deoxy-2'-fluoro, 2'-deoxy-2'-fluoro, 2'-O-aminopropyl (2'-O-AP), 2-O-dimethylaminoethyl (2'-O-DMAOE), 2'-O-dimethylaminopropyl (2'-O-

DMAP), 2'-O-dimethylaminoethyloxyethyl (2'-O-DMAEOE), or 2'-O—N-methylacetamido (2'-O-NMA).

In some embodiments, a nucleotide analogue comprises a modified base such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. 5'-Phosphonate modified nucleotides also include those nucleotides that are modified with respect to the sugar moiety, as well as 5'-phosphonate modified nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, a nucleotide analogue or artificial nucleotide base described above comprises a 5'-phosphonate modified nucleotide nucleic acid with a modification at a 5' hydroxyl group of the ribose moiety. In some embodiments, a nucleotide analogue or artificial nucleotide base described above comprises a 5'-vinylphosphonate modified nucleotide nucleic acid with a modification at a 5' hydroxyl group of the ribose moiety.

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties.

In some instances, the 5'-phosphonate modified nucleotide is further modified at the 2' hydroxyl group in a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of 5'-phosphonate modified LNA are illustrated below, wherein J is an internucleotide linkage.

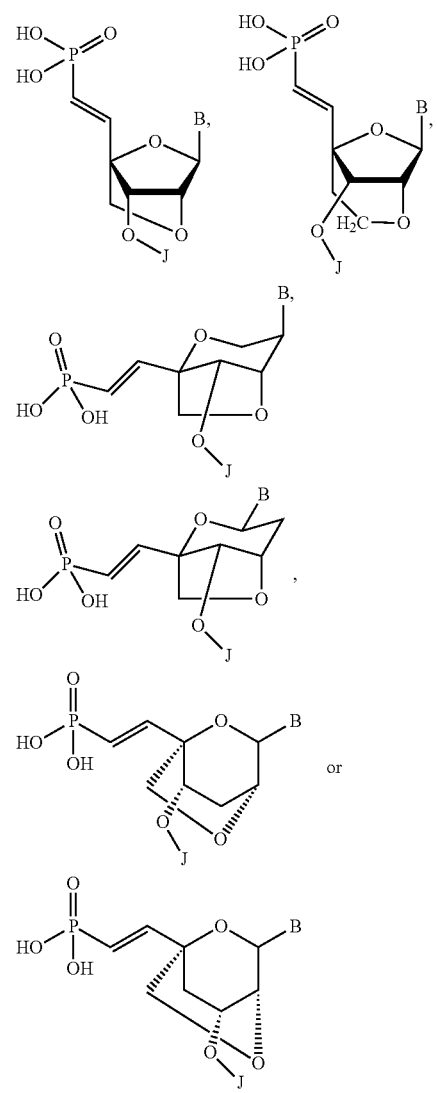

In some embodiments, the additional modification further comprises a morpholino, a peptide nucleic acid (PNA), a methylphosphonate nucleotide, a thiolphosphonate nucleotide, a 2'-fluoro N3-P5'-phosphoramidite, or a 1', 5'-anhydrohexitol nucleic acid (HNA). Morpholino or phosphorodiamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides. A non-limiting example of a 5'-phosphonate modified morpholino oligonucleotide is illustrated below.

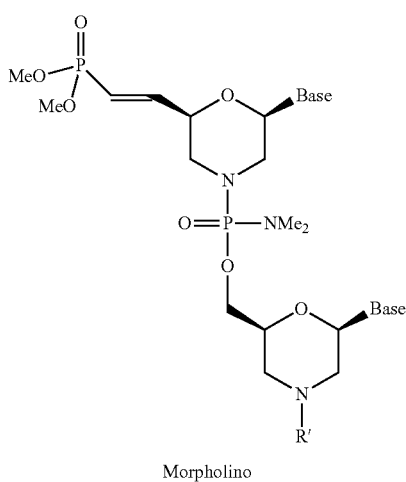

Morpholino

In some embodiments, a 5'-phosphonate modified morpholino or PMO described above is a PMO comprising a positive or cationic charge. In some instances, the PMO is PMOplus (Sarepta). PMOplus refers to phosphorodiamidate morpholino oligomers comprising any number of (1-piperazino)phosphinylideneoxy, (1-(4-(omega-guanidino-alkanoyl))-piperazino)phosphinylideneoxy linkages (e.g, as such those described in PCT Publication No. WO2008/036127. In some cases, the PMO is a PMO described in U.S. Pat. No. 7,943,762.

In some embodiments, a morpholino or PMO described above is a PMO-X (Sarepta). In some cases, PMO-X refers to phosphorodiamidate morpholino oligomers comprising at least one linkage or at least one of the disclosed terminal modifications, such as those disclosed in PCT Publication No. WO2011/150408 and U.S. Publication No. 2012/0065169.

In some embodiments, a morpholino or PMO described above is a PMO as described in Table 5 of U.S. Publication No. 2014/0296321.

In some embodiments, peptide nucleic acid (PNA) does not contain sugar ring or phosphate linkage and the bases are attached and appropriately spaced by oligoglycine-like molecules, therefore, eliminating a backbone charge.

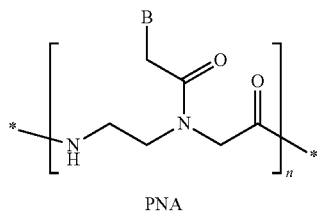

PNA

In some embodiments, one or more modifications described above occur at the internucleotide linkage. In some instances, modified internucleotide linkage includes, but is not limited to, phosphorothioates; phosphorodithioates; methylphosphonates; 5'-alkylenephosphonates; 5'-methylphosphonate; 3'-alkylene phosphonates; borontrifluoridates; borano phosphate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or polyamides wherein the bases are attached to the aza nitrogens of the backbone directly or indirectly; and combinations thereof.

In some instances, the modification is a methyl or thiol modification such as methylphosphonate or thiolphosphonate modification. Exemplary thiolphosphonate nucleotide (left), phosphorodithioates (center) and methylphosphonate nucleotide (right) are illustrated below.

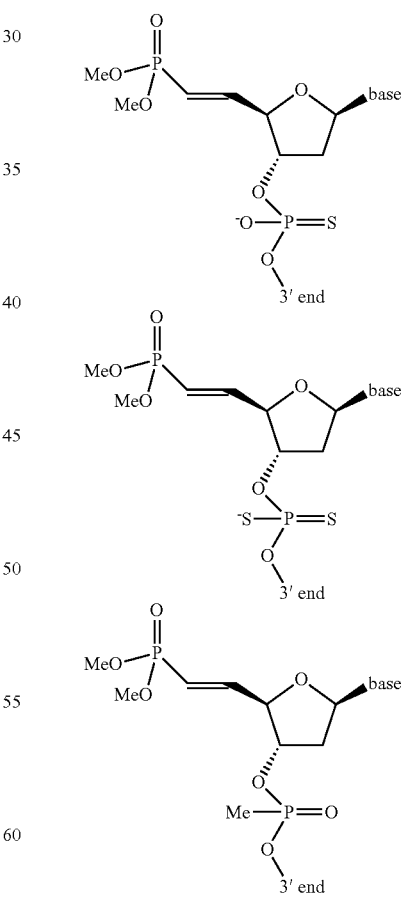

In some instances, a 5'-vinylphosphonate modified nucleotide includes, but is not limited to, phosphoramidites illustrated as:

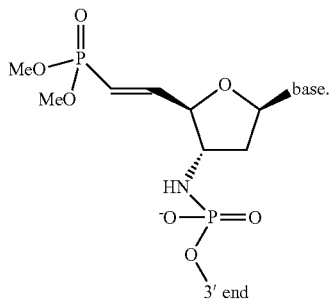

In some instances, the modified internucleotide linkage is a phosphorodiamidate linkage. A non-limiting example of a phosphorodiamidate linkage with a morpholino system is shown below.

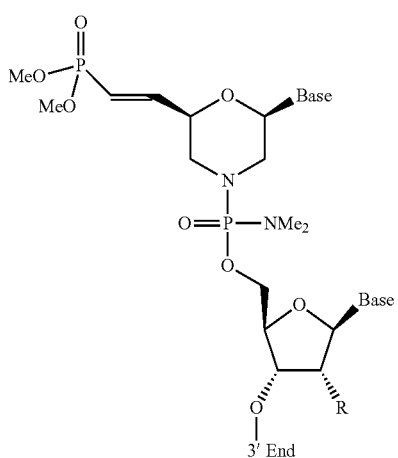

In some instances, the modified internucleotide linkage is a methylphosphonate linkage. A non-limiting example of a methylphosphonate linkage is shown below.

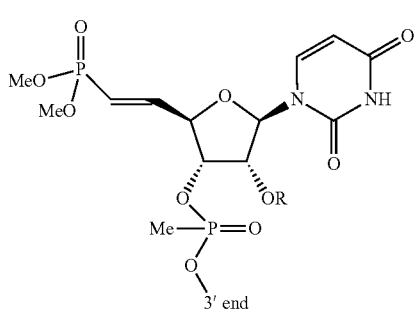

In some instances, the modified internucleotide linkage is an amide linkage. A non-limiting example of an amide linkage is shown below.

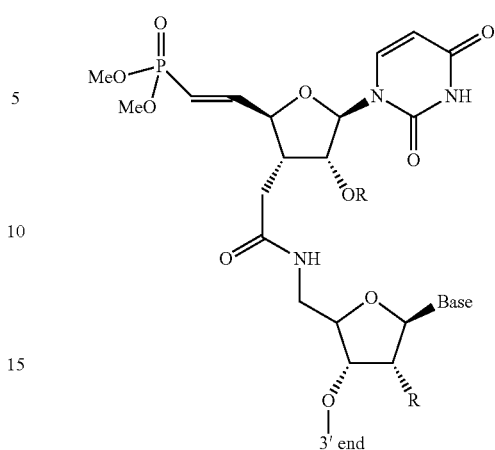

In some embodiments, one or more modifications comprise a modified phosphate backbone in which the modification generates a neutral or uncharged backbone. In some instances, the phosphate backbone is modified by alkylation to generate an uncharged or neutral phosphate backbone. As used herein, alkylation includes methylation, ethylation, and propylation. In some cases, an alkyl group, as used herein in the context of alkylation, refers to a linear or branched saturated hydrocarbon group containing from 1 to 6 carbon atoms. In some instances, exemplary alkyl groups include, but are not limited to, methyl, ethyl, n-propyl, isopropyl, n-butyl, isobutyl, sec-butyl, tert-butyl, n-pentyl, isopentyl, neopentyl, hexyl, isohexyl, 1, 1-dimethylbutyl, 2,2-dimethylbutyl, 3,3-dimethylbutyl, and 2-ethylbutyl groups. In some cases, a modified phosphate is a phosphate group as described in U.S. Pat. No. 9,481,905.

In some embodiments, additional modified phosphate backbones comprise methylphosphonate, ethylphosphonate, methylthiophosphonate, or methoxyphosphonate. In some cases, the modified phosphate is methylphosphonate. In some cases, the modified phosphate is ethylphosphonate. In some cases, the modified phosphate is methylthiophosphonate. In some cases, the modified phosphate is methoxyphosphonate.

In some embodiments, additional modified phosphate backbones comprise one of the followings:

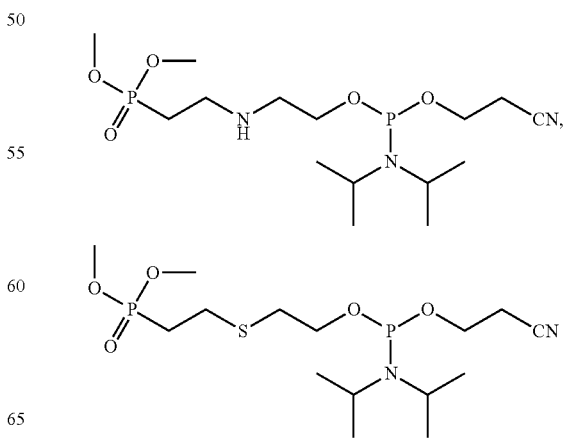

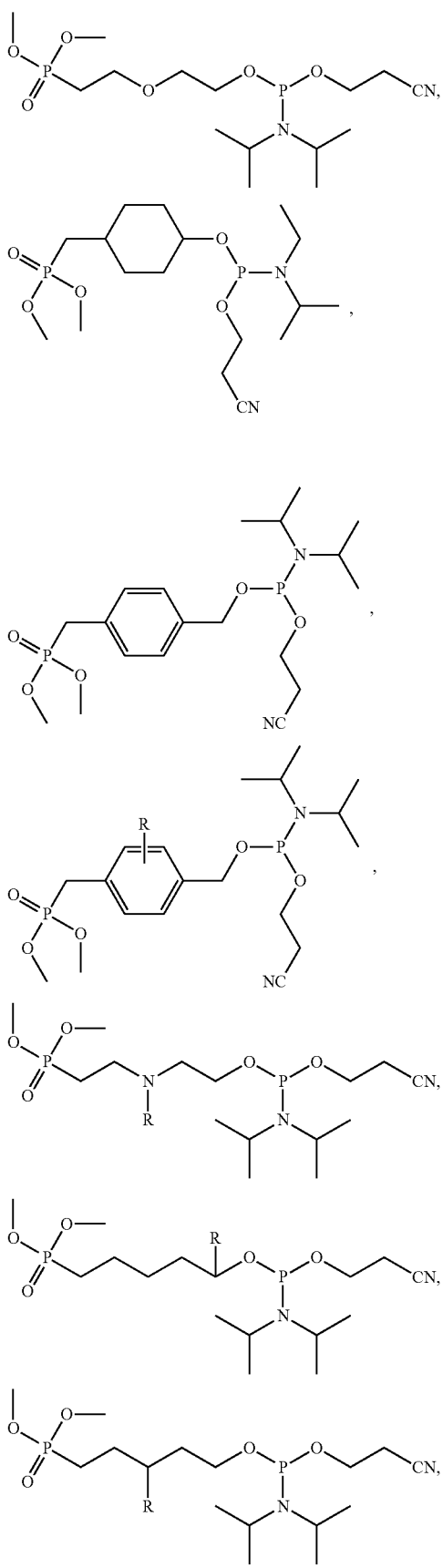

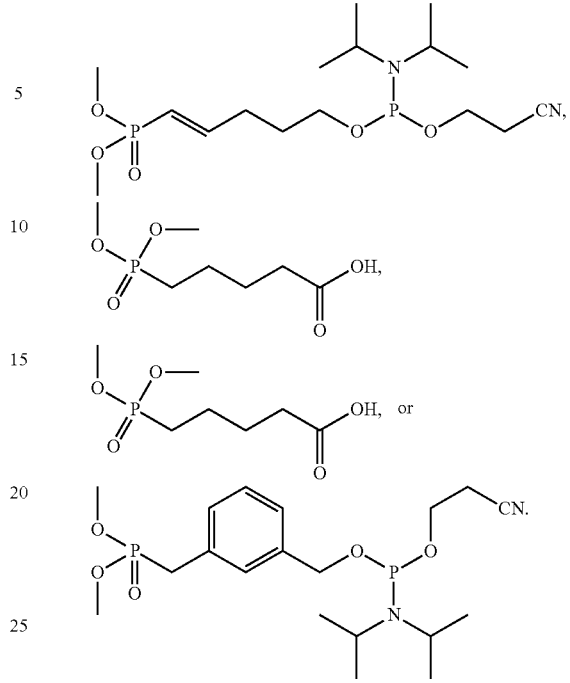

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' $C_5$-aminoalkyl dT. In an additional alternative, the 3'-terminus is optionally conjugated with an abasic site, e.g., with an apurinic or apyrimidinic site.

In some embodiments, the oligonucleotide comprising a compound of Formula (II) (e.g., Formula IIa) further comprises one or more of the artificial nucleotide analogues described herein. In some instances, the oligonucleotide comprising a compound of Formula (II) (e.g., Formula IIa) further comprises one or more, e.g., 1, 2, 3, 4, 5, 6, 7, 8, 9, 10, 11, 12, 13, 14, 15, 16, 17, 18, 20, 25, or more additional modifications such as, but not limited to, 2'-O-methyl, 2'-0-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2-O-dimethylaminopropyl (2'-O-DMAP), 2'-O-dimethylaminoethyloxyethyl (2'-O-DMAEOE), or 2-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the oligonucleotide comprising a compound of Formula (II) (e.g., Formula IIa) further comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the oligonucleotide comprising a compound of Formula (II) (e.g., Formula IIa) further comprises 1, 2, 3, 4, 5, 6, 7, 8, 9, 10, 11, 12, 13, 14, 15, 16, 17, 18, 20, 25, or more of 2'-O-methyl modified nucleotides. In some instances, the oligonucleotide comprising a compound of Formula (II) (e.g., Formula IIa) further comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the oligonucleotide comprising a compound of Formula (II) (e.g., Formula IIa) further comprises 1, 2, 3, 4, 5, 6, 7, 8, 9, 10, 11, 12, 13, 14, 15, 16, 17, 18, 20, 25, or more of thiolphosphonate nucleotides.

In some instances, about 5 to about 100% of the oligonucleotide comprising a compound of Formula (II) (e.g., Formula IIa) comprise the artificial nucleotide analogues described herein. In some instances, about 5%, 10%, 15%, 20%, 25%, 30%, 35%, 40%, 45%, 50%, 55%, 60%. 65%, 70%, 75%, 80%, 85%, 90%, 95%, or 100% of the polynucleic acid molecule comprise the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-0-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, the oligonucleotide (or B of A-B formula) described herein comprises RNA or DNA. In some cases, the oligonucleotide comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances. RNA comprises rRNA. In some instances, RNA comprises hnRNA. In some instances, the RNA comprises siRNA. In some cases, the oligonucleotide comprises a sense strand (or passenger strand) of a siRNA. In other cases, the oligonucleotide comprises an antisense (or guide strand) of a siRNA.

In some embodiments, the oligonucleotide is from about 10 to about 50 nucleotides in length. In some instances, the oligonucleotide is from about 10 to about 30, from about 15 to about 30, from about 18 to about 25, from about 18 to about 24, from about 19 to about 23, or from about 20 to about 22 nucleotides in length.

In some embodiments, the oligonucleotide is about 50 nucleotides in length. In some instances, the oligonucleotide is about 45 nucleotides in length. In some instances, the oligonucleotide is about 40 nucleotides in length. In some instances, the oligonucleotide is about 35 nucleotides in length. In some instances, the oligonucleotide is about 30 nucleotides in length. In some instances, the oligonucleotide is about 25 nucleotides in length. In some instances, the oligonucleotide is about 20 nucleotides in length. In some instances, the oligonucleotide is about 19 nucleotides in length. In some instances, the oligonucleotide is about 18 nucleotides in length. In some instances, the oligonucleotide is about 17 nucleotides in length. In some instances, the oligonucleotide is about 16 nucleotides in length. In some instances, the oligonucleotide is about 15 nucleotides in length. In some instances, the oligonucleotide is about 14 nucleotides in length. In some instances, the oligonucleotide is about 13 nucleotides in length. In some instances, the oligonucleotide is about 12 nucleotides in length. In some instances, the oligonucleotide is about 11 nucleotides in length. In some instances, the oligonucleotide is about 10 nucleotides in length. In some instances, the oligonucleotide is from about 10 to about 50 nucleotides in length. In some instances, the oligonucleotide is from about 10 to about 45 nucleotides in length. In some instances, the oligonucleotide is from about 10 to about 40 nucleotides in length. In some instances, the oligonucleotide is from about 10 to about 35 nucleotides in length. In some instances, the oligonucleotide is from about 10 to about 30 nucleotides in length. In some instances, the oligonucleotide is from about 10 to about 25 nucleotides in length. In some instances, the oligonucleotide is from about 10 to about 20 nucleotides in length. In some instances, the oligonucleotide is from about 15 to about 25 nucleotides in length. In some instances, the oligonucleotide is from about 19 to about 23 nucleotides in length. In some instances, the oligonucleotide is from about 15 to about 30 nucleotides in length. In some instances, the oligonucleotide is from about 12 to about 30 nucleotides in length.

In some embodiments, the oligonucleotide is further hybridized with a second oligonucleotide to form a duplex. In some instances, the oligonucleotide is a sense strand or passenger strand. In some instances, the second oligonucleotide is an antisense strand or guide strand.

In some embodiments, the second oligonucleotide is from about 10 to about 50 nucleotides in length. In some instances, the second oligonucleotide is from about 10 to about 30, from about 15 to about 30, from about 18 to about 25, from about 18 to about 24, from about 19 to about 23, or from about 20 to about 22 nucleotides in length.

In some instances, the second oligonucleotide is about 50 nucleotides in length. In some instances, the second oligonucleotide is about 45 nucleotides in length. In some instances, the second oligonucleotide is about 40 nucleotides in length. In some instances, the second oligonucleotide is about 35 nucleotides in length. In some instances, the second oligonucleotide is about 30 nucleotides in length. In some instances, the second oligonucleotide is about 25 nucleotides in length. In some instances, the second oligonucleotide is about 20 nucleotides in length. In some instances, the second oligonucleotide is about 19 nucleotides in length. In some instances, the second oligonucleotide is about 18 nucleotides in length. In some instances, the second oligonucleotide is about 17 nucleotides in length. In some instances, the second oligonucleotide is about 16 nucleotides in length. In some instances, the second oligonucleotide is about 15 nucleotides in length. In some instances, the second oligonucleotide is about 14 nucleotides in length. In some instances, the second oligonucleotide is about 13 nucleotides in length. In some instances, the second oligonucleotide is about 12 nucleotides in length. In some instances, the second oligonucleotide is about 11 nucleotides in length. In some instances, the second oligonucleotide is about 10 nucleotides in length. In some instances, the second oligonucleotide is from about 10 to about 50 nucleotides in length. In some instances, the second oligonucleotide is from about 10 to about 45 nucleotides in length. In some instances, the second oligonucleotide is from about 10 to about 40 nucleotides in length. In some instances, the second oligonucleotide is from about 10 to about 35 nucleotides in length. In some instances, the second oligonucleotide is from about 10 to about 30 nucleotides in length. In some instances, the second oligonucleotide is from about 10 to about 25 nucleotides in length. In some instances, the second oligonucleotide is from about 10 to about 20 nucleotides in length. In some instances, the second oligonucleotide is from about 15 to about 25 nucleotides in length. In some instances, the second oligonucleotide is from about 15 to about 30 nucleotides in length. In some instances, the second oligonucleotide is from about 19 to about 23 nucleotides in length. In some instances, the second oligonucleotide is from about 12 to about 30 nucleotides in length.

In some embodiments, a polynucleic acid molecule comprises a first oligonucleotide and a second oligonucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides.

In some embodiments, the sequence of the polynucleic acid molecule is at least 40%, 50%, 55%, 60%, 65%, 70%, 75%, 80%, 85%, 90%, 95%, 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, the specificity of the polynucleic acid molecule that hybridizes to a target sequence described herein is a 95%, 98%, 99%, 99.5%, or 100% sequence complementarity of the polynucleic acid molecule to a target sequence. In some instances, the hybridization is a high stringent hybridization condition.

In some embodiments, the polynucleic acid molecule hybridizes to at least 8, 9, 10, 11, 12, 13, 14, 15, 16, 17, 18, 19, 20, or more contiguous bases of a target sequence described herein. Exemplary target sequence includes, but not limited to, any sequences of DMD gene or its mRNA, DMPK gene or its mRNA, any sequences of an oncogene or its mRNA, any genes related to hereditary or genetic diseases (e.g., GYS1), any sequences of a gene related to muscle atrophy, muscle dystrophy, or muscle wasting (e.g., DMD, DMPK, DUX4) and its mRNA. In some embodiments, the polynucleic acid molecule hybridizes to at least 8 contiguous bases of a target sequence described herein. In some embodiments, the polynucleic acid molecule hybridizes to at least 9 contiguous bases of a target sequence described herein. In some embodiments, the polynucleic acid molecule hybridizes to at least 10 contiguous bases of a target sequence described herein. In some embodiments, the polynucleic acid molecule hybridizes to at least 11 contiguous bases of a target sequence described herein. In some embodiments, the polynucleic acid molecule hybridizes to at least 12 contiguous bases of a target sequence described herein. In some embodiments, the polynucleic acid molecule hybridizes to at least 13 contiguous bases of a target sequence described herein. In some embodiments, the polynucleic acid molecule hybridizes to at least 14 contiguous bases of a target sequence described herein. In some embodiments, the polynucleic acid molecule hybridizes to at least 15 contiguous bases of a target sequence described herein. In some embodiments, the polynucleic acid molecule hybridizes to at least 16 contiguous bases of a target sequence described herein. In some embodiments, the polynucleic acid molecule hybridizes to at least 17 contiguous bases of a target sequence described herein. In some embodiments, the polynucleic acid molecule hybridizes to at least 18 contiguous bases of a target sequence described herein. In some embodiments, the polynucleic acid molecule hybridizes to at least 19 contiguous bases of a target sequence described herein. In some embodiments, the polynucleic acid molecule hybridizes to at least 20 contiguous bases of a target sequence described herein.

In some embodiments, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising a compound of Formula II (e.g., Formula IIa), 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribunuclease such as DNase, or exonuclease such as 5'-3' exonuclease and 3'-5' exonuclease. In some instances, 2'-O-methyl modified polynucleic acid molecule is nuclease resistant (e.g., RNase H, DNase, 5'-3' exonuclease or 3'-5' exonuclease resistant). In some instances, 2'O-methoxyethyl (2'-O-MOE) modified polynucleic acid molecule is nuclease resistant (e.g., RNase H, DNase, 5'-3' exonuclease or 3'-5' exonuclease resistant). In some instances, 2'-O-aminopropyl modified polynucleic acid molecule is nuclease resistant (e.g., RNase H, DNase, 5'-3' exonuclease or 3'-5' exonuclease resistant). In some instances, 2'-deoxy modified polynucleic acid molecule is nuclease resistant (e.g., RNase H, DNase, 5'-3' exonuclease or 3'-5' exonuclease resistant). In some instances, 2'-deoxy-2'-fluoro modified polynucleic acid molecule is nuclease resistant (e.g., RNase H, DNase, 5'-3' exonuclease or 3'-5' exonuclease resistant). In some instances, 2'-O-aminopropyl (2'-O-AP) modified polynucleic acid molecule is nuclease resistant (e.g., RNase H, DNase, 5'-3' exonuclease or 3'-5' exonuclease resistant). In some instances, 2'-O-dimethylaminoethyl (2'-O-DMAOE) modified polynucleic acid molecule is nuclease resistant (e.g., RNase H, DNase, 5'-3' exonuclease or 3'-5' exonuclease resistant). In some instances, 2'-O-dimethylaminopropyl (2'-O-DMAP) modified polynucleic acid molecule is nuclease resistant (e.g., RNase H, DNase, 5'-3' exonuclease or 3'-5' exonuclease resistant). In some instances, 2'-O-dimethylaminoethyloxyethyl (2'-O-DMAEOE) modified polynucleic acid molecule is nuclease resistant (e.g., RNase H, DNase, 5'-3' exonuclease or 3'-5' exonuclease resistant). In some instances, 2-O—N-methylacetamido (2'-0-NMA) modified polynucleic acid molecule is nuclease resistant (e.g., RNase H, DNase, 5'-3' exonuclease or 3'-5' exonuclease resistant). In some instances, LNA-modified polynucleic acid molecule is nuclease resistant (e.g., RNase H, DNase, 5'-3' exonuclease or 3'-5' exonuclease resistant). In some instances, ENA-modified polynucleic acid molecule is nuclease resistant (e.g., RNase H, DNase, 5'-3' exonuclease or 3'-5' exonuclease resistant). In some instances. HNA-modified polynucleic acid molecule is nuclease resistant (e.g., RNase H, DNase, 5'-3' exonuclease or 3'-5' exonuclease resistant). Morpholinos may be nuclease resistant (e.g., RNase H, DNase, 5'-3' exonuclease or 3'-5' exonuclease resistant). In some instances, PNA-modified polynucleic acid molecule is resistant to nucleases (e.g., RNase H, DNase, 5'-3' exonuclease or 3'-5' exonuclease resistant). In some instances, methylphosphonate nucleotide-modified polynucleic acid molecule is nuclease resistant (e.g., RNase H, DNase, 5'-3' exonuclease or 3'-5' exonuclease resistant). In some instances, thiolphosphonate nucleotide-modified polynucleic acid molecule is nuclease resistant (e.g., RNase H, DNase, 5'-3' exonuclease or 3'-5' exonuclease resistant). In some instances, polynucleic acid molecule comprising 2'-fluoro N3-P5'-phosphoramidites is nuclease resistant (e.g., RNase H, DNase, 5'-3' exonuclease resistant). In some instances, the 5' conjugates described herein inhibit 5'-3' exonucleolytic cleavage. In some instances, the 3' conjugates described herein inhibit 3'-5' exonucleolytic cleavage.

In some embodiments, one or more of the artificial modified nucleotide analogues comprising the compound of Formula II (e.g., Formula IIa) described herein have increased binding affinity towards their mRNA target relative to an equivalent natural polynucleotide acid molecule. The one or more of the modified nucleotide analogues comprising the compound of Formula II, 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites can have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, 2'-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, 2'-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA-modified polynucleic acid molecule has increased binding affinity toward their mRNA target relative to an equivalent natural polynucleic acid molecule. In some instances, ENA-modified polynucleic acid molecule has increased binding affinity toward their mRNA target relative to an equivalent natural polynucleic acid molecule. In some instances, PNA-modified polynucleic acid molecule has increased binding affinity toward their mRNA target relative to an equivalent natural polynucleic acid molecule. In some instances, HNA-modified polynucleic acid molecule has increased binding affinity toward their mRNA target relative to an equivalent natural polynucleic acid molecule. In some instances, morpholino-modified polynucleic acid molecule has increased binding affinity toward their mRNA target relative to an equivalent natural polynucleic acid molecule. In some instances, methylphosphonate nucleotide-modified polynucleic acid molecule has increased binding affinity toward their mRNA target relative to an equivalent natural polynucleic acid molecule. In some instances, thiolphosphonate nucleotide-modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a modified nucleotide analogues comprising the compound of Formula II (e.g., Formula IIa) described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer-conjugating moiety. In some instances, the aptamer conjugating moiety is a DNA aptamer-conjugating moiety. In some instances, the aptamer-conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer-conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA), the polynucleic acid molecule is modified to increase its stability. In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-0-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some embodiments, a polynucleic acid molecule described herein has RNAi activity that modulates expression of RNA encoded by a gene described supra. In some instances, a polynucleic acid molecule described herein is a double-stranded siRNA molecule that down-regulates expression of a gene, wherein one of the strands of the double-stranded siRNA molecule comprises a nucleotide sequence that is complementary to a nucleotide sequence of the gene or RNA encoded by the gene or a portion thereof, and wherein the second strand of the double-stranded siRNA molecule comprises a nucleotide sequence substantially similar to the nucleotide sequence of the gene or RNA encoded by the gene or a portion thereof. In some cases, a polynucleic acid molecule described herein is a double-stranded siRNA molecule that down-regulates expression of a gene, wherein each strand of the siRNA molecule comprises about 15 to 25, 18 to 24, or 19 to about 23 nucleotides, and wherein each strand comprises at least about 14, 17, or 19 nucleotides that are complementary to the nucleotides of the other strand. In some cases, a polynucleic acid molecule described herein is a double-stranded siRNA molecule that down-regulates expression of a gene, wherein each strand of the siRNA molecule comprises about 19 to about 23 nucleotides, and wherein each strand comprises at least about 19 nucleotides that are complementary to the nucleotides of the other strand.

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the poly nucleic acid molecule and target nucleic acids. Exemplary methods include those described in U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides; a zwitterionic modification that enhances the exonuclease resistance and biological activity of antisense oligonucleotides," *J. Med Chem.* 39(26):5100-5109 (1997)); Obika, et al. "Synthesis of 2'-0,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities." Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

One embodiment provides an oligonucleotide conjugate of Formula (I) or Formula (I-A):

A-B      Formula (I):

A-B-C      Formula (I-A);

wherein,

A is a binding moiety;

C is optionally a polymer;

B is an oligonucleotide comprising a nucleotide compound of or derived from Formula (II) (e.g., the phosphoamidite group of Formula (II) converts to a phosphate group in the oligonucleotide structure);

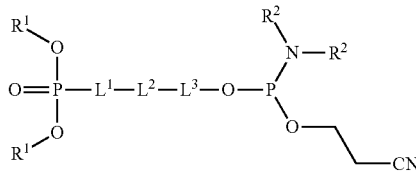

Formula (II)

wherein,
each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl;
each $R^2$ is independently hydrogen, deuterium, substituted or unsubstituted $C_1$-$C_6$ alkyl, or substituted or unsubstituted $C_1$-$C_6$ heteroalkyl;
or two $R^2$ are taken together with the nitrogen atom to which they are attached to form a substituted or unsubstituted $C_2$-$C_{10}$ heterocycloalkyl;
$L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;
$L^2$ is a bond, O, S, $NR^3$, substituted or unsubstituted $C_4$-$C_7$ cycloalkylene, substituted or unsubstituted $C_4$-$C_7$ heterocycloalkylene, substituted or unsubstituted $C_5$-$C_8$ arylene, or substituted or unsubstituted $C_4$-$C_8$ heteroarylene;
wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;
$L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene; and
wherein at least two of $L^1$, $L^2$ and $L^3$ are not a bond.

In some embodiments of the compound of Formula (II), $L^2$ is bond, O, S, or $NR^3$. In some embodiments, $L^2$ is O, S, or $NR^3$. In some embodiments. $L^2$ is $NR^3$. In some embodiments, $L^2$ is O. In some embodiments, $L^2$ is S. In some embodiments, $L^2$ is a bond.

In some embodiments of the compound of Formula (II), $L^2$ is substituted or unsubstituted $C_4$-$C_7$ cycloalkylene. In some embodiments, $L^2$ is substituted or unsubstituted $C_5$-$C_8$ arylene. In some embodiments, $L^2$ is unsubstituted $C_4$-$C_7$ cycloalkylene. In some embodiments, $L^2$ is phenylene. In some embodiments, $L^2$ is methylene. In some embodiments, $L^2$ is unsubstituted $C_5$-$C_8$ arylene. In some embodiments, $L^2$ is phenylene. In some embodiments. $L^2$ is methylene. In some embodiments, $L^2$ is cyclohexyl.

In some embodiments of the compound of Formula (II), $L^1$ is substituted or unsubstituted $C_1$-$C_5$ alkylene, substituted or unsubstituted $C_2$-$C_5$ alkenylene, or substituted or unsubstituted $C_2$-$C_5$ alkynylene; and $L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene. In some embodiments, $L^1$ is $C_1$-$C_5$ alkylene, $C_1$-$C_3$ alkenylene, or $C_1$-$C_5$ alkynylene; and L is $C_1$-$C_5$ alkylene, $C_1$-$C_3$ alkenylene, or $C_1$-$C_5$ alkynylene. In some embodiments. $L^1$ is $C_1$-$C_5$ alkylene; and $L^3$ is $C_1$-$C_5$ alkylene.

In some embodiments of the compound of Formula (II), at least two of $L^1$, $L^2$ and $L^3$ are not a bond. In some embodiments, $L^1$ is bond. In some embodiments, L is bond.

In some embodiments of Formula (II), each $R^1$ is independently substituted or unsubstituted $C_1$-$C_6$ alkyl or substituted or unsubstituted $C_1$-$C_6$ heteroalkyl. In some embodiments, each $R^1$ is independently substituted or unsubstituted $C_1$-$C_6$ alkyl. In some embodiments, each $R^1$ is independently —CH$_3$, —CH$_2$CH$_3$, —CH$_2$CH$_2$CH$_3$, or —CH$_2$(CH$_3$)$_2$. In some embodiments, each $R^1$ is independently —CH$_3$, —CH$_2$CH$_2$CH$_3$, or —CH$_2$(CH$_3$)$_2$. In some embodiments, each $R^1$ is —CH$_3$.

In some embodiments of Formula (II), each $R^2$ is independently substituted or unsubstituted $C_1$-$C_6$ alkyl or substituted or unsubstituted $C_1$-$C_6$ heteroalkyl. In some embodiments, each $R^2$ is independently substituted or unsubstituted $C_1$-$C_6$ alkyl. In some embodiments, each $R^2$ is independently —CH$_3$, —CH$_2$CH$_3$, —CH$_2$CH$_2$CH$_3$, or —CH$_2$(CH$_3$)$_2$. In some embodiments, each $R^2$ is independently —CH$_3$, —CH$_2$CH$_2$CH$_3$, or —CH$_2$(CH$_3$)$_2$. In some embodiments, each $R^2$ is —CH$_2$(CH$_3$)$_2$.

In some embodiments of Formula (II), two $R^2$ are taken together with the nitrogen atom to which they are attached to form a substituted or unsubstituted $C_2$-$C_{10}$ heterocycloalkyl. In some embodiments of Formula (II), $R^3$ is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl. In some embodiments, $R^3$ is selected from unsubstituted or substituted monocyclic carbocycle, and unsubstituted or substituted monocyclic heterocycle. In some embodiments, $R^3$ is hydrogen.

In some embodiments of the oligonucleotide conjugate of Formula (I), B is a compound having the structure of Formula (II).

One embodiment provides an oligonucleotide conjugate of Formula (Xa):

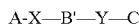 A-X—B'—Y—C    Formula (Xa);

wherein,
A is a binding moiety;
B' is a polynucleotide compound of Formula (II);
C is optionally a polymer;
X is a bond or a first linker; and
Y is a bond or a second linker;
wherein the polynucleotide further comprises one or more additional non-natural nucleotides; and
wherein A and C are not attached to B at the same terminus.

Another embodiment provides the oligonucleotide of Formula (I) or (Xa), wherein the polynucleotide further comprises, at least one modified internucleotide linkage, or at least one inverted abasic moiety.

Another embodiment provides the oligonucleotide of Formula (I) or (Xa), wherein the compound of Formula (IIa) is located at an internucleotide linkage of the polynucleotide.

Another embodiment provides the oligonucleotide of Formula (I) or (Xa), wherein the compound of Formula (IIa) is further modified at the 2'-position.

Another embodiment provides the oligonucleotide of Formula (I) or (Xa), wherein the one or more additional non-natural nucleotides comprises a 2"-modification selected from 2'-O-methyl, 2'-O-methoxyethyl (2-O-MOE), 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide.

Another embodiment provides the oligonucleotide of Formula (I) or (Xa), wherein the compound of Formula (IIa) is selected from locked nucleic acid (LNA) or ethylene nucleic acid (ENA)

Another embodiment provides the oligonucleotide of Formula (I) or (Xa), wherein the at least one inverted abasic moiety is at least one terminus.

Another embodiment provides the oligonucleotide of Formula (I) or (Xa), wherein the oligonucleotide is single stranded. Another embodiment provides the oligonucleotide of Formula (Xa), wherein the oligonucleotide is double stranded.

Another embodiment provides the oligonucleotide of Formula (I) or (Xa), wherein the oligonucleotide is from 2 to about 100 residues in length. Another embodiment provides the oligonucleotide of Formula (I) or (Xa), wherein the oligonucleotide is from 2 to about 90 residues in length. Another embodiment provides the oligonucleotide of Formula (I) or (Xa), wherein the oligonucleotide is from 2 to about 80 residues in length. Another embodiment provides the oligonucleotide of Formula (I) or (Xa), w % herein the oligonucleotide is from 2 to about 70 residues in length. Another embodiment provides the oligonucleotide of Formula (I) or (Xa), wherein the oligonucleotide is from 2 to about 60 residues in length. Another embodiment provides the oligonucleotide of Formula (I) or (Xa), wherein the oligonucleotide is from 2 to about 50 residues in length. Another embodiment provides the oligonucleotide of Formula (I) or (Xa), wherein the oligonucleotide is from 2 to about 40 residues in length. Another embodiment provides the oligonucleotide of Formula (I) or (Xa), wherein the oligonucleotide is from 2 to about 30 residues in length. Another embodiment provides the oligonucleotide of Formula (I) or (Xa), wherein the oligonucleotide is from 2 to about 20 residues in length. Another embodiment provides the oligonucleotide of Formula (I) or (Xa), wherein the oligonucleotide is from 2 to about 10 residues in length. Another embodiment provides the oligonucleotide of Formula (I) or (Xa), wherein the oligonucleotide is from 8 to about 30 residues in length. Another embodiment provides the oligonucleotide of Formula (Xa), wherein the oligonucleotide is from 10 to about 30 residues in length. Another embodiment provides the oligonucleotide of Formula (I) or (Xa), wherein the oligonucleotide is from 14 to about 30 residues in length. Another embodiment provides the oligonucleotide of Formula (Xa), wherein the oligonucleotide is from 18 to about 30) residues in length. Another embodiment provides the oligonucleotide of Formula (I) or (Xa), wherein the oligonucleotide is from 22 to about 30 residues in length. Another embodiment provides the oligonucleotide of Formula (I) or (X), wherein the oligonucleotide is from 26 to about 30 residues in length.

One embodiment provides a compound suitable for the synthesis of oligonucleotides selected from the group:

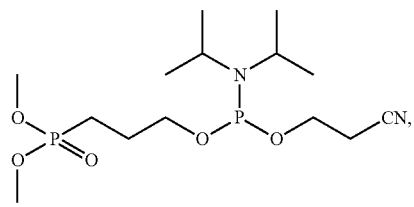

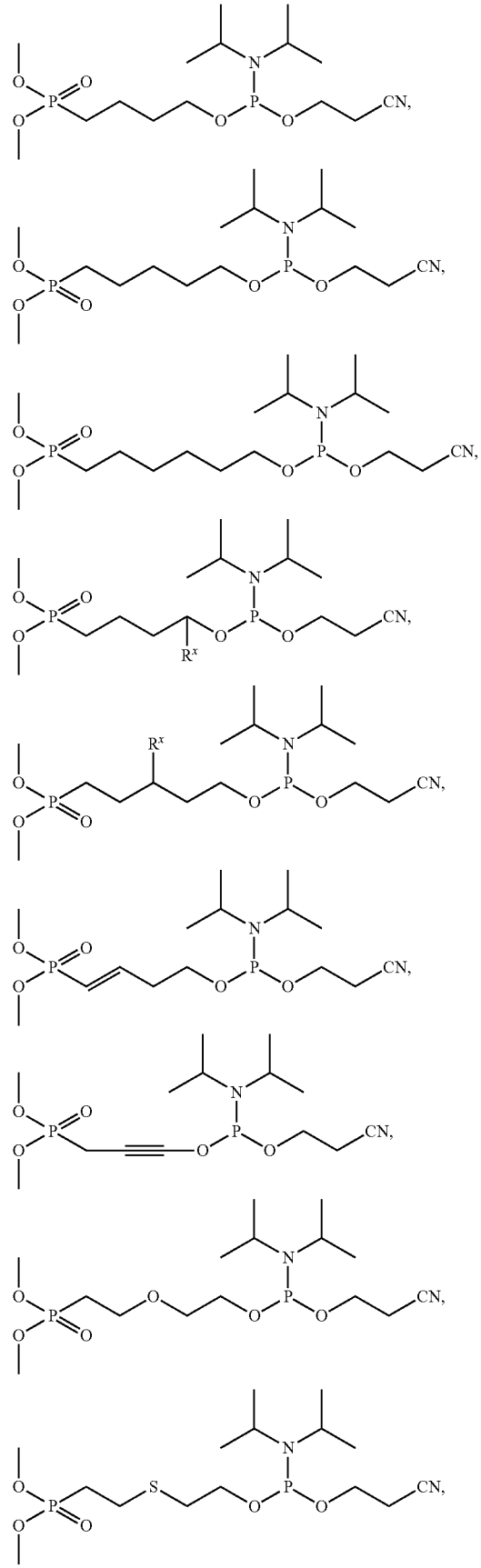

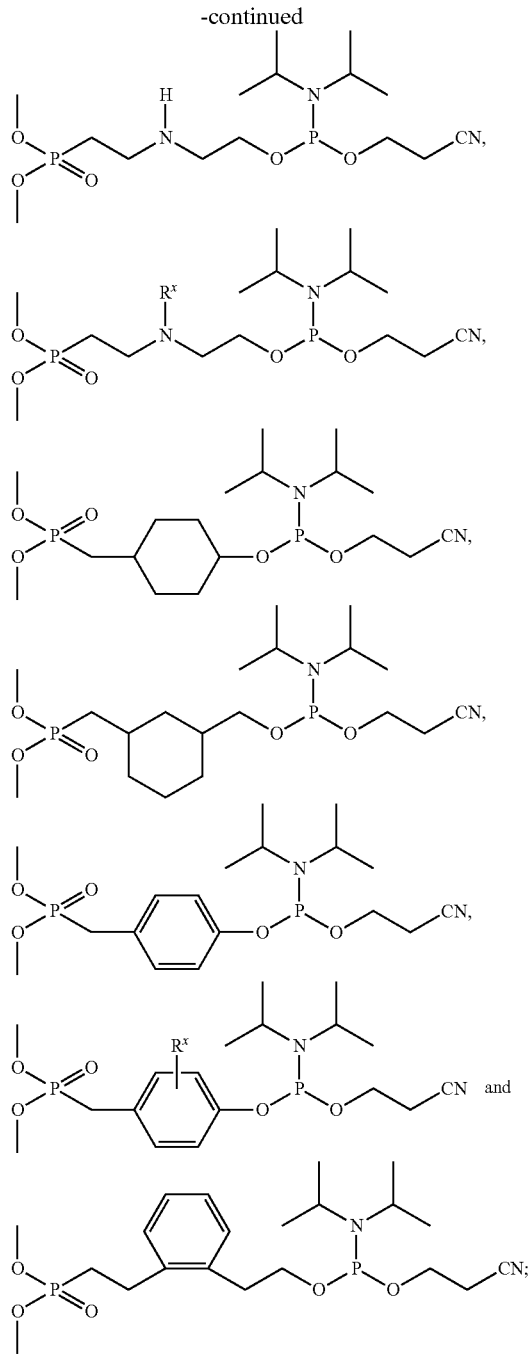

wherein $R^x$ is H, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —O—alkyl, —CO$_2$H, —CO$_2$-alkyl, —CH$_2$CO$_2$H, —CH$_2$CO$_2$-alkyl, —C(=O)NH$_2$, —C(=O)NH-alkyl, —CH$_2$C(=O)NH$_2$, —CH$_2$C(=O)NH-alkyl, NH$_2$, —NH-alkyl. —CH$_2$NH$_2$, —CH$_2$NH-alkyl, —NHC(=O)alkyl, —CH$_2$NHC(=O)alkyl, —SH, —S-alkyl, —S(=O)H, —S(=O)alkyl, —SO$_2$H, —SO$_2$-alkyl, —SO$_2$NH$_2$ or —SO$_2$NH-alkyl.

Conjugation Chemistry

In some embodiments, a polynucleic acid molecule is conjugated to a binding moiety. In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives,". *J. Am. Chem. Soc.* 1997, 119, 4325-4329; Hackeng, et al. "Protein synthesis by native chemical ligation: Expanded scope by using straightforward methodology," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi el al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivative conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106(9): 3000-3005 (2009);

Agarwal, et al., "A Pictet-Spengler ligation for protein chemical modification," *PNAS* 110(1): 46-51 (2013)).

In some instances, the enzyme-catalyzed process comprises microbial transglutaminase (mTG). In some cases, the polynucleic acid molecule is conjugated to the binding moiety utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013)).

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Binding Moiety

In some embodiments, the binding moiety A is a polypeptide. In some instances, the polypeptide is an antibody or its fragment thereof. In some cases, the fragment is a binding fragment. In some instances, the antibody or binding fragment thereof comprises a humanized antibody or binding fragment thereof, human antibody or binding fragment thereof, anti-murine antibody (e.g., anti-mouse antibody, anti-rat antibody, etc.), anti-human antibody (e.g., anti-human transferrin receptor antibody), murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances. A is an antibody or binding fragment thereof. In some instances, A is a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, disulfide stabilized Fv protein ("dsFv"), single-domain antibody (sdAb), Ig NAR, camelid antibody or binding fragment thereof, bispecific antibody or biding fragment thereof, or a chemically modified derivative thereof. In some instances, A is a humanized antibody or binding fragment thereof. In some instances, A is a murine antibody or binding fragment thereof. In some instances, A is a chimeric antibody or binding fragment thereof. In some instances, A is a monoclonal antibody or binding fragment thereof. In some instances, A is a full size antibody. In some instances, A is a monovalent Fab'. In some instances, A is a divalent $Fab_2$. In some instances, A is a single-chain variable fragment (scFv).

In some embodiments, the binding moiety A is a bispecific antibody or binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens. Exemplary trifunctional antibodies include catumaxomab (which targets EpCAM and CD3; Fresenius Biotech/Trion Pharma), ertumaxomab (targets HER2/neu/CD3; Fresenius Biotech-Trion Pharma), lymphomun FBTA05 (targets CD20/CD3; Fresenius Biotech/Trion Pharma), RG7221 (RO5520985; targets Angiopoietin 2/VEGF; Roche), RG7597 (targets Her1/Her3; Genentech/Roche). MM141 (targets IGF1R/Her3; Merrimack), ABT122 (targets TNFα/IL17; Abbvie), ABT981 (targets IL1α/IL1β; Abbott), LY3164530 (targets Her1/cMET; Eli Lilly), and TRBS07 (Ektomab; targets GD2/CD3; Trion Research Gmbh). Additional exemplary trifunctional antibodies include $mAb^2$ from F-star Biotechnology Ltd. In some instances, A is a bispecific trifunctional antibody. In some embodiments, A is a bispecific trifunctional antibody selected from: catumaxomab (which targets EpCAM and CD3; Fresenius Biotech/Trion Pharma), ertumaxomab (targets HER2/neu/CD3; Fresenius Biotech/Trion Pharma), lymphomun FBTA05 (targets CD20/CD3; Fresenius Biotech/Trion Pharma), RG7221 (RO5520985; targets Angiopoietin 2/VEGF; Roche), RG7597 (targets Her1/Her3; Genentech/Roche), MM141 (targets IGF1R/Her3; Merrimack), ABT122 (targets TNFα/IL17; Abbvie), ABT981 (targets IL1α/IL1β; Abbott), LY3164530 (targets Her1/cMET; Eli Lilly), TRBS07 (Ektomab; targets GD2/CD3; Trion Research Gmbh), and a $mAb^2$ from F-star Biotechnology Ltd.

In some cases, the bispecific antibody is a bispecific mini-antibody. In some instances, the bispecific mini-antibody comprises divalent $Fab_2$, F(ab)'$_3$ fragments, bis-scFv, $(scFv)_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens. Exemplary bispecific mini-antibodies include, but are not limited to, DART (dual-affinity re-targeting platform; MacroGenics), blinatumomab (MT103 or AMG103; which targets CD19/CD3; Micromet), MT111 (targets CEA/CD3; Micromet/Amegen), MT112 (BAY2010112; targets PSMA/CD3; Micromet/Bayer), MT110 (AMG 110; targets EPCAM/CD3; Amgen/Micromet), MGD006 (targets CD123/CD3; MacroGenics), MGD007 (targets GPA33/CD3; MacroGenics). BI1034020 (targets two different epitopes on β-amyloid; Ablynx), ALX0761 (targets IL17A/IL17F; Ablynx), TF2 (targets CEA/hepten; Immunomedics), IL-17/IL-34 biAb (BMS), AFM13 (targets CD30/CD16; Affimed). AFM11 (targets CD19/CD3; Affimed), and domain antibodies (dAbs from Domantis/GSK).

In some embodiments, the binding moiety A is a bispecific mini-antibody. In some instances, A is a bispecific $Fab_2$. In some instances, A is a bispecific F(ab)'$_3$ fragment. In some cases, A is a bispecific bis-scFv. In some cases, A is a bispecific $(scFv)_2$. In some embodiments, A is a bispecific diabody. In some embodiments, A is a bispecific minibody. In some embodiments, A is a bispecific triabody. In other embodiments, A is a bispecific tetrabody. In other embodiments, A is a bi-specific T-cell engager (BiTE). In additional embodiments, A is a bispecific mini-antibody selected from: DART (dual-affinity re-targeting platform; MacroGenics), blinatumomab (MT103 or AMG103; which targets CD19/CD3; Micromet), MT111 (targets CEA/CD3; Micromet/Amegen), MT112 (BAY2010112; targets PSMA/CD3; Micromet/Bayer), MT110 (AMG 110; targets EPCAM/CD3; Amgen/Micromet), MGD006 (targets CD123/CD3; MacroGenics), MGD007 (targets GPA33/CD3; MacroGenics), B11034020 (targets two different epitopes on β-amyloid; Ablynx), ALX0761 (targets IL17A/IL17F; Ablynx), TF2 (targets CEA/hepten; Immunomedics), IL-17/IL-34 biAb (BMS), AFM13 (targets CD30/CD16; Affimed), AFM11 (targets CD19/CD3; Affimed), and domain antibodies (dAbs from Domantis/GSK).

In some embodiments, the binding moiety A is a trispecific antibody. In some instances, the trispecific antibody comprises F(ab)'$_3$ fragments or a triabody. In some instances, A is a trispecific F(ab)'$_3$ fragment. In some cases, A is a triabody. In some embodiments, A is a trispecific antibody as described in Dimas, et al., "Development of a trispecific antibody designed to simultaneously and efficiently target three different antigens on tumor cells." *Mol. Pharmaceutics*, 12(9): 3490-3501 (2015).

In some embodiments, the binding moiety A is an antibody or binding fragment thereof that recognizes a cell surface protein. In some instances, the cell surface protein is an antigen expressed by a cancerous cell. Exemplary cancer antigens include, but are not limited to, alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAP1B, SPAP1C), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Rα, Immunoglobulin superfamily receptor translocation associated 2 (IRTA2), L6, Lewis Y, Lewis X, MAGE-1, MAGE-2, MAGE-3, MAGE 4, MART1, mesothelin, MDP, MPF (SMR, MSLN), MCP1 (CCL2), macrophage inhibitory factor (MIF), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b), transferrin receptor, tumor-associated glycoprotein 72 (TAG-72), TrpM4 (BR22450, FLJ20041, TRPM4, TRPM4B, transient receptor potential cation channel, subfamily M, member 4) and the like. In some instances, the binding moiety is an α-transferrin receptor antibody or binding fragments thereof. In some instances, the binding moiety is an α-human transferrin receptor antibody. In some instances, the binding moiety is an α-human transferrin receptor antibody as described in PCT/US2019/068078, which is incorporated by reference herein.

In some instances, the cell surface protein comprises clusters of differentiation (CD) cell surface markers. Exemplary CD cell surface markers include, but are not limited to, CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD71, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), and the like.

In some instances, the binding moiety A is an antibody or binding fragment thereof that recognizes a cancer antigen. In some instances, the binding moiety A is an antibody or binding fragment thereof that recognizes alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAP1B, SPAP1C), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Ra, Immunoglobulin superfamily receptor translocation associated 2 (IRTA2), L6, Lewis Y, Lewis X, MAGE-1, MAGE-2, MAGE-3, MAGE 4, MART1, mesothelin, MCP1 (CCL2), MDP, macrophage inhibitory factor (MIF), MPF (SMR, MSLN), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b, tumor-associated glycoprotein 72 (TAG-72), TrpM4 (BR22450, FLJ20041, TRPM4, TRPM4B, transient receptor potential cation channel, subfamily M, member 4) or a combination thereof.

In some instances, the binding moiety A is an antibody or binding fragment thereof that recognizes a CD cell surface marker. In some instances, the binding moiety A is an antibody or binding fragment thereof that recognizes CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD71, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), or a combination thereof.

In some embodiments, the antibody or binding fragment thereof comprises zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (hu1D10), ascrinvacumab (Pfizer Inc.), atezolizumab (MPDL3280A, Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C6; Seattle Genetics, Inc.), daratumumab (Darzalex®, Janssen Biotech), detumomab, drozitumab (Genentech), durvalumab (MedImmune), dusigitumab (MedImmune), edrecolomab (MAb17-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin, MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362 (Claudiximab, Ganymed Pharmaceuticals AG), imalumab (Baxalta), IMC-1C11 (ImClone Systems), IMC-C225 (Imclone Systems Inc.), imgatuzumab (Genentech/Roche), inetumumab (Centocor, Inc.), ipilimumab (Yervoy®, Bristol-Myers Squibb), iratumumab (Medarex, Inc.), isatuximab (SAR650984, Sanofi-Aventis), labetuzumab (CEA-CIDE, Immunomedics), lexatumumab (ETR2-STOI, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics. Inc.), mitumomab (BEC-2. ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (OpdivoX, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF, Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart MI95 (Protein Design Labs, Inc.), Smart ID10 (Protein Design Labs, Inc.), tabalumab (LY2127399, Eli Lilly), taplitumomab paptox, tenatumomab, teprotumumab (Roche), tetulomab, TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), zatuximab, and the like.

In some embodiments, the binding moiety A comprises zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (huID10), ascrinvacumab (Pfizer Inc.), atezolizumab (MPDL3280A; Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C6; Seattle Genetics, Inc.), daratumumab (Darzalex®, Janssen Biotech), detumomab, drozitumab (Genentech), durvalumab (MedImmune), dusigitumab (MedImmune), edrecolomab (MAb17-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin. MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362 (Claudiximab, Ganymed Pharmaceuticals AG), imalumab (Baxalta), IMC-1C11 (ImClone Systems), IMC-C225 (Imclone Systems Inc.), imgatuzumab (Genentech/Roche), inetumumab (Centocor. Inc.), ipilimumab (Yervoyl®, Bristol-Myers Squibb), iratumumab (Medarex, Inc.), isatuximab (SAR650984, Sanofi-Aventis), labetuzumab (CEA-CIDE, Immunomedics), lexatumumab (ETR2-ST01, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics, Inc.), mitumomab (BEC-2, ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (Opdivot, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF. Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart M195 (Protein Design Labs, Inc.), Smart ID10 (Protein Design Labs. Inc.), tabalumab (LY2127399, Eli Lilly), taplitumomab paptox, tenatumomab, teprotumumab (Roche), tetulomab. TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), or zatuximab. In some embodiments, the binding moiety A is zalutumumab (HuMax-EFGr, by Genmab).

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to poly nucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell (e.g., a cancerous cell) that expresses PSMA. In some instances, a binding moiety is a small molecule described in Zhang et al., "A remote arene-binding site on prostate specific membrane antigen revealed by antibody-recruiting small molecules," J Am Chem Soc. 132(36): 12711-12716 (2010); or McEnaney, et al., "Antibody-recruiting molecules: an emerging paradigm for engaging immune function in treating human disease," ACS Chem Biol. 7(7): 1139-1151 (2012).

Polynucleic Acid Molecule Targets

In some embodiments, the polynucleic acid molecule B is a polynucleic acid molecule (or polynucleotide) that hybridizes to a target region on an oncogene. In some instances, oncogenes are further classified into several categories: growth factors or mitogens, receptor tyrosine kinases, cytoplasmic tyrosine kinases, cytoplasmic serine/threonine kinases, regulatory GTPases, and transcription factors. Exemplary growth factors include c-Sis. Exemplary receptor tyrosine kinases include epidermal growth factor receptor (EGFR), platelet-derived growth factor receptor (PDGFR), vascular endothelial growth factor receptor (VEGFR), and HER2/neu. Exemplary cytoplasmic tyrosine kinases include Src-family tyrosine kinases, Syk-ZAP-70 family of tyrosine kinases, BTK family of tyrosine kinases, and Abl gene in CML. Exemplary cytoplasmic serine/threonine kinases include Raf kinase and cyclin-dependent kinases. Exemplary regulatory GTPases include Ras family of proteins such as KRAS. Exemplary transcription factors include MYC gene. In some instances, an oncogene described herein comprises an oncogene selected from growth factors or mitogens, receptor tyrosine kinases, cytoplasmic tyrosine kinases, cytoplasmic serine/threonine kinases, regulatory GTPases, or transcription factors. In some embodiments, the pol ynucleic acid molecule is a polynucleic acid molecule that hybridizes to a target region of an oncogene selected from growth factors or mitogens, receptor tyrosine kinases, cytoplasmic tyrosine kinases, cytoplasmic serine/threonine kinases, regulatory GTPases, or transcription factors.

In some embodiments, an oncogene described herein comprises Ab, AKT-2, ALK, AML1 (or RUNX1), AR, AXL, BCL-2, 3, 6, BRAF, c-MYC, EGFR, ErbB-2 (Her2, Neu), Fms, FOS, GLI1, HPR1, IL-3, INTS2, JUN, KIT, KS3, K-sam, LBC (AKAP13), LCK, LMO1, LMO2, LYL1, MAS1, MDM2, MET, MLL (KMT2A), MOS, MYB, MYH11/CBFB, NOTCH1 (TAN1), NTRK1 (TRK), OST (SLC51B), PAX5, PIM1, PR4D-1, RAF, RAR/PML, HRAS, KRAS, NRAS, REL/NRG, RET, ROS, SKI, SRC, TIAM1, or TSC2. In some embodiments, the polynucleic acid molecule is a polynucleic acid molecule that hybridizes to a target region of Ab1, AKT-2, ALK, AML1 (or RUNX1), AR, AXL, BCL-2, 3, 6, BRAF, c-MYC, EGFR, ErbB-2 (Her2, Neu), Fms, FOS, GLI1, HPRT1, IL-3, INTS2, JUN, KIT, KS3, K-sam, LBC (AKAP13), LCK, LMO1, LMO2, LYL1, MAS1, MDM2, MET, MLL (KMT2A), MOS, MYB, MYH11/CBFB, NOTCH1 (TAN1), N7RK1 (TRK), OST (SLC51B), PAX5, PIM1, PRAD-1, RAF, RAR/PML, HRAS, KRAS, NRAS, REL/NRG, RET ROS, SKI, SRC, TIAM1, or TSC2.

In some embodiments, an oncogene described herein comprises KRAS, EGFR, AR, HPRT1, CNNTB1 (β-catenin), or β-catenin associated genes. In some embodiments, the polynucleic acid molecule B is a polynucleic acid molecule that hybridizes to a target region of KRAS, EGFR, AR, HPRT1, CNNTB1 (β-catenin), or β-catenin associated genes. In some embodiments, the polynucleic acid molecule B is a polynucleic acid molecule that hybridizes to a target region of KRAS. In some embodiments, the polynucleic acid molecule B is a polynucleic acid molecule that hybridizes to a target region of EGFR. In some embodiments, the polynucleic acid molecule B is a polynucleic acid molecule that hybridizes to a target region of AR. In some embodiments, the polynucleic acid molecule B is a polynucleic acid molecule that hybridizes to a target region of CNNTB1 (β-catenin). In some embodiments, the polynucleic acid molecule B is a polynucleic acid molecule that hybridizes to a target region of CNNTB1 (β-catenin) associated genes. In some instances, the β-catenin associated genes comprise PIK3CA, PIK3CB, and Myc. In some instances, the polynucleic acid molecule B is a polynucleic acid molecule that hybridizes to a target region of HPRT1.

Polynucleic Acid Molecules That Target Kirsten Rat Sarcoma Viral Oncogene Homolog (KRAS)

Kirsten Rat Sarcoma Viral Oncogene Homolog (also known as GTPase KRas, V-Ki-ras2 Kirsten rat sarcoma viral oncogene homolog, or KRAS) is involved in regulating cell division. The K-Ras protein is a GTPase belonging to the Ras superfamily. In some instances, K-Ras modulates cell cycle progression, as well as induces growth arrest, apoptosis, and replicative senescence under different environmental triggers (e.g., cellular stress, ultraviolet, heat shock, or ionizing irradiation). In some cases, wild type KRAS gene has been shown to be frequently lost during tumor progression in different types of cancer, while mutations of KRAS gene have been linked to cancer development. In some instances, KRAS amplification has also been implicated in cancer development (see, for example, Valtorta et al. "KRAS gene amplification in colorectal cancer and impact on response to EGFR-targeted therapy." *Int. J. Cancer* 133: 1259-1266 (2013)). In such cases, the cancer pertains to a refractory cancer in which the patient has acquired resistance to a particular inhibitor or class of inhibitors.

In some embodiments, the KRAS gene is wild type or comprises a mutation. In some instances, KRAS mRNA is wild type or comprises a mutation. In some instances, the polynucleic acid molecule is a polynucleic acid molecule that hybridizes to a target region of wild type KRAS DNA or RNA In some instances, the polynucleic acid molecule is a polynucleic acid molecule that hybridizes to a target region of KRAS DNA or RNA comprising a mutation (e.g., a substitution, a deletion, or an addition).

In some embodiments, KRAS DNA or RNA comprises one or more mutations. In some embodiments, KRAS DNA or RNA comprises one or more mutations at codons 12 or 13 in exon 1. In some instances, KRAS DNA or RNA comprises one or more mutations at codons 61, 63, 117, 119, or 146. In some instances, KRAS DNA or RNA comprises one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, KRAS DNA or RNA comprises one or more mutations at positions corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61 L, Q61R, E63K, Y64D, Y64N, R68S, P110S, K117N, C118S, A146T, A146P, A146V, K147N, T158A, R164Q, K176Q, or a combination thereof of the KRAS polypeptide.

In some embodiments, the polynucleic acid molecule hybridizes to a target region of KRAS DNA or RNA comprising one or more mutations. In some embodiments, the polynucleic acid molecule hybridizes to a target region of KRAS DNA or RNA comprising one or more mutations at codons 12 or 13 in exon 1. In some embodiments, the polynucleic acid molecule hybridizes to a target region of KRAS DNA or RNA comprising one or more mutations at codons 61, 63, 117, 119, or 146. In some embodiments, the polynucleic acid molecule hybridizes to a target region of KRAS DNA or RNA comprising one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, the polynucleic acid molecule hybridizes to a target region of KRAS DNA or RNA comprising one or more mutations corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61L, Q61R, E63K, Y64D, Y64N, R68S, P110S, K117N, C118S, A146T, A146P, A146V, K147N, T158A, R164Q, K176Q, or a combination thereof of the KRAS polypeptide.

In some embodiments, the binding moiety A is conjugated according to Formula (I) to a polynucleic acid molecule (B), and optionally a polymer (C), described herein. In some instances, the polymer C comprises polyalkylene oxide (e.g., polyethylene glycol).

In some embodiments, the binding moiety A is conjugated to a polynucleic acid molecule (B), and optionally a polymer (C). In some instances, the binding moiety A is an antibody or binding fragment thereof.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue in a non-site specific manner. In some cases, the binding moiety A is conjugated to a polynucleic acid molecule (B) via a cysteine residue in a non-site specific manner. In some instances, the binding moiety A is an antibody or binding fragment thereof.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue via a site-specific manner. In some instances, the binding moiety A is conjugated to a polynucleic acid molecule (B) through a cysteine residue via a site-specific manner. In some instances, the binding moiety A is conjugated to a polynucleic acid molecule (B) at the 5-terminus via a site-specific manner. In some instances, the binding moiety A is conjugated to a pol ynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner. In some instances, the binding moiety A is an antibody or binding fragment thereof.

In some embodiments, one or more regions of a binding moiety A (e.g., an antibody or binding fragment thereof) is conjugated to a polynucleic acid molecule (B). In some instances, the one or more regions of a binding moiety A comprise the N-terminus, the C-terminus, in the constant region, at the hinge region, or the Fc region of the binding moiety A. In some instances, the polynucleic acid molecule (B) is conjugated to the N-terminus of the binding moiety A (e.g., the N-terminus of an antibody or binding fragment thereof). In some instances, the polynucleic acid molecule (B) is conjugated to the C-terminus of the binding moiety A (e.g., the N-terminus of an antibody or binding fragment thereof). In some instances, the polynucleic acid molecule (B) is conjugated to the constant region of the binding moiety A (e.g., the constant region of an antibody or binding fragment thereof). In some instances, the pol ynucleic acid molecule (B) is conjugated to the hinge region of the binding moiety A (e.g., the constant region of an antibody or binding fragment thereof). In some instances, the polynucleic acid molecule (B) is conjugated to the Fc region of the binding moiety A (e.g., the constant region of an antibody or binding fragment thereof).

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 pol ynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different. In some instances, the binding moiety A is an antibody or binding fragment thereof.

In some embodiments, the number of polynucleic acid molecule (B) conjugated to a binding moiety A (e.g., an antibody or binding fragment thereof) forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A (e.g., an antibody or binding fragment thereof) is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some embodiments, an antibody or its binding fragment is further modified using conventional techniques known in the art, for example, by using amino acid deletion, insertion, substitution, addition, and/or by recombination and/or any other modification (e.g. posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or its binding fragment or a reduced off-target effect. For example, the antibody or its binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994. *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy, Alan R. Liss, Inc. pp.* 77-96). Alternatively, a clone encoding at least the Fab portion of the antibody is optionally obtained by screening Fab expression libraries (e.g., as described in Huse et al., 1989. *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985. *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989. *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984. *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule. In some cases, a polymer moiety C is conjugated to a binding moiety. In other cases, a polymer moiety C is conjugated to a polynucleic acid molecule-binding moiety molecule. In additional cases, a polymer moiety C is conjugated, and as discussed under the Therapeutic Molecule Platform section.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylene oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50.000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 800, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100.000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, the polymer moiety C comprises a cationic mucic acid-based polymer (cMAP). In some instances, cMPA comprises one or more subunit of at least one repeating subunit, and the subunit structure is represented as Formula (III):

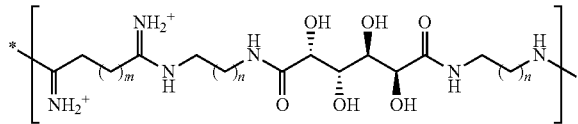

Formula III wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

Endosomolytic or Cell Membrane Penetration Moiety

In some embodiments, a molecule of Formula (Xa): A-X$_1$—B'—X$_2$—C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some embodiments, a molecule of Formula (Xa): A-X$_1$—B—X$_2$—C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof. In some instances, the endosomolytic polypeptide comprises Pep-1 (originated from NLS from Simian Virus 40 large antigen and reverse transcriptase of HIV), Pvec (originated from VE-Cadherin), VT5 (originated from synthetic peptide), C105Y (originated from 1-antitrypsin), transportan (originated from Galanin and mastoparan), TP10 (originated from Galanin and mastoparan), MPG (originated from a hydrophobic domain from the fusion sequence of HIV gp41 and NLS of SV40 T antigen), GH625 (originated from glycoprotein gH of HSV type I), CADY (PPTG1 peptide), GALA (synthetic peptide), INF (Influenza HA2 fusion peptide), HA2E5-TAT (Influenza HA2 subunit of influenza virus X31 strain fusion peptide), HA2-penetratin (Influenza HA2 subunit of influenza virus X31 strain fusion peptide), HA-K4 (Influenza HA2 subunit of influenza virus X31 strain fusion peptide), HA2E4 (Influenza HA2 subunit of influenza virus X31 strain fusion peptide), H5WYG (HA2 analogue), GALA-INF3-(PEG)6-NH (INF3 fusion peptide), or CM18-TAT11 (Cecropin-A-Melittin$_{2-12}$ (CM$_{18}$) fusion peptide).

In some cases, the endosomolytic moiety comprises a Bak BH3 polypeptide which induces apoptosis through antagonization of suppressor targets such as Bcl-2 and/or Bcl-x$_L$. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71: 261-265 (2011).

In some instances, the endosomolytic moiety comprises a pol ypeptide (e.g., a cell-penetrating polypeptide) as described in PCT Publication Nos. WO2013/166155 or WO2015/069587.

Endosomolytic Lipids

In some embodiments, the endosomolytic moiety is a lipid (e.g., a fusogenic lipid). In some embodiments, a molecule of Formula (Xa): A-X$_1$—B'— X$_2$—C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z, 9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC). In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (Xa): $A-X_1—B'—X_2—C$, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethyl-amino-1-butylamino) quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(l-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino) quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxy-ethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Cell Penetrating Polypeptide (CPP)

In some embodiments, cell penetrating polypeptide comprises positively charged short peptides with 5-30 amino acids. In some embodiments, cell penetrating polypeptide comprises arginine or lysine rich amino acid sequences. In some embodiments, cell penetrating polypeptide includes any polypeptide or combination thereof, including Antennapedia Penetratin (43-58), HIV-1 TAT protein (48-60), pVEC Cadherin (615-632), Transportan Galanine/Mastoparan, MPG HIV-gp41/SV40 T-antigen. Pep-1 HIV-reverse transcriptase/SV40 T-antigen, Polyarginines, MAP, R6W3, NLS, 8-lysines, ARF (1-22), and Azurin-p28.

Linkers

In some embodiments, a linker described herein is a cleavable linker or a non-cleavable linker. In some instances, the linker is a cleavable linker. In some instances, the linker is an acid cleavable linker. In some instances, the linker is a non-cleavable linker. In some instances, the linker includes a $C_1$-$C_6$ alkyl group (e.g., a $C_5$, $C_4$, $C_3$, $C_2$, or $C_1$ alkyl group). In some instances, the linker includes homobifunctional cross linkers, heterobifunctional cross linkers, and the like. In some instances, the liker is a traceless linker (or a zero-length linker). In some instances, the linker is a non-polymeric linker. In some cases, the linker is a non-peptide linker or a linker that does not contain an amino acid residue.

In some instances, the linker comprises a homobifunctional linker. Exemplary homobifunctional linkers include, but are not limited to. Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyl-dithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(T-maleimidobutyryloxy)sulfosuccinimide ester (sulfo-GMBs), succinimidyl 6-((iodoacetyl)amino)hexanoate (sAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido) butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, 6, 7, 8, or more amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 14223), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 14224), or Gly-Phe-Leu-Gly (SEQ ID NO: 14225). In some instances, the linker comprises a peptide moiety such as: Val-Cit (valine-citrulline). Gly-Gly-Phe-Gly (SEQ ID NO: 14223). Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 14224), or Gly-Phe-Leu-Gly (SEQ ID NO: 14225). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker comprises a functional group that exerts steric hinderance at the site of bonding between the linker and a conjugating moiety (e.g., A, B, C, or D described herein). In some instances, the steric hinderance is a steric hindrance around a disulfide bond. Exemplary linkers that exhibit steric hinderance comprises a heterobifunctional linker, such as a heterobifunctional linker described above. In some cases, a linker that exhibits steric hinderance comprises SMCC and SPDB.

In some instances, the linker is an acid cleavable linker. In some instances, the acid cleavable linker comprises a hydrazone linkage, which is susceptible to hydrolytic cleavage. In some cases, the acid cleavable linker comprises a thiomaleiamic acid linker. In some cases, the acid cleavable linker is a thiomaleamic acid linker as described in Castaneda, et al, "Acid-cleavable thiomaleamic acid linker for homogeneous antibody-drug conjugation," *Chem. Commun.* 49: 8187-8189 (2013).

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some embodiments, X, Y, and L are independently a bond or a linker. In some instances, X, Y, and L are independently a bond. In some cases, X, Y, and L are independently a linker.

In some instances, X is a bond or a linker. In some instances, X is a bond. In some instances. X is a linker. In some instances, the linker is a $C_1$-$C_6$ alkyl group. In some cases, X is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of X, alkyl means a saturated straight or branched hydrocarbon radical containing up to six carbon atoms. In some instances, X is a non-polymeric linker. In some instances, X includes a homobifunctional linker or a heterobifunctional linker described supra. In some cases, X includes a heterobifunctional linker. In some cases, X includes sMCC. In other instances, X includes a heterobifunctional linker optionally conjugated to a $C_1$-$C_6$ alkyl group. In other instances, X includes sMCC optionally conjugated to a $C_1$-$C_6$ alkyl group. In additional instances, X does not include a homobifunctional linker or a heterobifunctional linker described supra.

In some instances, Y is a bond or a linker. In some instances, Y is a bond. In other cases, Y is a linker. In some embodiments, Y is a $C_1$-$C_6$ alkyl group. In some instances. Y is a homobifunctional linker or a heterobifunctional linker described supra. In some instances, Y is a homobifunctional linker described supra. In some instances, Y is a heterobifunctional linker described supra. In some instances, Y comprises a maleimide group, such as maleimidocaproyl (mc) or a self-stabilizing maleimide group described above. In some instances, Y comprises a peptide moiety, such as Val-Cit. In some instances, Y comprises a benzoic acid group, such as PABA. In additional instances, Y comprises a combination of a maleimide group, a peptide moiety, and/or a benzoic acid group. In additional instances, Y comprises a mc group. In additional instances, Y comprises a mc-val-cit group. In additional instances, Y comprises a val-cit-PABA group. In additional instances, Y comprises a mc-val-cit-PABA group.

In some instances, L is a bond or a linker. In some cases, L is a bond. In other cases, L is a linker. In some embodiments, L is a $C_1$-$C_6$ alkyl group. In some instances, L is a homobifunctional linker or a heterobifunctional linker described supra. In some instances, L is a homobifunctional linker described supra. In some instances, L is a heterobifunctional linker described supra. In some instances, L comprises a maleimide group, such as maleimidocaproyl (mc) or a self-stabilizing maleimide group described above. In some instances, L comprises a peptide moiety, such as Val-Cit. In some instances, L comprises a benzoic acid group, such as PABA. In additional instances, L comprises a combination of a maleimide group, a peptide moiety, and/or a benzoic acid group. In additional instances, L comprises a mc group. In additional instances, L comprises a mc-val-cit group. In additional instances, L comprises a val-cit-PABA group. In additional instances, L comprises a mc-val-cit-PABA group.

Methods of Use

In some embodiments, a composition or a pharmaceutical formulation described herein comprising a binding moiety conjugated to a polynucleic acid molecule and a polymer is used for the treatment of a disease or disorder. In some instances, the disease or disorder is a muscle dystrophy, muscle atrophy, and/or muscle wasting. Muscle dystrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis). In some instances, the disease or disorder is a cancer. In some embodiments, a composition or a pharmaceutical formulation described herein is used as an immunotherapy for the treatment of a disease or disorder. In some instances, the immunotherapy is an immuno-oncology therapy.

Cancer

In some embodiments, a composition or a pharmaceutical formulation described herein is used for the treatment of cancer. In some instances, the cancer is a solid tumor. In some instances, the cancer is a hematologic malignancy. In some instances, the cancer is a relapsed or refractory cancer, or a metastatic cancer. In some instances, the solid tumor is a relapsed or refractory solid tumor, or a metastatic solid tumor. In some cases, the hematologic malignancy is a relapsed or refractory hematologic malignancy, or a metastatic hematologic malignancy.

In some instances, a composition or a pharmaceutical formulation described herein comprising an oligonucleotide, optionally conjugated to a binding moiety, a polymer, or a combination thereof is used for the treatment of a solid tumor. In some instances, a composition or a pharmaceutical formulation described herein comprising an oligonucleotide, optionally conjugated to a binding moiety, a polymer, or a combination thereof is used for the treatment of anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer. In some instances, the solid tumor is a relapsed or refractory solid tumor, or a metastatic solid tumor.

In some instances, the cancer is a hematologic malignancy. In some instances, a composition or a pharmaceutical formulation described herein comprising an oligonucleotide, optionally conjugated to a binding moiety, a polymer, or a combination thereof is used for the treatment of a hematologic malignancy. In some instances, a composition or a pharmaceutical formulation described herein comprising an oligonucleotide, optionally conjugated to a binding moiety, a polymer, or a combination thereof is used for the treatment of a leukemia, a lymphoma, a myeloma, a non-Hodgkin's lymphoma, or a Hodgkin's lymphoma. In some instances, the hematologic malignancy comprises chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic malignancy is a relapsed or refractory hematologic malignancy, or a metastatic hematologic malignancy.

In some instances, the cancer is a KRAS-associated, EGFR-associated, AR-associated cancer, HPRT1-associated cancer, or β-catenin associated cancer. In some instances, a composition or a pharmaceutical formulation described herein comprising an oligonucleotide, optionally conjugated to a binding moiety, a polymer, or a combination thereof is used for the treatment of a KRAS-associated, EGFR-associated. AR-associated cancer, HPRT1-associated cancer, or β-catenin associated cancer. In some instances, a composition or a pharmaceutical formulation described herein comprising an oligonucleotide, optionally conjugated to a binding moiety, a polymer, or a combination thereof is used for the treatment of a KRAS-associated cancer. In some instances, a composition or a pharmaceutical formulation described herein comprising an oligonucleotide, optionally conjugated to a binding moiety, a polymer, or a combination thereof is used for the treatment of an EGFR-associated cancer. In some instances, a composition or a pharmaceutical formulation described herein comprising an oligonucleotide, optionally conjugated to a binding moiety, a polymer, or a combination thereof is used for the treatment of an AR-associated cancer. In some instances, a composition or a pharmaceutical formulation described herein comprising an oligonucleotide, optionally conjugated to a binding moiety, a polymer, or a combination thereof is used for the treatment of an HPRT I-associated cancer. In some instances, a composition or a pharmaceutical formulation described herein comprising an oligonucleotide, optionally conjugated to a binding moiety, a polymer, or a combination thereof is used for the treatment of a pi-catenin associated cancer. In some instances, the cancer is a solid tumor. In some instances, the cancer is a hematologic malignancy. In some instances, the solid tumor is a relapsed or refractory solid tumor, or a metastatic solid tumor. In some cases, the hematologic malignancy is a relapsed or refractory hematologic malignancy, or a metastatic hematologic malignancy. In some instances, the cancer comprises bladder cancer, breast cancer, colorectal cancer, endometrial cancer, esophageal cancer, glioblastoma multiforme, head and neck cancer, kidney cancer, lung cancer, ovarian cancer, pancreatic cancer, prostate cancer, thyroid cancer, acute myeloid leukemia, CLL, DLBCL, or multiple myeloma. In some instances, the β-catenin associated cancer further comprises PIK3C-associated cancer and/or MYC-associated cancer.

Immunotherapy

In some embodiments, a composition or a pharmaceutical formulation described herein is used as an immunotherapy for the treatment of a disease or disorder. In some instances, the immunotherapy is an immuno-oncology therapy. In some instances, immuno-oncology therapy is categorized into active, passive, or combinatory (active and passive) methods. In active immuno-oncology therapy method, for example, tumor-associated antigens (TAAs) are presented to the immune system to trigger an attack on cancer cells presenting these TAAs. In some instances, the active immune-oncology therapy method includes tumor-targeting and/or immune-targeting agents (e.g., checkpoint inhibitor agents such as monoclonal antibodies), and/or vaccines, such as in situ vaccination and/or cell-based or non-cell based (e.g., dendritic cell-based, tumor cell-based, antigen, anti-idiotype, DNA, or vector-based) vaccines. In some instances, the cell-based vaccines are vaccines which are generated using activated immune cells obtained from a patient's own immune system which are then activated by the patient's own cancer. In some instances, the active immune-oncology therapy is further subdivided into non-specific active immunotherapy and specific active immunotherapy. In some instances, non-specific active immunotherapy utilizes cytokines and/or other cell signaling components to induce a general immune system response. In some cases, specific active immunotherapy utilizes specific TAAs to elicit an immune response.

In some embodiments, a composition or a pharmaceutical formulation described herein is used as an active immuno-oncology therapy method for the treatment of a disease or disorder (e.g., cancer). In some embodiments, the composition or a pharmaceutical formulation described herein comprises a tumor-targeting agent. In some instances, the tumor-targeting agent is encompassed by a binding moiety A. In other instances, the tumor-targeting agent is an additional agent used in combination with a molecule of Formula (I). In some instances, the tumor-targeting agent is a tumor-directed polypeptide (e.g., a tumor-directed antibody). In some instances, the tumor-targeting agent is a tumor-directed antibody, which exerts its antitumor activity through mechanisms such as direct killing (e.g., signaling-induced apoptosis), complement-dependent cytotoxicity (CDC), and/or antibody-dependent cell-mediated cytotoxicity (ADCC). In additional instances, the tumor-targeting agent elicits an adaptive immune response, with the induction of antitumor T cells.

In some embodiments, the binding moiety A is a tumor-directed polypeptide (e.g., a tumor-directed antibody). In some instances, the binding moiety A is a tumor-directed antibody, which exerts its antitumor activity through mechanisms such as direct killing (e.g., signaling-induced apoptosis), complement-dependent cytotoxicity (CDC), and/or antibody-dependent cell-mediated cytotoxicity (ADCC). In additional instances, the binding moiety A elicits an adaptive immune response, with the induction of antitumor T cells.

In some embodiments, the composition or a pharmaceutical formulation described herein comprises an immune-targeting agent. In some instances, the immune-targeting agent is encompassed by a binding moiety A. In other instances, the immune-targeting agent is an additional agent used in combination with a molecule of Formula (I). In some instances, the immune-targeting agent comprises cytokines, checkpoint inhibitors, or a combination thereof.

In some embodiments, the immune-targeting agent is a checkpoint inhibitor. In some cases, an immune checkpoint molecule is a molecule presented on the cell surface of CD4 and/or CD8 T cells. Exemplary immune checkpoint molecules include, but are not limited to, Programmed Death-Ligand 1 (PD-L1, also known as B7-H1, CD274), Programmed Death 1 (PD-1), CTLA-4, B7H1, B7H4, OX-40, CD137, CD40, 2B4, IDO1, IDO2, VISTA, CD27, CD28, PD-L2 (B7-DC, CD273), LAG3, CD80, CD86, PDL2, B7H3, HVEM, BTLA, KIR, GAL9, TIM3, A2aR, MARCO (macrophage receptor with collageneous structure), PS (phosphatidylserine), ICOS (inducible T cell costimulator), HAVCR2, CD276, VTCN1, CD70, and CD160.

In some instances, an immune checkpoint inhibitor refers to any molecule that modulates or inhibits the activity of an immune checkpoint molecule. In some instances, immune checkpoint inhibitors include antibodies, antibody-derivatives (e.g., Fab fragments, scFvs, minobodies, diabodies), antisense oligonucleotides, siRNA, aptamers, or peptides. In some embodiments, an immune checkpoint inhibitor is an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, VTCN1, or any combinations thereof.

In some embodiments, exemplary checkpoint inhibitors include:

PD-L1 inhibitors such as Genentech's MPDL3280A (RG7446), Anti-mouse PD-L1 antibody Clone 10F.9G2 (Cat #BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, and AstraZeneca's MEDI4736;

PD-L2 inhibitors such as GlaxoSmithKline's AMP-224 (Amplimmune), and rHIgM12B7;

PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1106 (ONO-4538), Bristol-Myers Squibb's human IgG4 monoclonal antibody nivolumab (Opdivo®, BMS-936558, MDX1106), AstraZeneca's AMP-514 and AMP-224, and Pidilizumab (CT-011) from CureTech Ltd:

CTLA-4 inhibitors such as Bristol Meyers Squibb's anti-CTLA-4 antibody ipilimumab (also known as Yervoy®, MDX-010, BMS-734016 and MDX-101), anti-CTLA4 Antibody, clone 9H10 from Millipore, Pfizer's tremelimumab (CP-675,206, ticilimumab), and anti-CTLA4 antibody clone BNI3 from Abcam;

LAG3 inhibitors such as anti-Lag-3 antibody clone eBioC9B7W (C9B7W) from eBioscience, anti-Lag3 antibody LS-B2237 from LifeSpan Biosciences. IMP321 (ImmuFact) from Immutep, anti-Lag3 antibody BMS-986016, and the LAG-3 chimeric antibody A9H12;

B7-H3 inhibitors such as MGA271:

KIR inhibitors such as Lirilumab (IPH2101):

CD137 (41BB) inhibitors such as urelumab (BMS-663513, Bristol-Myers Squibb), PF-05082566 (anti-4-1BB, PF-2566, Pfizer), or XmAb-5592 (Xencor);

PS inhibitors such as Bavituximab; and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40 (CD134), GITR, ICOS, BTLA (CD272), CD160, 2B4, LAIR1, TIGHT, LIGHT, DR3, CD226, CD2, or SLAM.

In some embodiments, a binding moiety A comprising an immune checkpoint inhibitor is used for the treatment of a disease or disorder (e.g., cancer). In some instances, the binding moiety A is a bispecific antibody or a binding fragment thereof that comprises an immune checkpoint inhibitor. In some cases, a binding moiety A comprising an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, VTCN1, or any combinations thereof, is used for the treatment of a disease or disorder (e.g., cancer).

In some embodiments, a molecule of Formula (I) in combination with an immune checkpoint inhibitor is used for the treatment of a disease or disorder (e.g., cancer). In some instances, the immune checkpoint inhibitor comprises an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure). PS (phosphatidylserine), OX-40, SLAM, TIGHT, VISTA, VTCN1, or any combinations thereof. In some cases, a molecule of Formula (I) is used in combination with ipilimumab, tremelimumab, nivolumab, pemrolizumab, pidilizumab, MPDL3280A, MEDI4736. MSB0010718C, MK-3475, or BMS-936559, for the treatment of a disease or disorder (e.g., cancer).

In some embodiments, the immune-targeting agent is a cytokine. In some cases, cytokine is further subgrouped into chemokine, interferon, interleukin, and tumor necrosis factor. In some embodiments, chemokine plays a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL11, CXCL11, CXCL12, CXCL13, CXCL14, CXCL15, CXCL16, and CXCL17; the XC subfamily: XCL1 and XCL2; and the CX3C subfamily CX3CL 1.

Interferon (IFNs) comprises interferon type I (e g, IFN-α, IFN-β, IFN-ε, IFN-κ, and IFN-ω), interferon type 11 (e.g. IFN-γ), and interferon type III, In some embodiments, IFN-α is further classified into about 13 subtypes which include IFNA1, IFNA2, IFNA4, IFNA5, IFNA6, IFNA7, IFNA8, IFNA10, IFNA13, IFNA14, IFNA16. IFNA17, and IFNA21.

Interleukin is expressed by leukocyte or white blood cell and promote the development and differentiation of T and B lymphocytes and hematopoietic cells. Exemplary interleukins include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-IBBL, OX40L, and TNF-related apoptosis inducing ligand (TRAIL).

In some embodiments, a molecule of Formula (I) in combination with a cytokine is used for the treatment of a disease or disorder (e.g., cancer). In some cases, a molecule of Formula (I) in combination with a chemokine is used for the treatment of a disease or disorder (e.g., cancer). In some cases, a molecule of Formula (I) in combination with an interferon is used for the treatment of a disease or disorder (e.g., cancer). In some cases, a molecule of Formula (I) in combination with an interleukin is used for the treatment of a disease or disorder (e.g., cancer). In some cases, a molecule of Formula (I) in combination with a tumor necrosis factor is used for the treatment of a disease or disorder (e.g., cancer). In some instances, a molecule of Formula (I) in combination with IL-1β, IL-2, IL-7, IL-8, IL-15, MCP-1 (CCL2), MIP-1α, RANTES, MCP-3, MIP5, CCL19, CCL21, CXCL2, CXCL9, CXCL10, or CXCL11 is used for the treatment of a disease or disorder (e.g., cancer).

In some embodiments, the composition or a pharmaceutical formulation described herein comprises a vaccine. In some instances, the vaccine is an in situ vaccination. In some instances, the vaccine is a cell-based vaccine. In some instances, the vaccine is a non-cell based vaccine. In some instances, a molecule of Formula (I) in combination with dendritic cell-based vaccine is used for the treatment of a disease or disorder (e.g., cancer). In some instances, a molecule of Formula (I) in combination with tumor cell-based vaccine is used for the treatment of a disease or disorder (e.g., cancer). In some instances, a molecule of Formula (I) in combination with antigen vaccine is used for the treatment of a disease or disorder (e.g., cancer). In some instances, a molecule of Formula (I) in combination with anti-idiotype vaccine is used for the treatment of a disease or disorder (e.g., cancer). In some instances, a molecule of Formula (I) in combination with DNA vaccine is used for the treatment of a disease or disorder (e.g., cancer). In some instances, a molecule of Formula (I) in combination with vector-based vaccine is used for the treatment of a disease or disorder (e.g., cancer).

In some embodiments, a composition or a pharmaceutical formulation described herein is used as a passive immuno-oncology therapy method for the treatment of a disease or disorder (e.g., cancer). The passive method, in some instances, utilizes adoptive immune system components such as T cells, natural killer (NK) T cells, and/or chimeric antigen receptor (CAR) T cells generated exogenously to attack cancer cells.

In some embodiments, a molecule of Formula (I) in combination with a T-cell based therapeutic agent is used for the treatment of a disease or disorder (e.g., cancer). In some cases, the T-cell based therapeutic agent is an activated T-cell agent that recognizes one or more of a CD cell surface marker described above. In some instances, the T-cell based therapeutic agent comprises an activated T-cell agent that recognizes one or more of CD2, CD3, CD4, CD5, CD8, CD27, CD28, CD80, CD134, CD137, CD152, CD154, CD160, CD200R, CD223, CD226, CD244, CD258, CD267, CD272, CD274, CD278, CD279, or CD357. In some instances, a molecule of Formula (I) in combination with an activated T-cell agent recognizing one or more of CD2, CD3, CD4, CD5, CD8, CD27, CD28, CD80, CD134, CD137, CD152, CD154, CD160, CD200R, CD223, CD226, CD244. CD258. CD267, CD272, CD274, CD278, CD279, or CD357 is used for the treatment of a disease or disorder (e.g., cancer).

In some embodiments, a molecule of Formula (I) in combination with natural killer (NK) T cell-based therapeutic agent is used for the treatment of a disease or disorder (e.g., cancer). In some instances, the NK-based therapeutic agent is an activated NK agent that recognizes one or more of a CD cell surface marker described above. In some cases, the NK-based therapeutic agent is an activated NK agent that recognizes one or more of CD2, CD11a, CD11b, CD16, CD56, CD58, CD62L, CD85j, CD158a/b, CD158c, CD158e/f/k, CD158h/j. CD159a, CD162, CD226, CD314, CD335, CD337, CD244, or CD319. In some instances, a molecule of Formula (I) in combination with an activated NK agent recognizing one or more of CD2, CD11a, CD11b, CD16, CD56, CD58, CD62L, CD85j, CD158a/b, CD158c, CD158e/f/k, CD158h/j, CD159a, CD162, CD226, CD314, CD335, CD337, CD244, or CD319 is used for the treatment of a disease or disorder (e.g., cancer).

In some embodiments, a molecule of Formula (I) in combination with CAR-T cell-based therapeutic agent is used for the treatment of a disease or disorder (e.g., cancer).

In some embodiments, a molecule of Formula (I) in combination with an additional agent that destabilizes the endosomal membrane (or disrupts the endosomal-lysosomal membrane trafficking) is used for the treatment of a disease or disorder (e.g., cancer). In some instances, the additional agent comprises an antimitotic agent. Exemplary antimitotic agents include, but are not limited to, taxanes such as paclitaxel and docetaxel; vinca alkaloids such as vinblastine, vincristine, vindesine, and vinorelbine; cabazitaxel; colchicine; eribulin; estramustine; etoposide; ixabepilone; podophyllotoxin; teniposide; or griseofulvin. In some instances, the additional agent comprises paclitaxel, docetaxel, vinblastine, vincristine, vindesine, vinorelbine, cabazitaxel, colchicine, eribulin, estramustine, etoposide, ixabepilone, podophyllotoxin, teniposide, or griseofulvin. In some instances, the additional agent comprises taxol. In some instances, the additional agent comprises paclitaxel. In some instances, the additional agent comprises etoposide. In other instances, the additional agent comprises vitamin K3.

In some embodiments, a composition or a pharmaceutical formulation described herein is used as a combinatory method (including for both active and passive methods) in the treatment of a disease or disorder (e.g., cancer).

Muscle Dystrophy, Muscle Atrophy, Muscle Wasting

In one embodiment, muscle dystrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle dystrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g., by a muscle volume/cross-section area (CSA) MRI method).

Myotonic dystrophy is a multisystemic neuromuscular disease comprising two main types: myotonic dystrophy type 1 (DM1) and myotonic dystrophy type 2 (DM2). DM1 is caused by a dominantly inherited "CTG" repeat expansion in the gene DM protein kinase (DMPK), which when transcribed into mRNA, forms hairpins that bind with high affinity to the Muscleblind-like (MBNL) family of proteins. MBNL proteins are involved in post-transcriptional splicing and polyadenylatin site regulation and loss of the MBNL protein functions lead to downstream accumulation of nuclear foci and increase in mis-splicing events and subsequently to myotonia and other clinical symptoms.

In some embodiments, described herein is a method of treating muscle dystrophy, muscle atrophy, and/or muscle wasting in a subject, which comprises providing a polynucleic acid molecule described herein or a polynucleic acid molecule conjugate described herein and administering to the subject a therapeutically effective amount of the polynucleic acid molecule or polynucleic acid molecule conjugate to the subject in need thereof to treat the muscular dystrophy muscle atrophy, and/or muscle wasting. In some embodiments, the polynucleic acid molecules or polynucleic acid molecule conjugates target a gene transcripts that are mutated or upregulated such that downregulation, deletion, exon skipping of transcripts are desired to treat the diseases. In some embodiments, the polynucleic acid molecules or polynucleic acid molecule conjugates target DMPK mRNA, DMD mRNA, or GYS1 mRNA.

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate-release formulations, controlled-release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanopores and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin, dextrin, or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100, or more polynucleic acid molecules or binding moieties described herein are conjugated either directly or indirectly to a nanoparticle.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa., Mack Publishing Company, 1995); Hoover, John E., *Remington's Pharmaceutical Sciences*, Mack Publishing Co., Easton, Pennsylvania 1975; Liberman, H. A, and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

In some instances, the pharmaceutical formulations further include pH-adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PHI 02, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials.

Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide, and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, are optionally reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include a molecule of Formula (Xa): A-X—B¹—Y—C, as disclosed herein. Such kits optionally include an identifying description or label or instructions relating to its use in the methods described herein.

A kit typically includes labels listing contents and/or instructions for use and package inserts with instructions for use. A set of instructions will also typically be included.

In one embodiment, a label is on or associated with the container. In one embodiment, a label is on a container when letters, numbers, or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Chemical Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P. Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—CH, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), I-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene." alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〜〜〜" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In certain embodiments, the alkylarylene group has the formula:

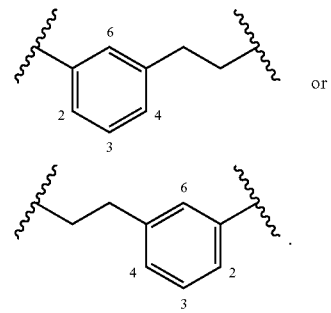

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$ —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In certain embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O) NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR'NR'"R"", —CN, —NO$_2$, —R', —N$_3$, —CH(Ph)$_2$, fluoro (C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some certain embodiments, each substituted group described in the compounds herein is substituted with at least one substituent group. More specifically, in some certain embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other certain embodiments, at least one or all of these groups are substituted with at least one size-limited substituent group. In other certain embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some certain embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some certain embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some certain embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of R'3 and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In certain embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In certain embodiments, an agonist is a molecule that interacts with a target to cause or promote an increase in the activation of the target. In certain embodiments, activators are molecules that increase, activate, facilitate, enhance activation, sensitize, or up-regulate, e.g., a gene, protein, ligand, receptor, or cell.

As defined herein, the term "inhibition," "inhibit," "inhibiting," and the like, in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In certain embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In certain embodiments, inhibition refers to a reduction of activity of a target protein resulting from a direct interaction (e.g. an inhibitor binds to the target protein). In certain embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1,5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In certain embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "disease" or "condition" refer to a state of being or health status of a patient or subject capable of being treated with the compounds or methods provided herein. The disease may be a cancer.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In certain embodiments, treating is preventing. In certain embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In certain embodiments, prevent refers to slowing the progression of the disease, disorder or condition or inhibiting progression thereof to a harmful or otherwise undesired state.

EXAMPLES

These examples are provided for illustrative purposes only and not to limit the scope of the claims provided herein.

Chemical Synthesis Examples

The compounds in Table 1 are prepared as described in the following examples.

TABLE 1

| Compound/Eg No | Structure | AVID No |
|---|---|---|
| 1 | 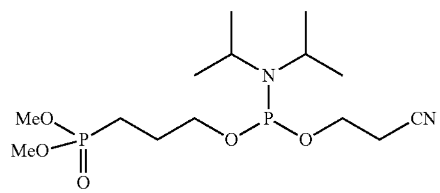 [SMILES: COP(=O)(CCCOP(OCCC#N)N(C(C)C)C(C)C)OC] | vpUh |
| 2 | 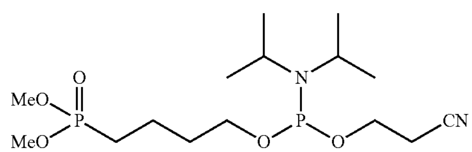 [SMILES: COP(=O)(CCCCOP(OCCC#N)N(C(C)C)C(C)C)OC] | vpUe |
| 3 | 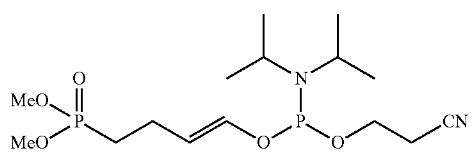 [SMILES: COP(=O)(CC/C=C/OP(OCCC#N)N(C(C)C)C(C)C)OC] | vpUb |
| 4 | 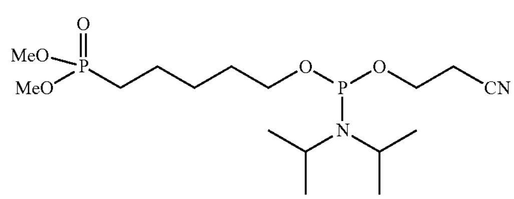 [SMILES: COP(=O)(CCCCCOP(OCCC#N)N(C(C)C)C(C)C)OC] | vpUk |
| 5 | 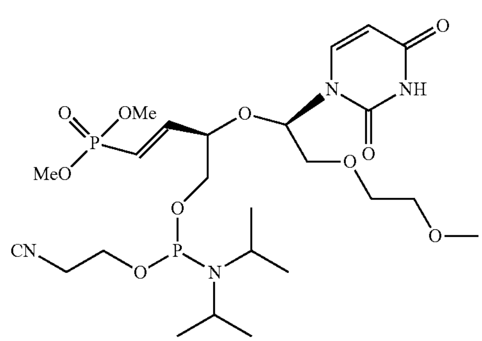 | vPUq |

TABLE 1-continued

| Compound/Eg No | Structure | AVID No |
|---|---|---|
| 6 | 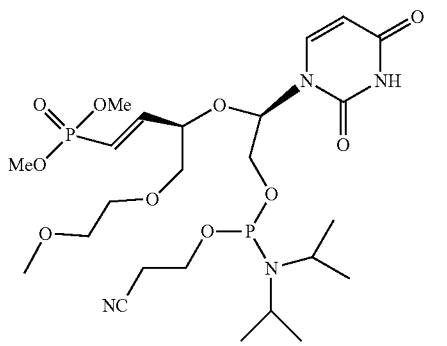 [SMILES: COCCOC[C@@H](/C=C/P(=O)(OC)OC)O[C@H](COP(OCCC#N)N(C(C)C)C(C)C)n1ccc(=O)[nH]c1=O] | vPUw |
| 7 | 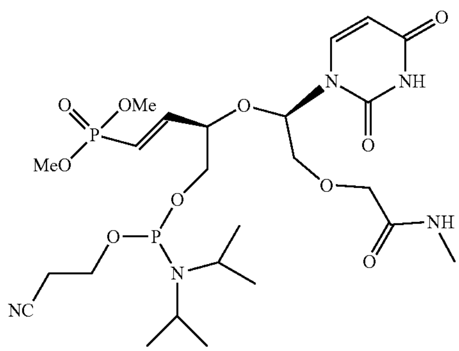 [SMILES: CNC(=O)COC[C@@H](O[C@H](/C=C/P(=O)(OC)OC)COP(OCCC#N)N(C(C)C)C(C)C)n1ccc(=O)[nH]c1=O] | vPUx |
| 8 | 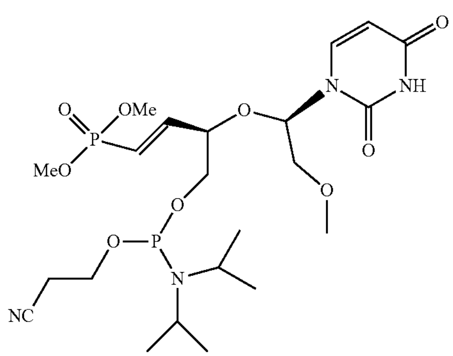 [SMILES: COC[C@@H](O[C@H](/C=C/P(=O)(OC)OC)COP(OCCC#N)N(C(C)C)C(C)C)n1ccc(=O)[nH]c1=O] | vPUy |
| 10 | 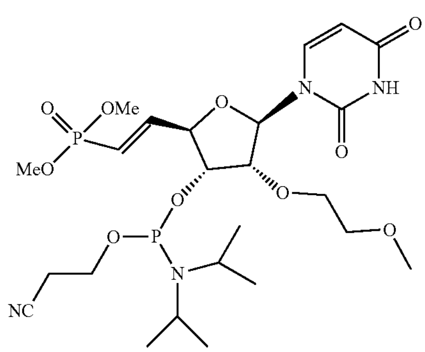 [SMILES: COCCO[C@@H]1[C@H](OP(OCCC#N)N(C(C)C)C(C)C)[C@@H](/C=C/P(=O)(OC)OC)O[C@H]1n1ccc(=O)[nH]c1=O] | vPUm |
| 11 | 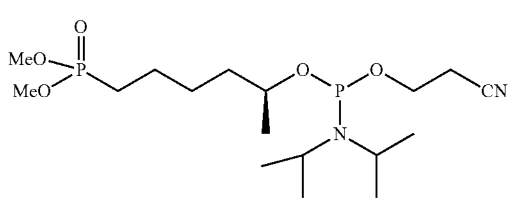 [SMILES: COP(=O)(CCCC[C@H](C)OP(OCCC#N)N(C(C)C)C(C)C)OC] | |

TABLE 1-continued

| Compound/Eg No | Structure | AVID No |
|---|---|---|
| 12 | [chemical structure: dimethyl phosphonate with methoxy-substituted chain linked via O-P(N(iPr)2)-O-CH2CH2-CN] | |
| 13 | [chemical structure: dimethyl phosphonate-CH2CH2-O-CH2CH2-O-P(N(iPr)2)-O-CH2CH2-CN] | |
| 14 | [chemical structure: dimethyl phosphonate-CH2CH2-S-CH2CH2-O-P(N(iPr)2)-O-CH2CH2-CN] | |
| 15 | [chemical structure: dimethyl phosphonate-CD2CH2-S-CH2CD2-O-P(N(iPr)2)-O-CH2CH2-CN] | |
| 16 | [chemical structure: dimethyl phosphonate-CH2CH2-N(Me)-CH2CH2-O-P(N(iPr)2)-O-CH2CH2-CN] | |
| 17 | [chemical structure: dimethyl phosphonate-CH2CH2-cyclohexyl-O-P(N(iPr)2)-O-CH2CH2-CN] | |
| 18 | [chemical structure: cyclohexyl bearing dimethyl phosphonate and CH2-O-P(N(iPr)2)-O-CH2CH2-CN] | |

TABLE 1-continued

| Compound/Eg No | Structure | AVID No |
|---|---|---|
| 19 | 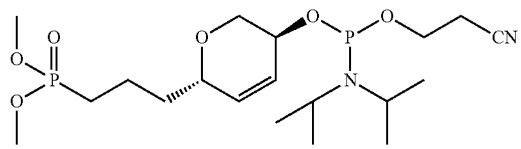 [SMILES: COP(=O)(CCC[C@H]1C=C[C@H](OP(OCCC#N)N(C(C)C)C(C)C)CO1)OC] | |
| 20 | 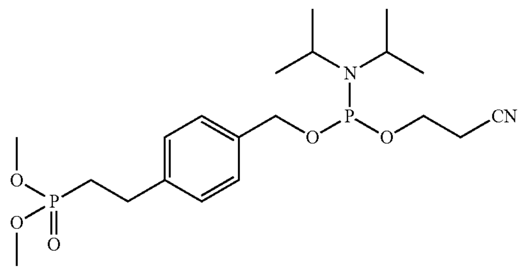 [SMILES: COP(=O)(CCc1ccc(COP(OCCC#N)N(C(C)C)C(C)C)cc1)OC] | |
| 21 | 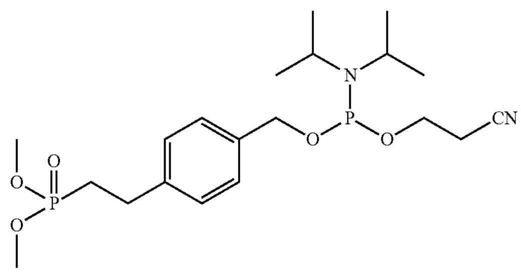 [SMILES: COP(=O)(CCc1ccc(COP(OCCC#N)N(C(C)C)C(C)C)cc1)OC] | |
| 22 | 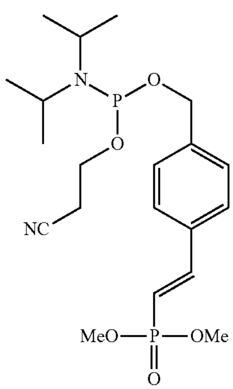 [SMILES: COP(=O)(/C=C/c1ccc(COP(OCCC#N)N(C(C)C)C(C)C)cc1)OC] | |
| 23 | 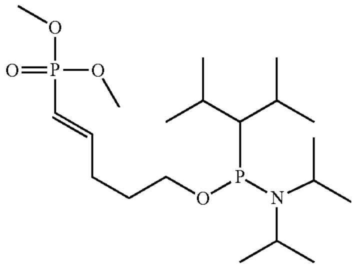 [SMILES: COP(=O)(/C=C/CCCOP(C(C(C)C)C(C)C)N(C(C)C)C(C)C)OC] | |

TABLE 1-continued

| Compound/Eg No | Structure | AVID No |
|---|---|---|
| 24 | 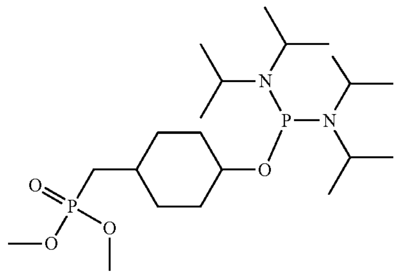 [SMILES: COP(=O)(CC1CCC(OP(N(C(C)C)C(C)C)N(C(C)C)C(C)C)CC1)OC] | |
| 25 | 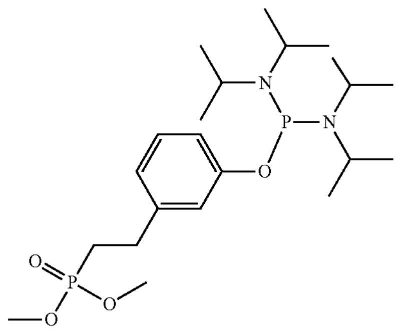 [SMILES: COP(=O)(CCc1cccc(OP(N(C(C)C)C(C)C)N(C(C)C)C(C)C)c1)OC] | |
| 26 | 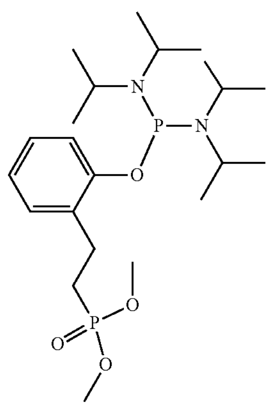 [SMILES: COP(=O)(CCc1ccccc1OP(N(C(C)C)C(C)C)N(C(C)C)C(C)C)OC] | |
| 27 | 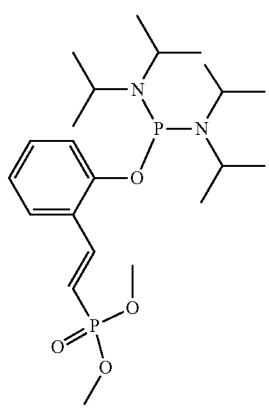 [SMILES: COP(=O)(/C=C/c1ccccc1OP(N(C(C)C)C(C)C)N(C(C)C)C(C)C)OC] | |

Example 1: 2-cyanoethyl (3-(dimethoxypropyl)propyl)diisopropylphosphoramidite

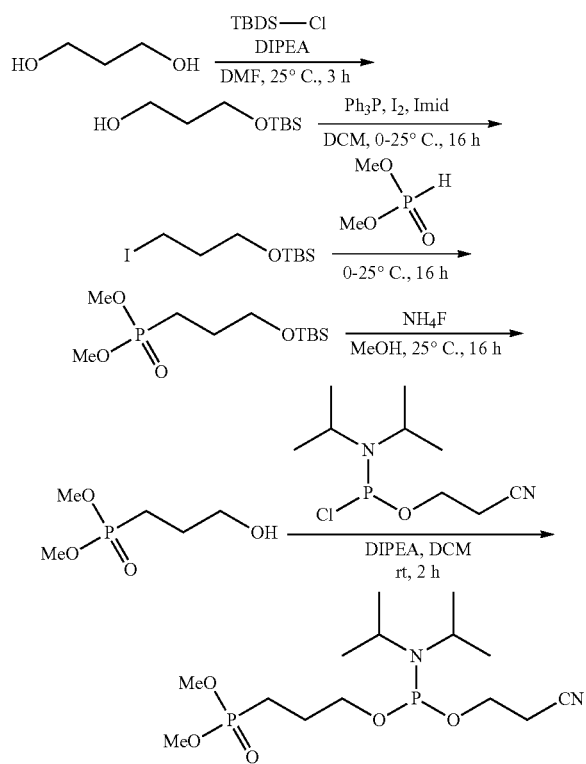

Step 1A: 3-((tert-butyldimethylsilyl)oxy)propan-1-ol

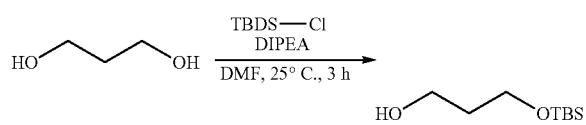

To a solution of propane-1,3-diol (1.00 eq) in DMF was added DIPEA (10.0 eq) and TBSCl (1.05 eq). The mixture was stirred at 25° C. for 16 h. TLC (Petroleum ether/Ethyl acetate=5/1, $R_f$=0.43) indicated the propane-1,3-diol was consumed completely. The reaction mixture was concentrated under reduced pressure, diluted with ethyl acetate (100 mL) and washed with water (200 mL×3). The combined organic layers were washed with brine (200 mL), dried over $Na_2SO_4$, filtered and concentrated under reduced pressure to give a residue which was purified by column chromatography ($SiO_2$, PMA Petroleum ether/Ethyl acetate=100/1 to 1/1).

Step 1B: tert-butyl(3-iodopropoxy)dimethylsilane

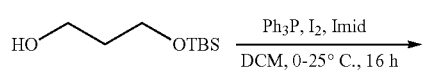

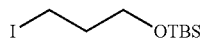

Imidazole (1.50 eq) and iodine (1.35 eq) were added to a solution of $PPh_3$ (1.20 eq) in DCM, 3-((tert-butyldimethylsilyl)oxy)propan-1-ol (1.00 eq) in DCM was added dropwise to the mixture, which was stirred at 25° C. for 16 h. TLC (Petroleum ether/Ethyl acetate=5/1, compound 3B: $R_f$=0.89) indicated tert-butyl(3-iodopropoxy)dimethylsilane was consumed completely. The reaction mixture was concentrated under reduced pressure and the resulting residue purified by column chromatography ($SiO_2$, PMA Petroleum ether/Ethyl acetate=1/0 to 100/1).

Step 1C: dimethyl (3-((tert-butyldimethylsilyl)oxy)propyl)phosphonate

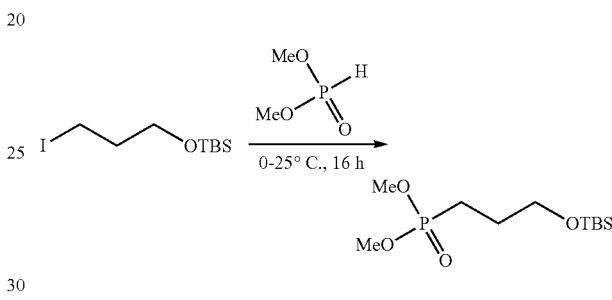

To a solution of dimethyl phosphonate (1.30 eq) in THF was added sodium hydride (1.30 eq) at 0° C. The mixture was stirred at 0° C. for 0.5 h and then at 70° C. for 1.5 h. The mixture was then cooled to 0° C., and tert-butyl(3-iodopropoxy)dimethylsilane (1.00 eq) in THF was added to the mixture and stirred for 25° C. for 24 h. TLC (Petroleum ether: Ethyl acetate=1:1, product: $R_f$=0.38) indicated starting material was consumed completely. The reaction mixture was quenched by addition $NH_4Cl$, and then diluted with ethyl acetate and washed with $NH_4Cl$. The combined organic layers were washed with brine, dried over $Na_2SO_4$, filtered and concentrated under reduced pressure to give a residue which was purified by column chromatography ($SiO_2$, PMA, Petroleum ether: Ethyl acetate=1:0 to 1:1).

Step 1D: dimethyl (3-hydroxypropyl)phosphonate

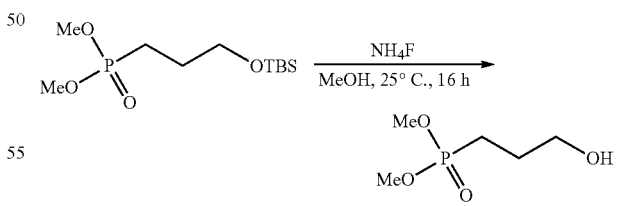

To a solution of dimethyl (3-((tert-butyldimethylsilyl)oxy)propyl)phosphonate (1.00 eq) in MeOH was added $NH_4F$ (3.00 eq). The mixture was stirred at 65° C. for 3 h. TLC (Petroleum ether/Ethyl acetate=0/1, product $R_f$=0.09) indicated strating material was consumed completely. The reaction mixture was concentrated under reduced pressure and the resulting residue purified by column chromatography ($SiO_2$, $KMnO_4$ Petroleum ether/Ethyl acetate=10/1 to 0:1).

Step 1E: 2-cyanoethyl (3-(dimethoxyphosphoryl)propyl) diisopropylphosphoramidite

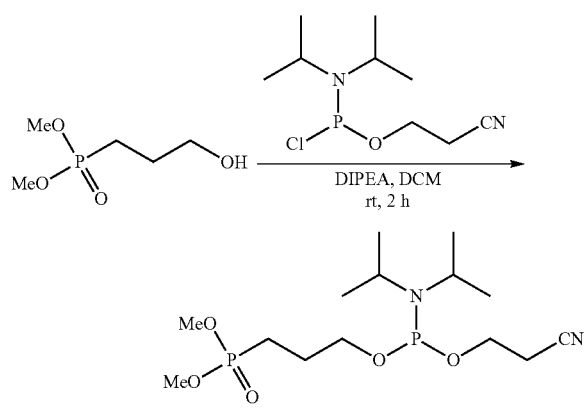

To a solution of dimethyl (3-hydroxypropyl)phosphonate (1.00 eq) in DCM was added DIPEA (4.00 eq) and 3-((chloro(diisopropylamino)phosphaneyl)oxy)propanenitrile (1.20 eq) at 0° C. The mixture was stirred at 25° C. for 1 hr. TLC (Petroleum ether/Ethyl acetate=0/1, product $R_f$=0.43) indicated compound was consumed completely. The reaction mixture was quenched by addition NaHCO$_3$, diluted with DCM and extracted with DCM (5 mL×2). The combined organic layers were washed with brine, dried over Na$_2$SO$_4$, filtered and concentrated under reduced pressure to give a residue which was purified by column chromatography (SiO$_2$, petroleum ether/ethyl acetate/TEA/DCM=10/1/0.5%/25% to 3/1/0.5%0/25%).

$^1$H NMR: 400 MHz, CD$_3$CN: δ ppm 3.51-3.75 (m, 2H), 3.55-3.70 (m, 10H), 2.64 (t, J=6.02 Hz, 2H), 1.76-1.83 (m, 4H), 1.16-1.18 (m, 12H)

$^{31}$P NMR: 162 MHz, CD$_3$CN: δ ppm 147.19 (s, 1P), 34.03 (s, 1P).

Example 2: 2-cyanoethyl (4-(dimethoxyphosphoryl)butyl) diisopropylphosphoramidite

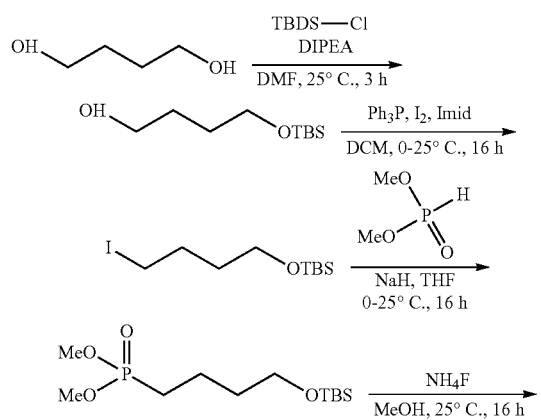

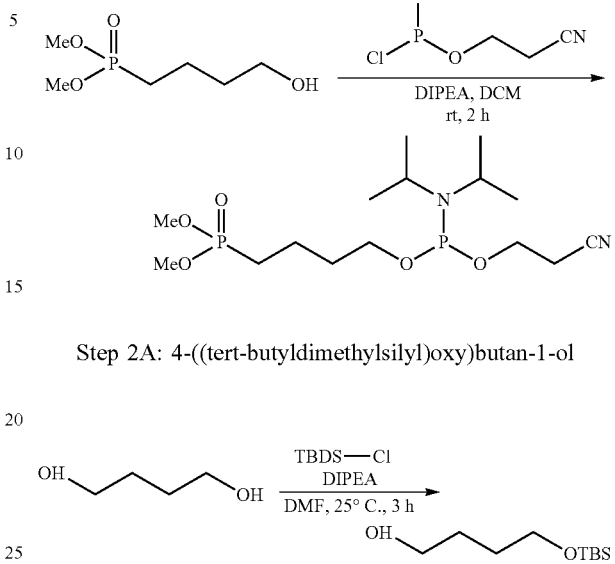

Step 2A: 4-((tert-butyldimethylsilyl)oxy)butan-1-ol

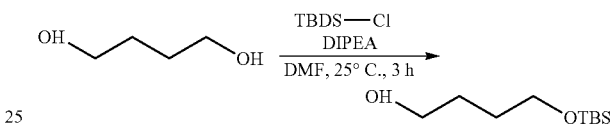

To a solution of butane-1,4-diol (10.0 g, 110 mmol, 9.80 mL, 1.00 eq) in DMF (70.0 mL) was added DIPEA (143 g, 1.11 mol, 193 mL, 10.0 eq) and TBSCl (17.5 g, 116 mmol, 14.3 mL, 1.05 eq). The mixture was stirred at 25° C. for 16 h. TLC (Petroleum ether/Ethyl acetate=5/1, $R_f$=0.43) indicated starting material was consumed completely. The reaction mixture was concentrated under reduced pressure to give a residue, and then diluted with Ethyl acetate (100 mL) and washed with water (200 mL×3). The combined organic layers were washed with brine (200 mL), dried over Na$_2$SO$_4$, filtered and concentrated under reduced pressure to give a residue. The residue was purified by column chromatography (SiO$_2$, PMA Petroleum ether/Ethyl acetate=100/1 to 1/1), 4-((tert-butyldimethylsilyl)oxy)butan-1-ol (112 g, 58.7 mmol, 52.9% yield) was obtained as a white solid.

$^1$H NMR: 400 MHz, CDCl$_3$: δ ppm 3.51-3.65 (m, 4H), 1.43-1.66 (m, 4H), 0.80-0.86 (m, 9H), −0.06-0.03 (m, 6H).

Step 2B: tert-butyl(4-iodobutoxy)dimethylsilane

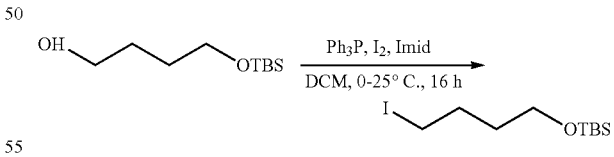

To a solution of PPh$_3$ (7.70 g, 29.3 mmol, 1.20 eq) in DCM (20.0 mL) was added imidazole (2.50 g, 36.7 mmol, 1.50 eq) and iodine (8.38 g, 33.0 mmol, 6.65 mL, 1.35 eq), 4-((tert-butyldimethylsilyl)oxy)butan-1-ol (5.00 g, 24.4 mmol, 1.00 eq) in DCM (15.0 mL) was added dropwise to the mixture. The mixture was stirred at 25° C. for 16 h. TLC (Petroleum ether/Ethyl acetate=5/1, $R_f$=0.89) indicated starting material was consumed completely. The reaction mixture was concentrated under reduced pressure and the resulting residue purified by column chromatography (SiO$_2$, PMA Petroleum ether/Ethyl acetate=1/0 to 100/1), tert-butyl(4- iodobutoxy)dimethylsilane (6.70 g, 21.32 mmol, 87.1% yield) was obtained as a colorless oil.

$^1$H NMR: 400 MHz, CDCl$_3$: δ ppm 3.64 (t, J=6.2 Hz, 2H), 3.23 (t, J=7.0 Hz, 2H), 1.92 (q, J=7.2 Hz, 2H), 1.58-1.68 (m, 2H), 0.89-0.93 (m, 9H), 0.03-0.08 (m, 6H).

Step 2C: dimethyl (4-((tert-butyldimethylsilyl)oxy)butyl)phosphonate

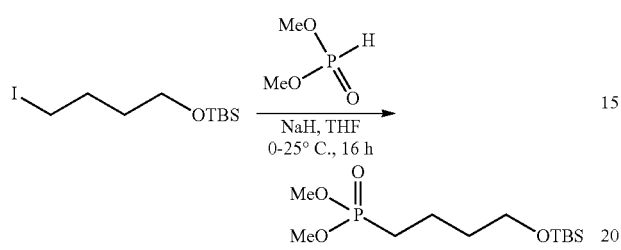

To a solution of dimethyl phosphonate (1.46 g, 13.2 mmol, 1.21 mL, 1.30 eq) in THF (15.0 mL) was added NaH (529 mg, 13.2 mmol, 60.0% purity, 1.30 eq) at 0° C., the mixture was stirred at 0° C. for 0.5 h and 70° C. for 1.5 h. Then the reaction mixture was cooled to 0° C., tert-butyl(4-iodobutoxy)dimethylsilane (3.20 g, 10.2 mmol, 2.64 mL, 1.00 eq) in THF (5.00 mL) was added to the mixture and stirred for 25° C. for 24 h. TLC (Petroleum ether: Ethyl acetate=1:1, product: R$_f$=0.38) indicated starting material was consumed completely. The reaction mixture was quenched by addition of NH$_4$Cl (100 mL), and then diluted with ethyl acetate (100 mL) and washed with NH$_4$Cl (100 mL). The combined organic layers were washed with brine (100 mL), dried over Na$_2$SO$_4$, filtered and concentrated under reduced pressure to give a residue which was purified by column chromatography (SiO$_2$, PMA, Petroleum ether: Ethyl acetate=1:0 to 1:1). Dimethyl (4-((tert-butyldimethylsilyl)oxy)butyl)phosphonate (2.20 g, 7.42 mmol, 72.9% yield) was obtained as a colorless oil.

$^1$H NMR: 400 MHz, CDCl$_3$: δ ppm 3.74 (d, J=10.8 Hz, 6H), 3.62 (t, J=6.0 Hz, 2H), 1.57-1.83 (m, 7H), 0.89 (s, 9H), 0.05 (s, 6H)

$^{31}$P NMR: 162 MHz CDCl$_3$: δ ppm 34.93 (s, 1P).

Step 2D: dimethyl 4-hydroxybutyl)phosphonate

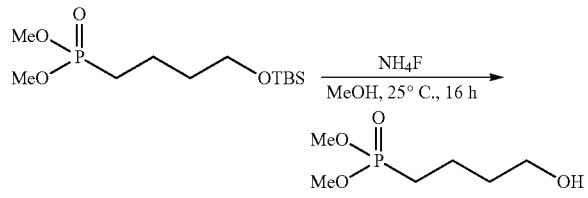

To a solution of dimethyl (4-((tert-butyldimethylsilyl)oxy)butyl)phosphonate (2.10 g, 7.08 mmol, 1.00 eq) in MeOH (21.0 mL) was added NH$_4$F (787 mg, 21.2 mmol, 3.00 eq). The mixture was stirred at 65° C. for 3 h. TLC (Petroleum ether/Ethyl acetate=0/1, R$_f$=0.09) indicated starting material was consumed completely. The reaction mixture was concentrated under reduced pressure and purified by column chromatography (SiO$_2$, KMnO$_4$ Petroleum ether/ Ethyl acetate=10/1 to 0:1). Dimethyl (4-hydroxybutyl)phosphonate (1.3 g, crude) was obtained as a colorless oil. $^1$H NMR: 400 MHz, CDCl$_3$: δ ppm 3.74 (d, J=10.8 Hz, 6H), 3.66 (t, J=6.0 Hz, 2H), 1.98 (s, 1H), 1.62-1.85 (m, 6H).

Step 2E: 2-Cyanoethyl (4-(dimethoxyphosphoryl)butyl) diisopropylphosphoramidite

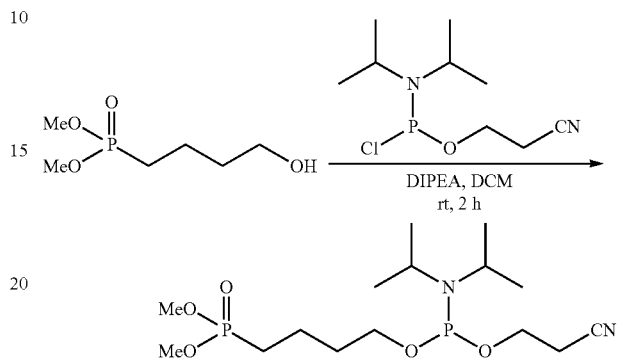

To a solution of dimethyl (4-hydroxy butyl)phosphonate (1.30 g, 7.14 mmol, 1.00 eq) in DCM (13.0 mL) was added DIPEA (3.69 g, 28.5 mmol, 4.97 mL, 4.00 eq) and 3-((chloro (diisopropylamino) phosphaneyl)oxy) propanenitrile (2.03 g, 8.56 mmol, 1.20 eq) at 0° C. The mixture was stirred at 25° C. for 1 hr. TLC (Petroleum ether/Ethyl acetate=0/1, product: R$_f$=0.43) indicated compound was consumed completely. The reaction mixture was quenched by addition NaHCO$_3$ (20 mL), and then diluted with DCM (10 mL) and extracted with DCM (5 mL×2). The combined organic layers were washed with brine (20 mL), dried over Na$_2$SO$_4$, filtered and concentrated under reduced pressure to give a residue. The residue was purified by column chromatography (SiO$_2$, petroleum ether/ethyl acetate/TEA/DCM=10/1/ 0.5%/25% to 3/1/0.5%/25%). 2-cyanoethyl (4-(dimethoxyphosphoryl)butyl) diisopropylphosphoramidite (0.173 g, 452 umol, 6.34% yield) was obtained as colorless oil.

$^1$H NMR: 400 MHz, CD$_3$CN: δ ppm 3.71-3.84 (m, 2H), 3.56-3.70 (m, 10H), 2.64 (t, J=6.02 Hz, 2H), 1.58-1.79 (m, 7H), 1.13-1.20 (m, 14H).

$^{31}$P NMR: 162 MHz, CD$_3$CN: δ ppm 147.03 (s, 1P), 34.12 (s, 1P).

Example 3: (dimethyl (E)-(5-((2-cyanoethoxy)(diisopropylamino)phosphaneyl)pent-1-en-1-yl)phosphonate)

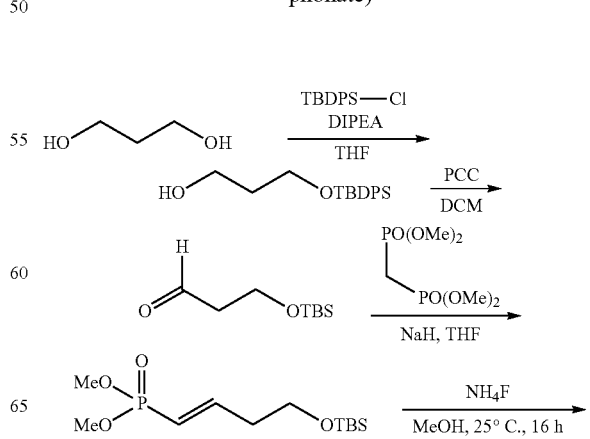

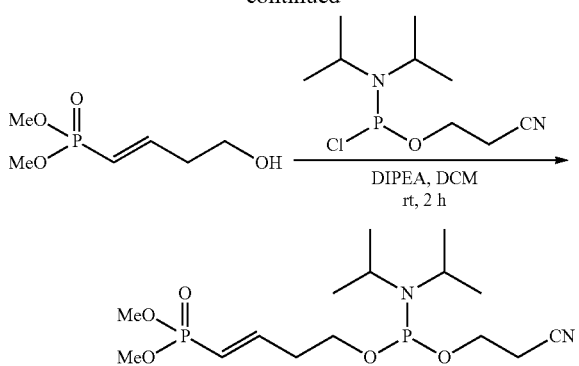

Step 3A: 3-((tert-butyldiphenylsilyl)oxy)propan-1-ol

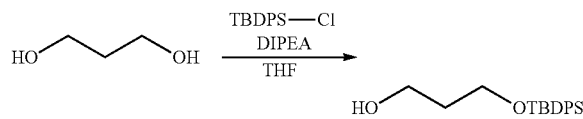

To a solution of propane-1,3-diol (9.0 g, 100 mmol, 1 eq) in DMF (90.0 mL) was added DIPEA (143 g, 1.11 mol, 193 mL, 10.0 eq) and TBDPSCl (30.4 g, 110 mmol). The mixture was stirred at 25° C. for 16 h. TLC (Petroleum ether/Ethyl acetate=5/I, product $R_f$=0.55) indicated starting material was consumed completely. The reaction mixture was concentrated under reduced pressure, diluted with ethyl acetate (100 mL) and washed with $H_2O$ (200 mL×3). The combined organic layers were washed with brine (200 mL), dried over $Na_2SO_4$, filtered and concentrated under reduced pressure to give a residue. The residue was purified by column chromatography (SiO$_2$, PMA Petroleum ether/Ethyl acetate=100/1 to 1/1), 3-(tert-butyldiphenylsilyl)oxy)propan-1-ol (16.4 g, 50% yield) was obtained as a white solid.

Step 3B: 3-tert-butyldiphenylsilyl)oxy)propanal

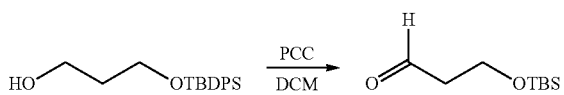

A solution of 3-((tert-butyldiphenylsilyl)oxy)propan-1-ol (16.4 g, 50 mmol, 1 eq) in dichloromethane (200 mL) was cooled in an ice bath under inert atmosphere. PCC (11.8 g, 55 mmol) was added in five portions and the reaction mixture allowed to warm to RT in 1 hr and stirred at RT for another 2 hrs. The reaction mixture was filtered, and the filtrate washed with ether. The combined organic layers were washed with brine (200 mL), dried over $Na_2SO_4$, filtered and concentrated under reduced pressure to give a residue which was used in the next reaction without further purification.

Step 3C: Dimethyl-(4-((tert-butyldiphenylsilyl)oxy) but-1-en-1-yl)phosphonate

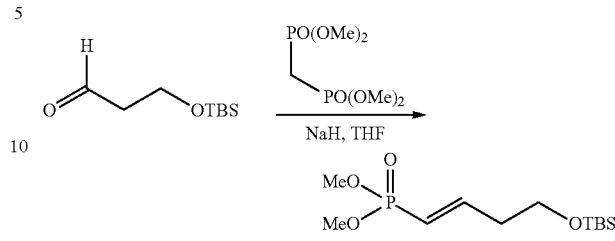

A solution of tetramethyl methylenediphosphonate in dichloromethane (200 mL) was cooled in an ice bath under inert atmosphere and NaH was added in several portions under argon atmosphere, 3-((tert-butyldiphenylsilyl)oxy) propanal was introduced via syringe and the reaction mix slowly allowed to come to RT over 2 hrs and stirred at RT for another 3 hrs. The reaction mixture was quenched with $NH_4Cl$ solution and then washed with $NH_4Cl$ solution (3×50 ml). The organic layer was washed with brine, dried over $Na_2SO_4$, filtered and concentrated under reduced pressure to give a gummy residue which was purified over silica gel chromatography (Petroleum ether/Ethyl acetate=100/1 to 1/1), dimethyl (E)-(4-((tert-butyldiphenylsilyl)oxy)but-1-en-1-yl)phosphonate (4.1 g, 22% yield from compound 2) was obtained as a white solid.

Step 3D: dimethyl-(4-hydroxybut-1-en-1-yl)phosphonate

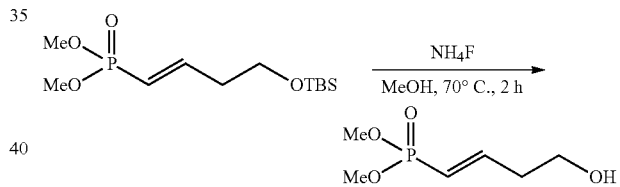

To a solution of dimethyl (E)-(4-((tert-butyldiphenylsilyl) oxy)but-1-en-1-yl)phosphonate (4 g) in methanol (20.0 mL) was added $NH_4F$ (644 mg, 2 eq). The mixture was stirred at 70° C. for 2 h. The reaction mixture was concentrated under reduced pressure to remove solvent. The residue was purified by column chromatography (SiO$_2$, KMnO$_4$ Petroleum ether/Ethyl acetate=10/1 to 0:1). Dimethyl-(4-hydroxybut-1-en-1-yl)phosphonate (1.06 g) was obtained as a colorless oil.

Step 3E: 2-cyanoethyl (4-(dimethoxyphosphoryl)but-3-en-1-yl) diisopropylphosphoramidite

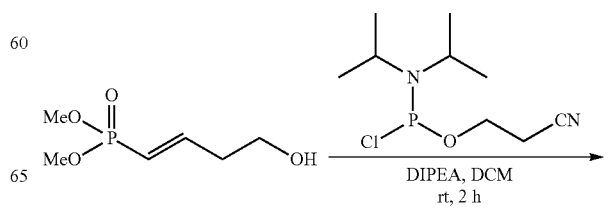

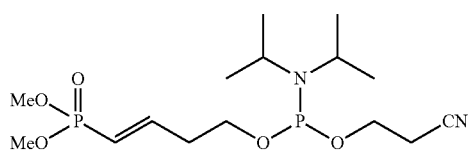

To a solution of dimethyl-(4-hydroxybut-1-en-1-yl)phosphonate (0.7 g, 3.8 mmol, 1 eq) in DCM (10 mL) was added diisopropylammonium tetrazolide (0.84 g) and 2-Cyanoethyl N,N,N,N-tetraisopropylphosphorodiamidite (1.9 g). The mixture was stirred at 0° C. for 1 hr, quenched by addition NaHCO$_3$ (20 mL), diluted with DCM (10 mL) and then extracted with DCM (10 mL×2). The combined organic layers were washed with brine (20 mL), dried over Na$_2$SO$_4$, filtered and concentrated under reduced pressure to give a residue which was purified by column chromatography (SiO$_2$, Petroleum ether/Ethyl acetate/TEA/DCM=10/1/0.5%/25% to 3/1/0.5%/25%), 2-cyanoethyl (4-(dimethoxyphosphoryl)but-3-en-1-yl) diisopropylphosphoramidite (0.3) was obtained as colorless oil. $^1$H NMR: 400 MHz, CD$_3$CN: δ ppm 6.7-7.9 (m, 1H), 5.75 (dd, 1H), 4.1-4.25 (m, 2H), 3.8-3.95 (m, 4H), 3.70-3.85 (m, 6H), 3.50-3.70 (m, 4H), 2.55-2.85 (m, 6H), 1.20-1.50 (m, 6H)

$^{31}$P NMR: 162 MHz, CDCl$_3$: δ ppm 147.81 (s, 1P), 31.39 (s, 1P).

Example 4: 2-cyanoethyl (5-(dimethoxyphosphoryl)pentyl)diisopropylphosphoramidite

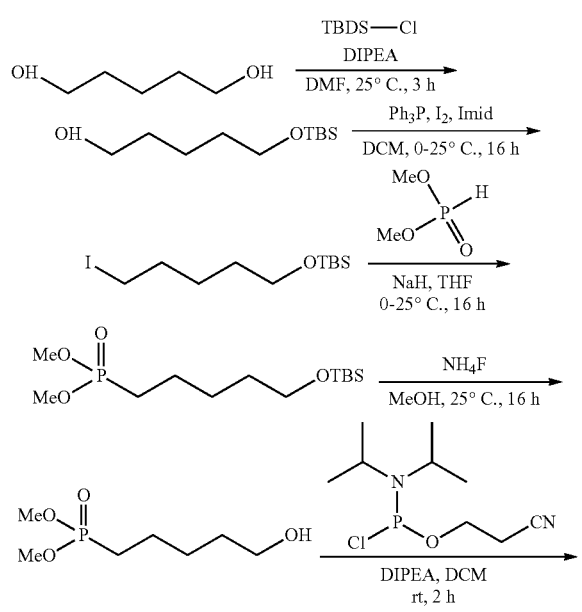

Step 4A: 5-((tert-butyldimethylsilyl)oxy)pentan-1-ol

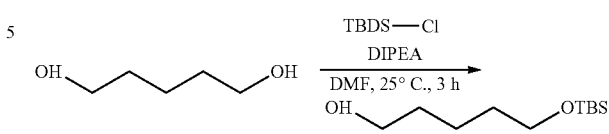

To a solution of pentane-1,5-diol (10.0 g, 96.0 mmol, 10.1 mL, 1.00 eq) in DMF (100 mL) was added DIPEA (124 g, 960 mmol, 167 mL, 10.0 eq) and TBSCl (15.2 g, 100 mmol, 12.3 mL, 1.05 eq). The mixture was stirred at 25° C. for 16 h. TLC (Petroleum ether/Ethyl acetate=5/1, product: R$_f$=0.43) indicated starting material was consumed completely. The reaction mixture was concentrated under reduced pressure, diluted with Ethyl acetate (200 mL) and washed with water (200 mL×3). The combined organic layers were washed with brine (400 mL), dried over Na$_2$SO$_4$, filtered and concentrated under reduced pressure to give a residue which was purified by column chromatography (SiO$_2$, Petroleum ether/Ethyl acetate=100/1 to 1/1). 5-((tert-butyldimethylsilyl)oxy)pentan-1-ol (11.5 g, 52.6 mmol, 54.8% yield) was obtained as a colorless oil.

$^1$H NMR: 400 MHz, CDCl$_3$: δ ppm 3.55-3.61 (m, 4H), 1.88 (s, 1H), 1.53-1.56 (m, 4H), 1.46-1.51 (m, 2H), 0.82-0.85 (m, 9H), 0.00-0.01 (m, 6H).

Step 4B: tert-butyl((5-iodopentyl)oxy)dimethylsilane

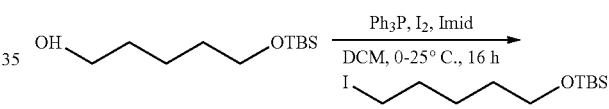

To a solution of Ph$_3$P (7.64 g, 29.1 mmol, 1.20 eq) in DCM (20.0 mL) was added imidazole (2.48 g, 36.4 mmol, 1.50 eq) and iodine (8.31 g, 32.7 mmol, 6.60 mL, 1.35 eq) at 0° C. 5-((tert-butyldimethylsilyl)oxy)pentan-1-ol (5.30 g, 24.2 mmol, 1 eq) in DCM (15.0 mL) was added dropwise to the mixture. The mixture was stirred at 25° C. for 16 h. TLC (Petroleum ether/Ethyl acetate=10/1, product: R$_f$=0.89) indicated starting material was consumed completely. The reaction mixture was concentrated under reduced pressure and purified by column chromatography (SiO$_2$, Petroleum ether/Ethyl acetate=1/0), tert-butyl((5-iodopentyl)oxy)dimethylsilane (7.00 g, 21.3 mmol, 87.8% yield) was obtained as a colorless oil.

$^1$H NMR: 400 MHz, CDCl$_3$: δ ppm 3.62 (t, J=6.2 Hz, 2H), 3.20 (t, J=7.0 Hz, 2H), 1.85 (q, J=7.2 Hz, 2H), 1.51-1.58 (m, 2H), 1.41-1.49 (m, 2H), 0.88-0.92 (m, 9H), 0.06 (d, J=0.8 Hz, 6H).

Step 4C: dimethyl (5-((tert-butyldimethylsilyl)oxy)pentyl)phosphonate

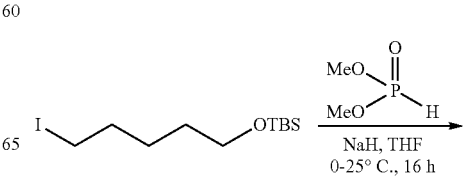

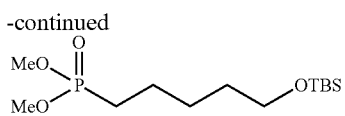

Under argon, in a three neck, round-bottomed flask was added successively NaH (792 mg, 19.8 mmol, 60% dispersion, 1.30 eq), THF (30.0 mL) and dimethyl phosphonate 2.18 g, 19.8 mmol, 1.82 mL, 1.30 eq) at 0° C. After stirring at 0° C. for 0.5 h. then at 70° C. for 1.5 h, tert-butyl((5-iodopentyl)oxy)dimethylsilane (5.00 g, 15.2 mmol, 1.00 eq) was introduced at 0° C. The reaction was stirred at 25° C. for 12 h. TLC (Petroleum ether: Ethyl acetate=1:1, product; $R_f$=0.43) indicated trace amounts of starting material and one new spot formed. The reaction mixture was quenched by addition NH$_4$Cl saturated aqueous solution (150 mL) at 0° C., and then extracted with DCM (300 mL×3). The combined organic layers were dried over Na$_2$SO$_4$ (30 g), filtered and concentrated under reduced pressure to give a residue which was purified by column chromatography (SiO$_2$, PMA, Petroleum ether: Ethyl acetate=100:1 to 1:1), dimethyl (5-((tert-butyldimethylsilyl)oxy)pentyl)phosphonate (2.00 g, 6.44 mmol, 42.3% yield) was obtained as light yellow oil.

Step 4D: dimethyl (5-hydroxypentyl)phosphonate

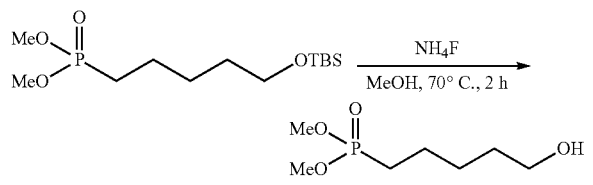

To a solution of dimethyl (5-((tert-butyldimethylsilyl)oxy)pentyl)phosphonate (1.80 g, 5.80 mmol, 1.00 eq) in methanol (20.0 mL) was added NH$_4$F (644 mg, 17.4 mmol, 3 eq). The mixture was stirred at 70° C. for 2 h. TLC (Petroleum ether/Ethyl acetate=0/1, product: $R_f$=0.04) indicated starting material was consumed completely. The reaction mixture was concentrated under reduced pressure to remove solvent. The residue was purified by column chromatography (SiO$_2$, KMnO$_4$Petroleum ether/Ethyl acetate=10/1 to 0:1). Dimethyl (5-hydroxypentyl)phosphonate (1.06 g, 5.13 mmol, 88.5% yield, 95.0% purity) was obtained as a colorless oil.

$^1$H NMR: 400 MHz, CDCl$_3$: δ ppm 3.72 (d, J=10.8 Hz, 6H), 3.63 (t, J=6.36 Hz, 2H), 1.69-1.80 (m, 2H) 1.60-1.69 (m, 2H) 1.52-1.60 (m, 2H) 1.41-1.50 (m, 2H).

Step 4E: 2-cyanoethyl (5-(dimethoxyphosphoryl)pentyl) diisopropylphosphoramidite

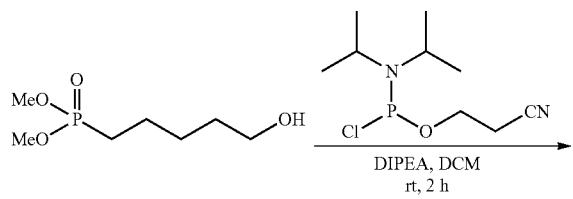

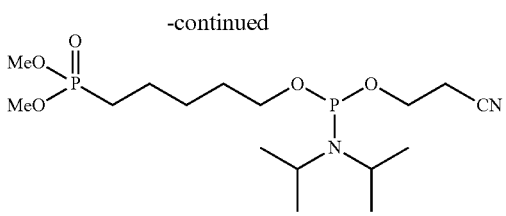

To a solution of dimethyl (5-hydroxypentyl)phosphonate (0.70 g, 3.57 mmol, 1.00 eq) in DCM (3.60 mL) was added DIPEA (1.84 g, 14.3 mmol, 2.49 mL, 4.00 eq) and 3-((chloro(diisopropylamino)phosphaneyl)oxy)propanenitrile (1.10 g, 4.64 mmol, 1.30 eq). The mixture was stirred at 0° C. for 1 hr. TLC (Petroleum ether/Ethyl acetate=0/1, product: $R_f$=0.43) indicated starting material was consumed completely. The reaction mixture was quenched by addition NaHCO$_3$ (20 mL), and then diluted with DCM (10 mL) and extracted with DCM (5 mL×2). The combined organic layers were washed with brine (20 mL), dried over Na$_2$SO$_4$, filtered and concentrated under reduced pressure to give a residue. The residue was purified by column chromatography (SiO$_2$, KMnO$_4$ Petroleum ether/Ethyl acetate/TEA/DCM=10/1/0.5%/25% to 3/1/0.5%/25%), 2-cyanoethyl (5-(dimethoxyphosphoryl)pentyl) diisopropylphosphoramidite (0.38 g, 910 umol, 25.5% yield, 95.0% purity) was obtained as colorless oil. $^1$H NMR: 400 MHz, CD$_3$CN: δ ppm 3.70-3.85 (m, 2H), 3.53-3.70 (m, 9H), 2.64 (t, J=6.0 Hz, 2H), 1.66-1.78 (m, 2H), 1.40-1.64 (m, 6H), 1.12-1.20 (m, 12H)

$^{31}$P NMR: 162 MHz, CD$_3$CN: δ ppm 146.93 (s, 1P), 34.24 (s, 1P).

Example 5: 2-cyanoethyl ((1s,4s)-4-((dimethoxyphosphoryl)methyl)cyclohexyl) diisopropylphosphoramidite

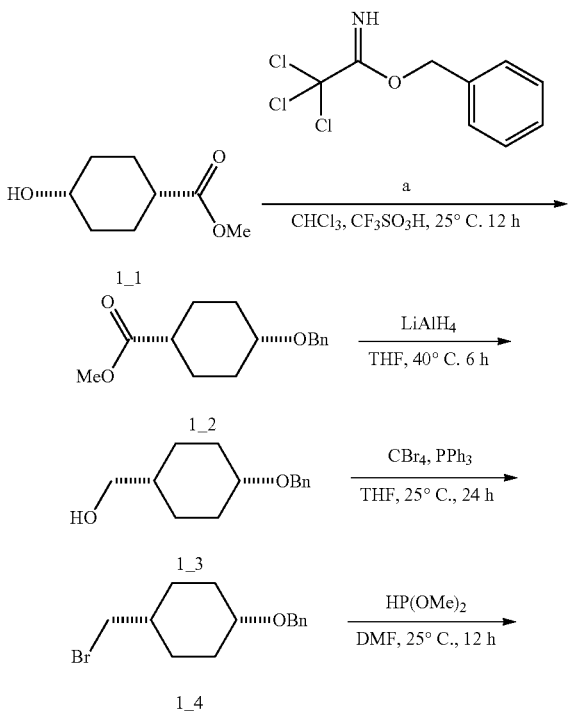

-continued

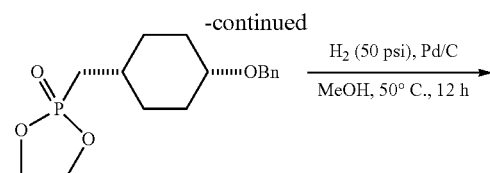

1_5

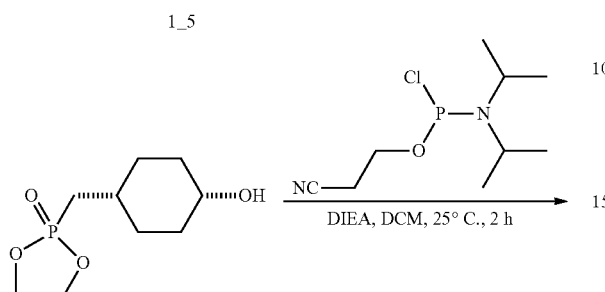

vp1

Step 5A: Synthesis of Compound 1_2

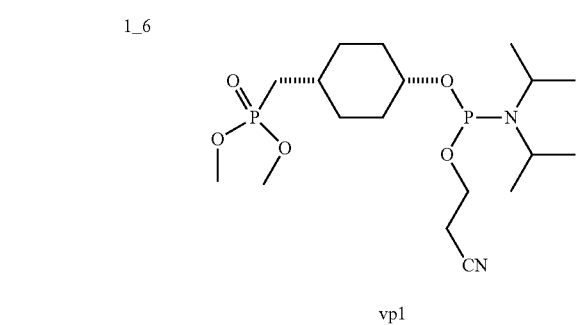

Compound 1_1 (10.0 g, 63.2 mmol, 1.00 eq) was added to CH$_3$Cl (20.0 mL) and Hexane (40.0 mL) at 25° C. Compound a (19.1 g, 75.8 mmol, 14.1 mL, 1.20 eq) and trifluoromethanesulfonic acid (1.42 g, 9.48 mmol, 837 uL, 0.15 eq) was added to the reaction at 25° C., and stirred for 12 hr at 25° C. TLC (Petroleum ether: Ethyl acetate=10:1, R$_f$=0.43) showed the reaction was completed. Diluted the reaction mixture with EtOAc (60.0 mL) and washed with saturated aqueous NaHCO$_3$ (60.0 mL), water (60.0 mL) and brine (60.0 mL). The organic layer was dried over anhydrous Na$_2$SO$_4$ and concentrated under reduced pressure. Purification by silica gel column (MPLC, PE/EA=30/1 to 10/1) provided compound 1_2 (10.5 g, 29.6 mmol, 46.8% yield, 70.0% purity) as yellow oil.

Step 5B: Synthesis of Compound 1_3

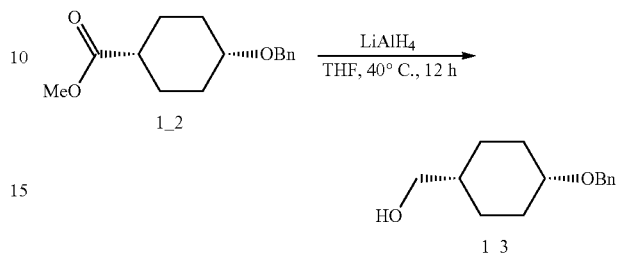

LiAlH$_4$ (1.60 g, 42.0 mmol, 1.10 eq) was taken in a vessel and cooled to vessel to 0° C. under nitrogen. THF (75.0 mL) was introduced to the vessel drop wise in the reaction at 0° C. Compound 1_2 (9.50 g, 38.2 mmol, 1.00 eq) in THF (20.0 mL) was added drop wise in the reaction at 0° C., and stirred for 12 h at 40° C. LCMS analysis indicated the completion of reaction. After cooling to 0° C., the water (20.0 mL) and 10% NaOH (20.0 mL) poured into the mixture phase extracted with ethyl acetate (75.0 mL), the combined org, extract was dried and evaporated. Obtain compound 1_3 (8.78 g, crude) as yellow oil and it was used in the next reaction without further purification.

Step 5C: Synthesis of Compound 1_4

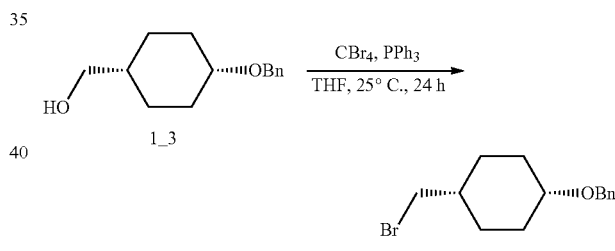

Compound 1_3 (8.43 g, 38.2 mmol, 1.00 eq) was dissolved in THF (40.0 mL) at 25° C. and cooled to 0° C. PPh$_3$ (13.0 g, 49.7 mmol, 1.30 eq) was added to the reaction at 0° C., and stirred for 10 min at 0° C. Added CBr$_4$ (16.5 g, 49.7 mmol, 1.30 eq) portion wise in the reaction at 0° C., and stirred for 24 h at 25° C. TLC (Petroleum ether: Ethyl acetate=10:1) showed the reaction completed. Filtered and washed with THF (2×20.0 mL) followed by EtOAc (2×20.0 mL). Purification by silica gel column (MPLC, PE/EA=30/1 to 10/1) provided compound 1_4 (7.58 g, 26.7 mmol, 69.9% yield) as yellow oil.

Step 5D: Synthesis of Compound 1_5

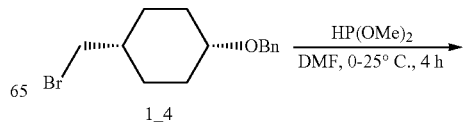

-continued

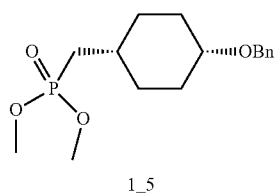

1_5

Sodium hydride (NaH, 1.02 g, 25.4 mmol, 60% purity, 6.00 eq) to DMF (6.00 mL) at 25° C., and cooled to 0° C. Methoxyphosphonoyloxymethane (3.26 g, 29.6 mmol, 2.72 mL, 7.00 eq) was added drop wise in the reaction at 0° C., and stirred for 30 min at 0° C. followed by stirring at 25° C. for 1.5 hr before cooling to 0° C. Added compound 1_4 (1.20 g, 4.24 mmol, and 1.00 eq) drop wise in the reaction at 0° C., and stirred for 4 h at 25° C. LCMS showed the reaction completed. Combined the three reactions. Cooled to 0° C. Quenched with aq.NH$_4$Cl (20.0 mL) and then extracted with EtOAc (2×20.0 mL), dried over Na$_2$SO$_4$, and concentrated to dryness. The residue was purified by prep-HPLC (neutral condition, column: Phenomenex Gemini-NX 80*30 mm*3 um; mobile phase: [Water-ACN]; B %: 30%-55%, 7 min). Compound 1_5 (2.02 g, 6.47 mmol, 50.8% yield) was obtained as yellow oil.

Step 5E: Synthesis of Compound 1_6

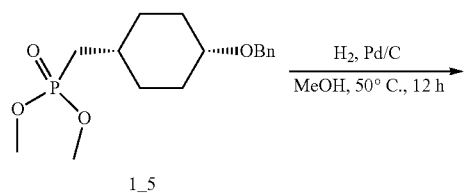

1_5

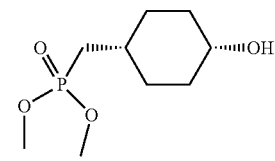

1_6

Compound 1_5 (0.7 g, 2.24 mmol, 1.00 eq) in taken in MeOH (3.00 mL) at 25° C., and Pd/C (0.50 g, 2.24 mmol, 10.0% purity) was added at 25° C. The vessel was flushed with hydrogen gas and stirred at 50° C. for 12 hr at 50 psi. LC-MS showed compound 1_5 was fully consumed. Several new peaks were shown on LC-MS and desired compound was detected. The reaction mixture was filtered and concentrated under reduced pressure to give a residue which was carried over to the next reaction without further purification. Compound 1_6 (0.45 g, 1.82 mmol, 81.3% yield, 90.0% purity) obtained as white oil.

Step 5F: Synthesis of Target vp1

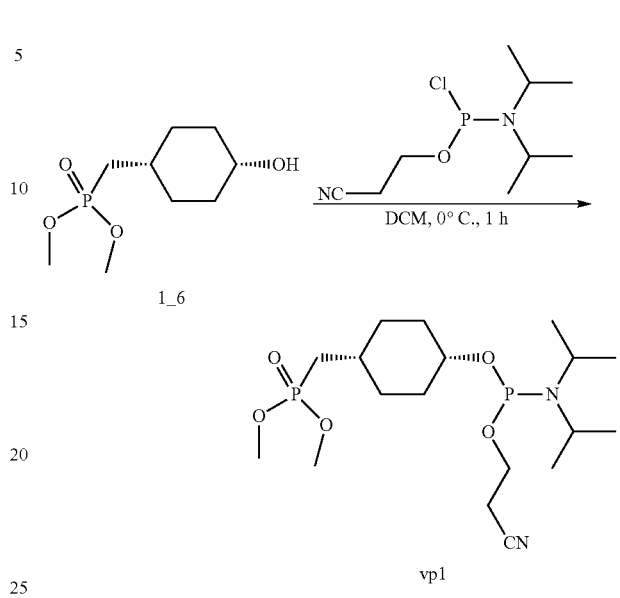

vp1

Compound 1_6 (0.45 g, 2.03 mmol, 1.00 eq) was dissolved in DCM (5.00 mL) at 0° C. and 3-[chloro-(diisopropylamino)phosphanyl]oxopropanenitrile (958 mg, 4.05 mmol, 2.00 eq) and DIEA (785 mg, 6.08 mmol, 1.06 mL, 3.00 eq) were added. The mixture was stirred at 0° C. for 1 hr. LC-MS showed compound 1_6 was not remained. Several new peaks were shown on LC-MS and desired compound was detected. The reaction mixture was diluted with DCM and extracted with NaHCO$_3$ (25.0 mL×2). The combined organic layers was dried over Na$_2$SO$_4$, filtered and concentrated under reduced pressure to give a residue. The residue was purified by prep-HPLC (neutral condition, column: Phenomenex Gemini-NX 80*30 mm*3 um; mobile phase: [Water-ACN]; B %: 30%-55%, 7 min). Compound vp1 (0.15 g, 248 umol, 12.2% yield, 70.0% purity) was obtained as a colorless oil and delivered.

Example 6: (E)-2-acetamido-4-(dimethoxyphosphoryl)but-3-en-1-yl (2-cyanoethyl) diisopropylphosphoramidite

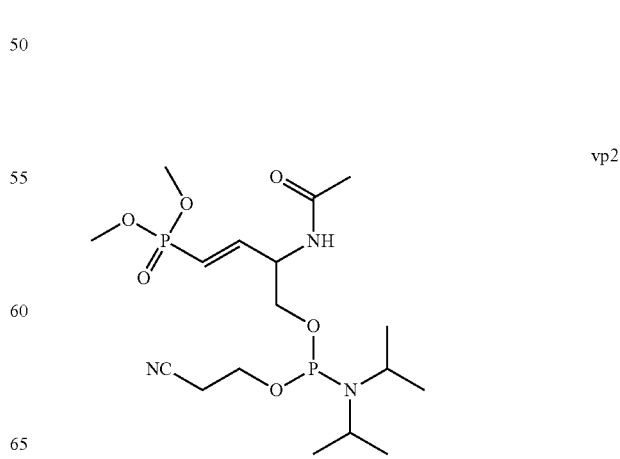

vp2

Synthesis Scheme for (E)-2-acetamido-4-(dimethoxyphosphoryl)but-3-en-1-yl (2-cyanoethyl) diisopropylphosphoramidite (vp2)

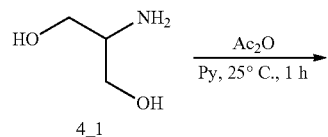

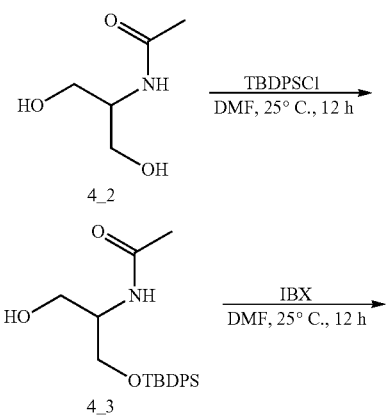

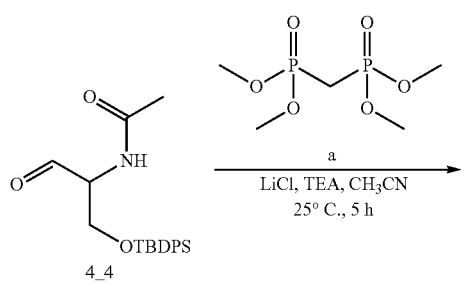

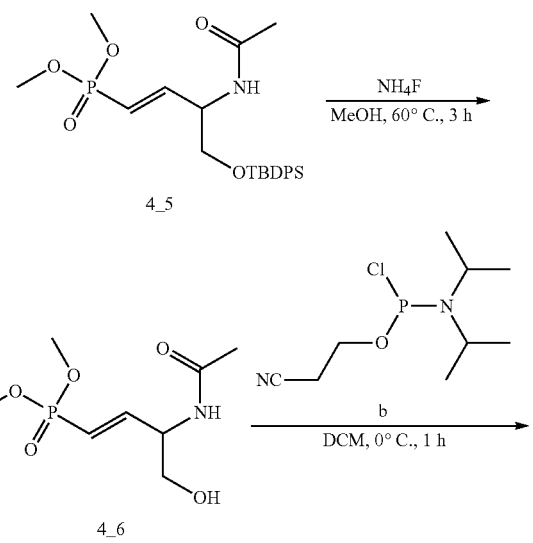

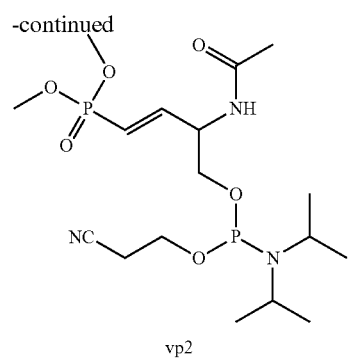

Step 6A: Synthesis of Compound 4_2

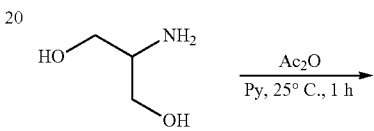

Compound 4_1 (20.0 g, 219 mmol, 1.00 eq) was added to a vessel containing Py (120 mL) at 25° C. Ac$_2$O (24.6 g, 241 mmol, 22.6 mL, 1.10 eq) was introduced dropwise in the reaction at 0° C., and then stirred for 1 h at 25° C. TLC (Dichloromethane:Methanol=5:1, Rf=0.35) showed the reaction completed. Concentrated the reaction mixture to dryness and dissolved in ethyl acetate (60 mL). A precipitate was formed after stirring for 10 min at 5° C. The precipitate was filtered and dried under vacuum. Compound 4_2 (25.1 g, 188 mmol, 85.9% yield) was obtained as white solid and it was used in the next reaction without further purification.

Step 6B: Synthesis of Compound 4_3

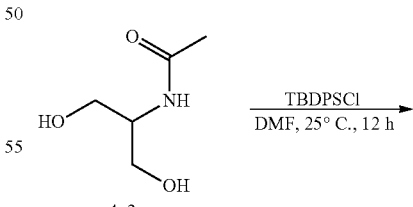

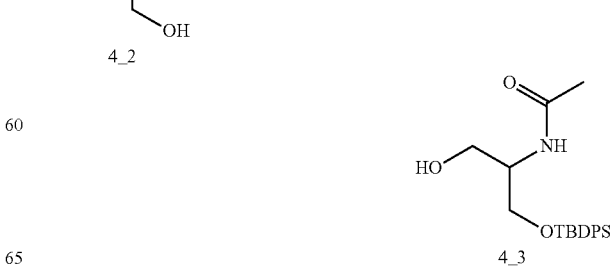

Compound 4_2 (25.0 g, 187 mmol, 1.00 eq) was dissolved in DMF (150 mL) at 25° C. and TBDPSCl (46.4 g, 168 mmol, 43.4 mL, 0.90 eq) and IMIDAZOLE (19.1 g, 281 mmol, 1.50 eq) were added. After stirring for 12 h at 25° C., TLC (Dichloromethane:Methanol=10:1, Rf=0.43), LCMS (ET31864-55-P1A1, RT=1.30 min) showed the reaction completed. Water (30 mL) was added and extracted with ethyl acetate (2×30 mL). Washed the combined organic layer with brine (3×20 mL), dried over $Na_2SO_4$, filtered and concentrated. Purification by silica gel column (MPLC, DCM/ME=30/1 to 10/1) afforded compound 4_3 (26.0 g, 69.9 mmol, 37.2% yield) as white solid.

Step 6C: Synthesis of Compound 4_4

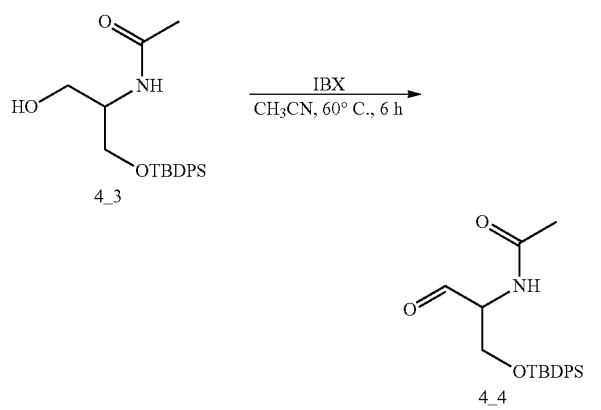

Compound 4_3 (7.00 g, 18.8 mmol, 1.00 eq) was dissolved in $CH_3CN$ (42 mL) at 25° C. and 2-iodylbenzoic acid (6.86 g, 24.4 mmol, 1.30 eq) was added. The reaction was stirred for 6 h at 60° C. TLC (Dichloromethane:Methanol=10:1, $R_f$=0.45), HPLC (RT=2.76 min), LCMS (RT=1.15 min) showed the reaction completed. Filtered and then extracted with $CH_3CN$ (2×20 mL), dried over $Na_2SO_4$, and concentrated to dryness to obtain compound 4_4 (8.00 g, crude) as yellow oil.

Step 6D: Synthesis of Compound 4_5

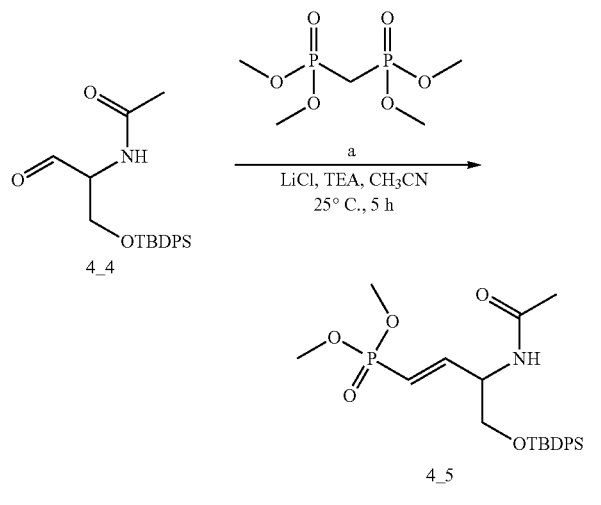

LiCl (1.15 g, 27.2 mmol, 1.44 eq) was taken in $CH_3CN$ (20 mL) at 25° C. before cooling the vessel to 0° C. Compound a (5.25 g, 22.6 mmol, 1.20 eq) was added drop wise in the reaction at 0° C. followed by the addition of TEA (2.52 g, 24.8 mmol, 3.46 mL, 1.32 eq) in $CH_3CN$ (10 mL) drop wise in the reaction at 0° C. Compound 4_4 (6.96 g, 18.8 mmol, 1.00 eq) in $CH_3CN$ (10 mL) was then added drop wise in the reaction at 0° C., and stirred for 5 h at 25° C. TLC (Dichloromethane:Methanol=10:1, $R_f$=0.49), LCMS and HPLC analysis showed the reaction completed. The reaction was quenched with aq.$NH_4Cl$ (20 mL) and then extracted with ethyl acetate (2×40 mL), dried over $Na_2SO_4$, and concentrated to dryness. Purification by silica gel column (MPLC, DCM/ME=30/1 to 10/1) provided compound 4_5 (2.22 g, 4.67 mmol, 24.7% yield) as yellow oil.

Step 6E: Synthesis of Compound 4_6

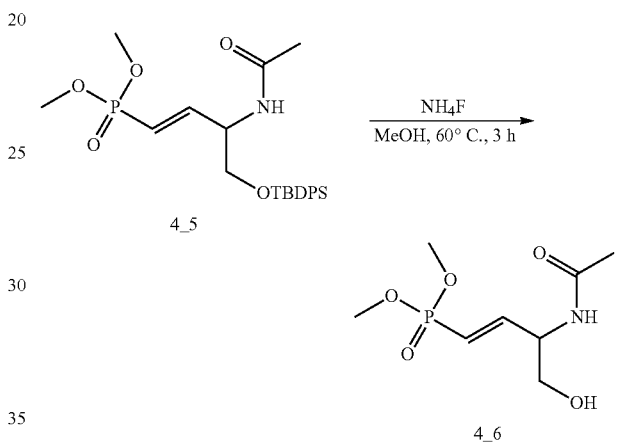

To a solution of compound 4_5 (0.90 g, 1.89 mmol, 1.00 eq) in MeOH (5 mL) was added $NH_4F$ (210 mg, 5.68 mmol, 3.00 eq) in the reaction at 25° C. The mixture was stirred at 60° C. for 3 hr. LC-MS analysis showed compound 4_5 was fully consumed and desired compound was detected. The reaction mixture was concentrated under reduced pressure to give a residue. The residue was purified by prep-HPLC (neutral condition, column: Agela DuraShell C18 250×25 mm×10 um; mobile phase: [water (10 mM $NH_4HCO_3$)-ACN]; B %: 0%-15%, 22 min). Obtained compound 4_6 (0.4 g, 1.52 mmol, 80.20% yield, 90.0% purity) as a white solid.

Step 6F: Synthesis of Compound vp2

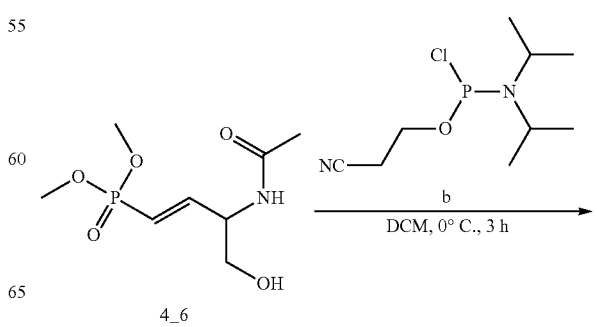

121

-continued

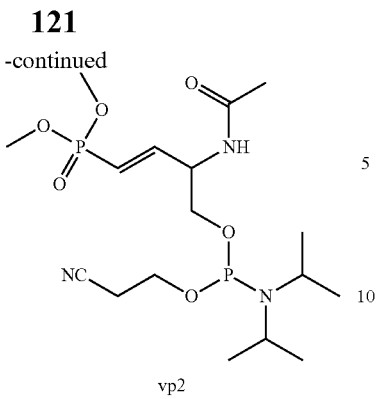

vp2

A solution of compound 4_6 (350 mg, 1.48 mmol, 1.00 eq) in DCM (2.10 mL) was cooled to 0° C., and compound b (698 mg, 2.95 mmol, 2.00 eq) and DIEA (572 mg, 4.43 mmol, 771 uL, 3.00 eq) were added and the mixture was stirred at 0° C. for 3 h. LC-MS analysis showed reactant was consumed completely and one main peak with desired mass was detected. The reaction mixture was washed with NaHCO$_3$, extracted with DCM 2 mL, dried over Na$_2$SO$_4$, filtered and concentrated under reduced pressure to give a residue. The residue was purified by prep-HPLC (column: Phenomenex Gemini-NX 150×30 mm×5 um; mobile phase: [Water-ACN]; B %: 15%-50%, 12 min). Compound vp2 (0.27 g, 556 umol, 37.7% yield, 90.0% purity) was obtained as a colorless oil.

Example 7: (E)-2-cyanoethyl (4-(dimethoxyphosphoryl)-2-(2-(2,4-dioxo-3,4-dihydroxypyrimidin-1 (2H)-yl)acetamido)but-3-en-1-yl) diisopropylphosphoramidite vpU3

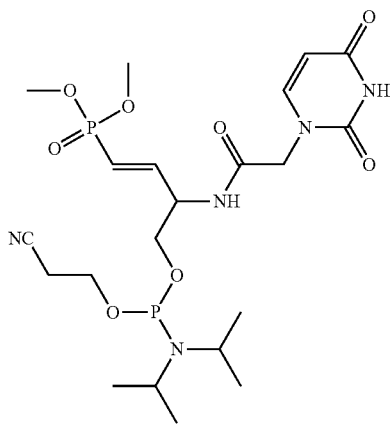

Synthesis Scheme for Compound vpU3

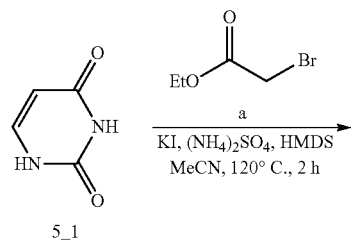

5_1

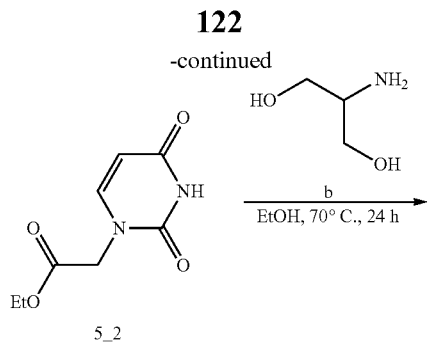

5_2

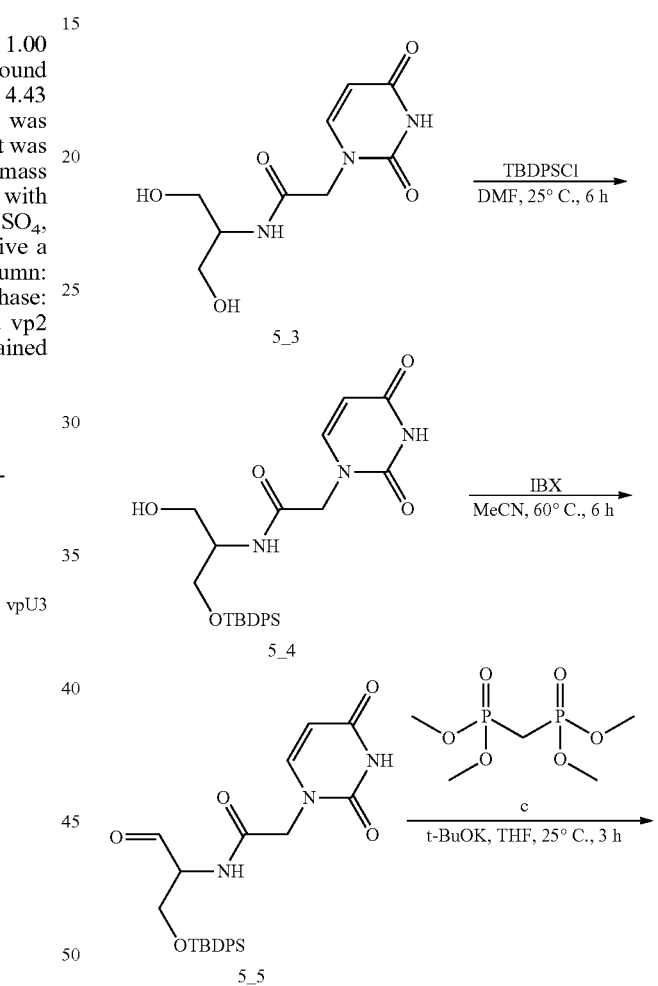

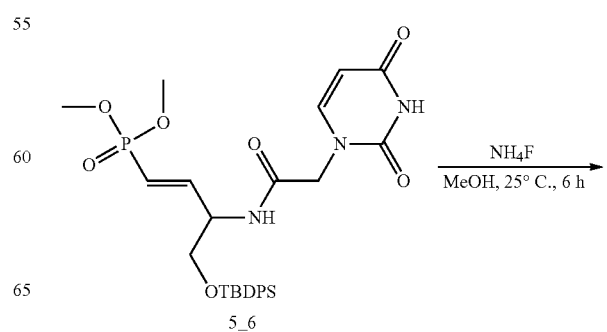

5_6

-continued

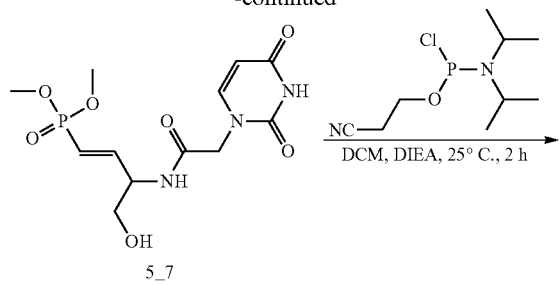

5_7

Step 7B: Synthesis of Compound 5_3

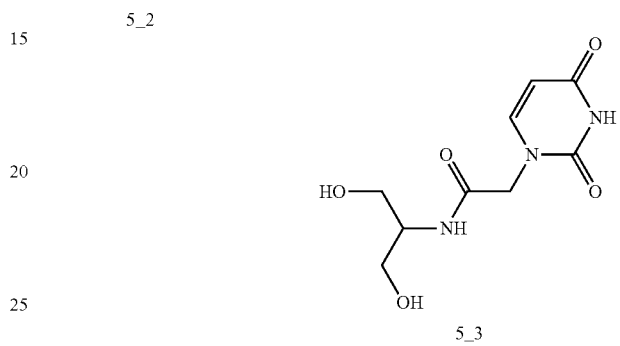

Dissolved compound 5_2 (15.9 g, 80.0 mmol, 1.00 eq) in EtOH (95.0 mL) and added compound b (8.02 g, 88.0 mmol, 1.10 eq) to the solution. The mixture was stirred at 70° C. for 24 h. LC-MS (ET31755-55-pla2) showed the reactant was consumed completely and one main peak with desired m/z or desired mass was detected. Cool the mixture to room temperature, then filtrate the mixture and collect the precipitate. Compound 5_3 (17.1 g, 66.8 mmol, 83.5% yield, 95.0% purity) was obtained as a white solid.

vpU3

Step 7A: Synthesis of Compound 5_2

Step 7C: Synthesis of Compound 5_4

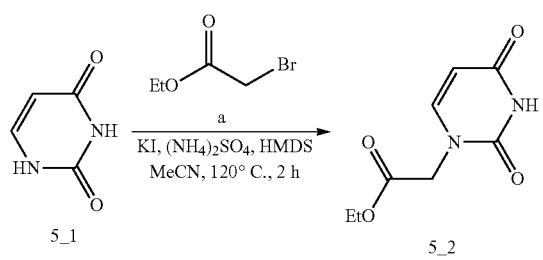

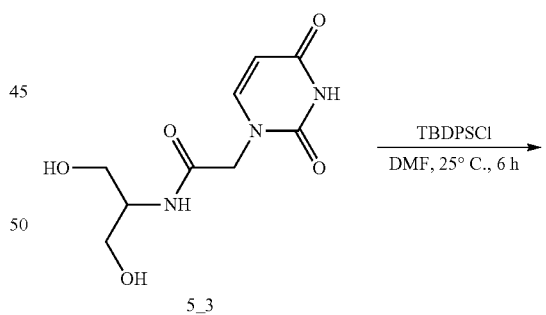

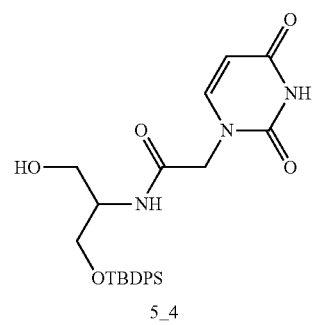

To a solution of compound 5_1 (5.00 g, 44.6 mmol, 1.00 eq) in MeCN (30.0 mL) was added ethyl 2-bromoacetate (17.9 g, 107 mmol, 11.8 mL, 2.40 eq), HMDS (4.32 g, 26.8 mmol, 5.61 mL, 0.60 eq). KI (3.70 g, 22.3 mmol, 0.50 eq) and ammonia; sulfuric acid (472 mg, 3.57 mmol, 266 uL, 0.08 eq) with stirred at 120° C. for 2 h. TLC (dichloromethane:methanol=10:1, $R_f$=0.63) showed the reaction was complete. To this mixture was added MeOH (20.0 mL) and concentrated under reduced pressure to remove solvent. The residue was purified by column chromatography. Compound 5_2 (7.00 g, 28.3 mmol, 63.6% yield, 80.0% purity) was obtained as a brown solid.

To a solution of compound 5_3 (17.0 g, 69.9 mmol, 1.0 eq) in DMF (102 mL) was added TBDPSCl (15.4 g, 55.9 mmol, 14.4 mL, 0.80 eq) and IMIDAZOLE (7.14 g, 105 mmol, 1.50 eq). The mixture was stirred at 25° C. for 6 h. LC-MS (ET31755-60-µl al) showed reactant was consumed completely and one main peak with desired m/z or desired mass was detected. To the mixture added water (120 mL) and extracted the solution with ethyl acetate (200 mL×2). The combined organic phase was washed with brine (400 mL×2), dried with anhydrous Na$_2$SO$_4$, filtered and concentrated in vacuum. The crude product was purified by recrystallization from DCM (300 mL) at 25° C. The rest crude product was purified by column chromatography (SiO$_2$, dichloromethane:methanol=10:1. R$_f$=0.43). Compound 5_4 (14.0 g, 26.2 mmol, 37.4% yield, 90.0% purity) was obtained as a white solid.

Step 7D: Synthesis of Compound 5_5

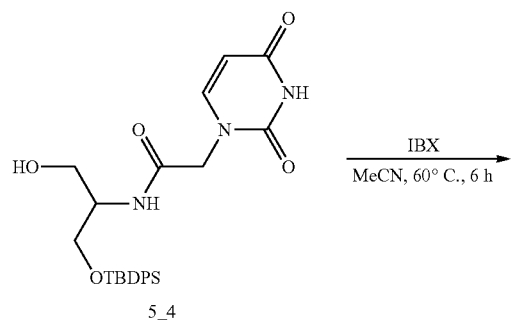

To a mixture of compound 5_4 (6.6 g, 13.7 mmol, 1.00 eq) in MeCN (45.0 mL) was added IBX (4.99 g, 17.8 mmol, 1.30 eq). The mixture was stirred at 60° C. for 6 h. TLC (petroleum ether:ethyl acetate=5:1, R$_f$=0.2) showed the reaction was complete. LC-MS showed reactant was consumed completely and one main peak with desired m/z was detected. Filtered the mixture, collected the solution and dried the solution under reduced pressure. The crude product was used into the next step without further purification. Compound 5_5 (7.0 g, crude) was obtained as a yellow gum.

Step 7E: Synthesis of Compound 5_6

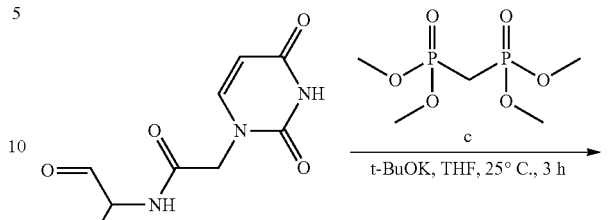

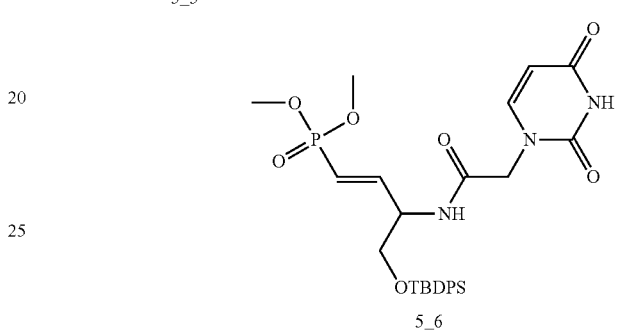

To a solution of compound c (3.50 g, 15.1 mmol, 1.10 eq) in THF (39.4 mL) was added t-BuOK (1 M, 13.7 mL, 1.00 eq). Compound 5_5 (6.57 g, 13.7 mmol, 1.00 eq) was added to the mixture when the solution became muddy. The mixture was stirred at 25° C. for 3 h. LC-MS (ET31755-79-pla1) showed reactant was consumed completely and one main peak with desired m/z or desired mass was detected. The reaction mixture was quenched by addition NH$_4$Cl 20.0 mL and extracted with EA (50.0 mL*2). The combined organic layers were washed with NaCl 100 mL, dried over NaSO4, filtered and concentrated under reduced pressure to give a residue. The residue was purified by column chromatography (SiO$_2$, dichloromethane:methanol=10:1, R$_f$=0.51). Compound 5_6 (1.80 g, 2.92 mmol, 21.3% yield, 95.0% purity) was obtained as a white solid.

Step 7F: Synthesis of Compound 5_7

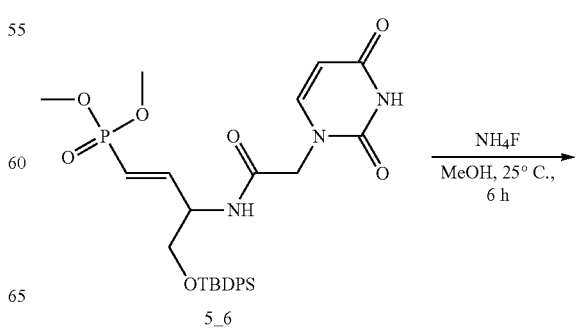

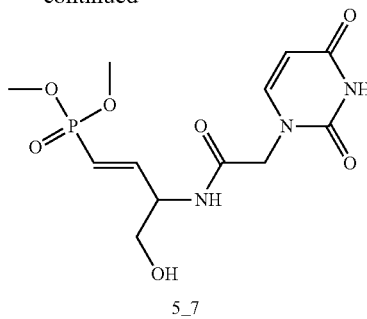

5_7

To a solution of compound 5_6 (0.8 g, 1.37 mmol, 1.0) eq) in MeOH (5.40 mL) was added NH₄F (151 mg, 4.10 mmol, 3.00 eq). The mixture was stirred at 60° C. for 6 h. LC-MS showed reactant was consumed completely and one main peak with desired m/z or desired mass was detected. The reaction mixture was concentrated under reduced pressure to give a residue. Filtered the mixture and collected the solution. The residue was purified by prep-HPLC (column: Agela DuraShell C18 250×70 mm×10 um; mobile phase: [water (10 mM NH₄HCO₃)-ACN]; B %: 1%-10%, 22 min). Compound 5_7 (0.38 g, 1.07 mmol, 78.5% yield, 98.0% purity) was obtained as a white solid.

Step 7F: Synthesis of Compound vpU3

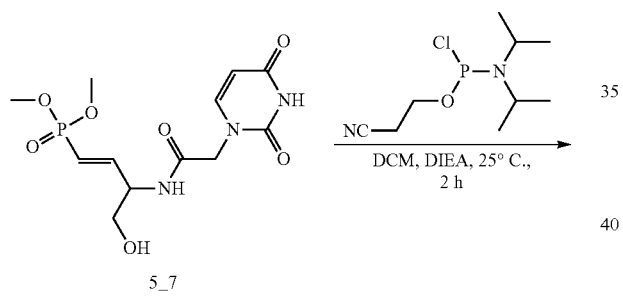

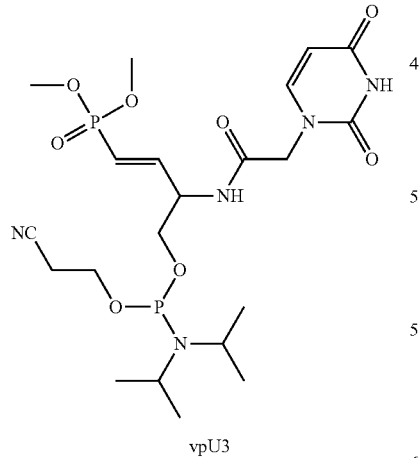

vpU3

To a solution of compound 5_7 (0.38 g, 1.09 mmol, 1.00 eq) in DCM (4.00 mL) was added compound d (517 mg, 2.19 mmol, 2.00 eq) and DIEA (424 mg, 3.28 mmol, 571 uL, 3.00 eq). The mixture was stirred at 25° C. for 2 h. LC-MS showed reactant was consumed completely and one main peak with desired m/z or desired mass was detected. The reaction mixture was washed with Na₂CO₃ and extracted with DCM 4.00 mL (2 mL×2), dried over Na₂SO₄, filtered and concentrated under reduced pressure to give a residue. The residue was purified by prep-HPLC (column: Phenomenex Gemini-NX 150×30 mm×5 um).

Example 7: 2-cyanoethyl ((3R,5S)-5-((E)-2-(dimethoxyphosphoryl)vinyl)-1-(2-(2,4-dioxo-3,4-dihydropyrimidin-1(2H)-yl)acetyl)pyrrolidin-3-yl) diisopropylphosphoramidite

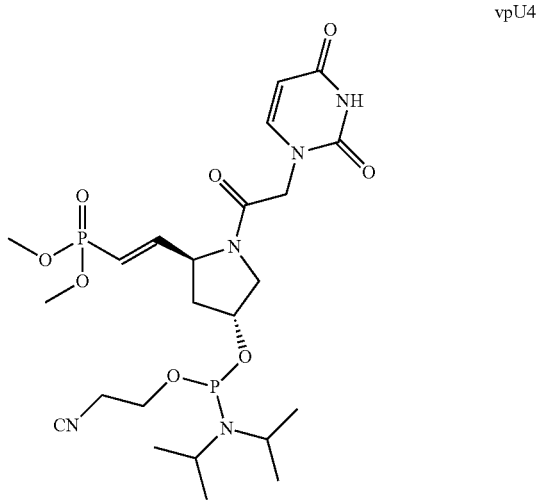

vpU4

Synthesis scheme for 2-cyanoethyl ((3R,5S)-5-((E)-2-(dimethoxyphosphoryl)vinyl)-1-(2-(2,4-dioxo-3,4-dihydropyrimidin-1(2H)-yl)acetyl)pyrrolidin-3-yl) diisopropylphosphoramidite (vpU4)

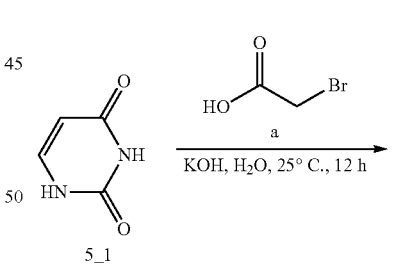

5_1

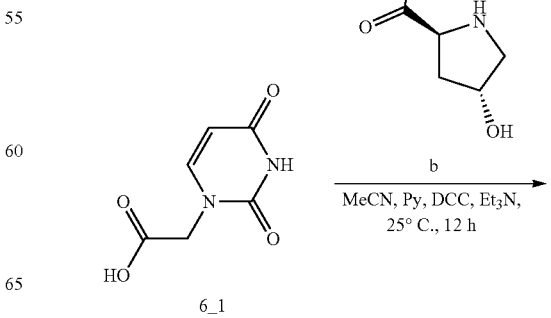

6_1

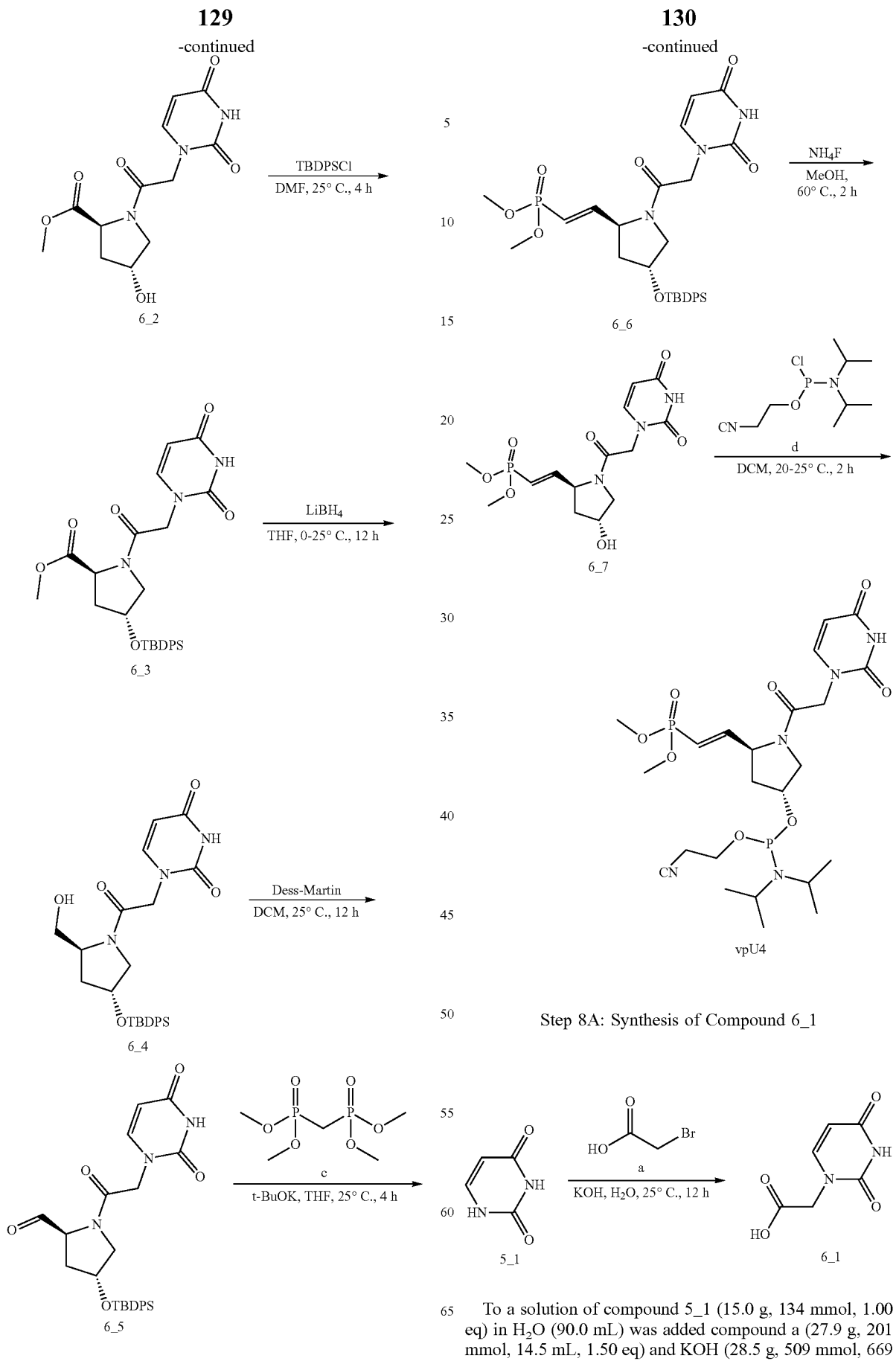
Step 8A: Synthesis of Compound 6_1
To a solution of compound 5_1 (15.0 g, 134 mmol, 1.00 eq) in H₂O (90.0 mL) was added compound a (27.9 g, 201 mmol, 14.5 mL, 1.50 eq) and KOH (28.5 g, 509 mmol, 669 mL, 3.80 eq). The mixture was stirred at 25° C. for 12 h. LC-MS showed reactant was consumed completely and one main peak with desired mass was detected. Adjust pH of the mixture to pH5 using 12 M HCl, cool the solution and the resulting precipitate was collected by filtration. Then the pH of the filtrate was adjusted to 2 and cooled. The resulting white precipitate was collected by filtration and dried under reduced pressure. Compound 6_1 (17.2 g, 96.1 mmol, 71.8% yield, 95.0% purity) was obtained as a white solid.

Step 8B: Synthesis of Compound 6_2

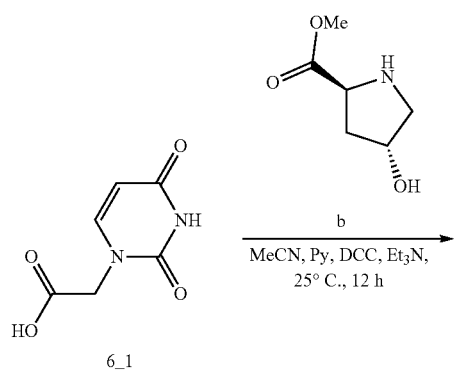

Step 8C: Synthesis of Compound 6_3

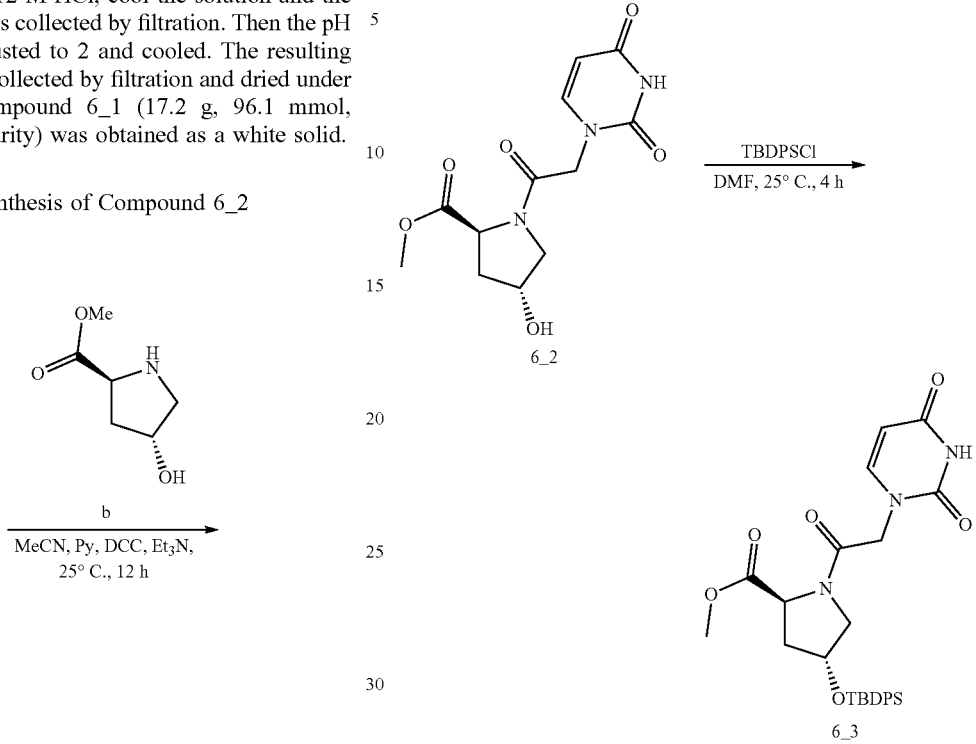

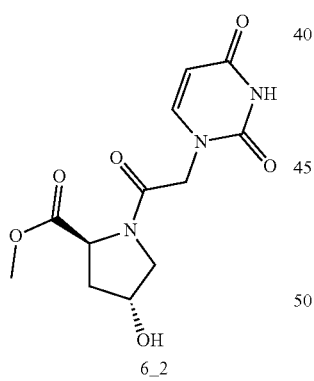

Dissolved compound b (16.70 g, 91.9 mmol, 0.92 eq) in MeCN (51.0 mL) and Py (51.0 mL), and to the solution added compound 6_1 (17.0 g, 99.9 mmol, 1.00 eq), Et$_3$N (10.1 g, 99.9 mmol, 13.9 mL, 1.00 eq) and DCC (24.7 g, 120 mmol, 24.3 mL, 1.20 eq). The mixture was stirred at 25° C. for 12 h. TLC (dichloromethane:methanol=5:1, R$_f$=0.29) indicated reactant was not remained, and one major new spot with lower polarity was detected. The reaction mixture was quenched by addition H$_2$O 70.0 mL, filtered the mixture and collected the solution, and dried under reduced pressure to give a residue. Compound 6_2 (30.0 g, crude) was obtained as a yellow solid.

To a solution of compound 6_2 (29.7 g, 99.9 mmol, 1.00 eq) in DMF (178 mL) was added TBDPSCl (35.7 g, 130 mmol, 33.4 mL, 1.30 eq) and IMIDAZOLE (20.4 g, 300 mmol, 3.00 eq). The mixture was stirred at 25° C. for 4 h. TLC (dichloromethane:methanol=10:1, R$_f$=0.43) indicated reactant was not remained, and one major new spot with lower polarity was detected. Added ethyl acetate (200 mL) to the residue and washed with water (300 mL). The combined organic phase was washed with brine (400 mL*2), dried with anhydrous Na$_2$SO$_4$, filtered and concentrated in vacuum. The residue was purified by column chromatography (SiO$_2$, dichloromethane:methanol=100:1 to 50:1). Compound 6_3 (50.0 g, 88.7 mmol, 88.8% yield, 95.0% purity) was obtained as a yellow solid.

Step 8D: Synthesis of Compound 6_4

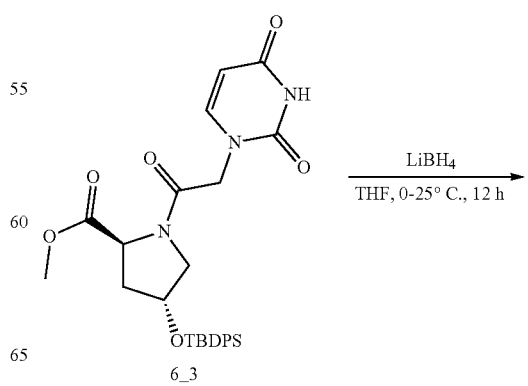

-continued

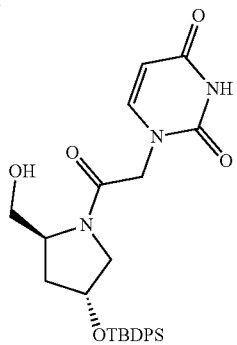
6_4

To a mixture of compound 6_3 (20.0 g, 37.3 mmol, 1.00 eq) in THF (120 mL) was added LiBH$_4$ (1.63 g, 74.7 mmol, 2.00 eq). The mixture was stirred at 25° C. for 12 h. LC-MS (ET31755-66-P1 A1) showed reactant was consumed completely and one main peak with desired m/z was detected. The reaction mixture was quenched by addition NH$_4$Cl 30.0 mL at 0° C., and then diluted with 1 M HCl 60.0 mL until pH 7 and extracted with ethyl acetate (150 mL×2). The combined organic layers were washed with NaCl 300 mL, dried over Na$_2$SO$_4$, filtered and concentrated under reduced pressure to give a residue. The residue was purified by column chromatography (SiO$_2$, dichloromethane:methanol=100:1 to 25:1). Compound 6_4 (9.67 g, 15.24 mmol, 40.81% yield, 80% purity) was obtained as a light yellow solid.

Step 8E: Synthesis of Compound 6_5

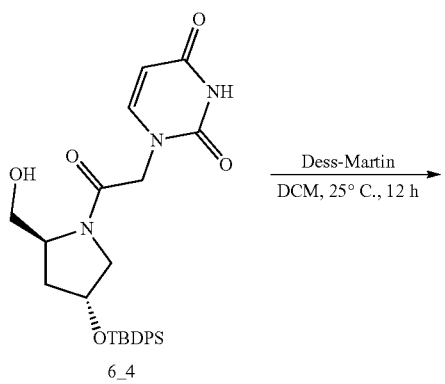
6_4

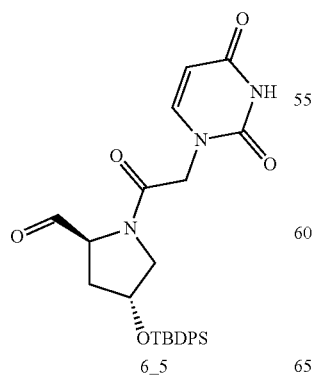
6_5

To a solution of compound 6_4 (8.14 g, 16.0 mmol, 1.00 eq) in DCM (48.0 mL) was added Dess-Martin (8.16 g, 19.2 mmol, 5.96 mL, 1.20 eq). The mixture was stirred at 15° C. for 12 h. LC-MS showed reactant was consumed completely and one main peak with desired m/z or desired mass was detected. Filtered the mixture and collected the solution for three times and dried the solution under reduced pressure to give a residue. Compound 6_5 (7.27 g, crude) was obtained as a yellow solid.

Step 8F: Synthesis of Compound 6_6

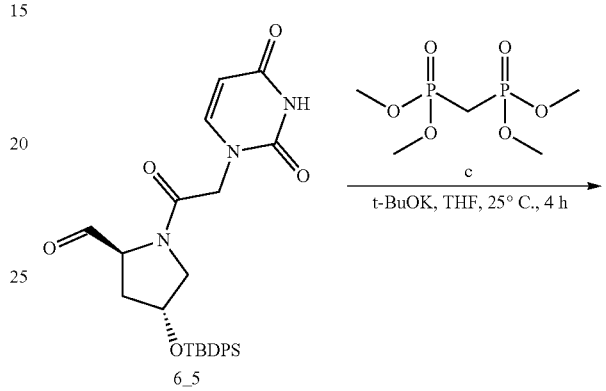

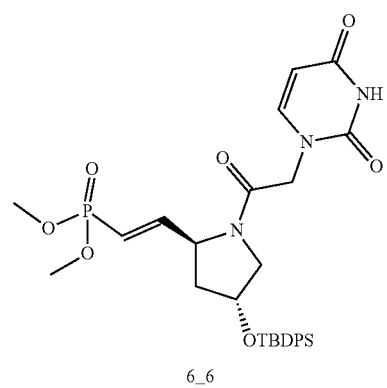
6_6

To a solution of compound c (3.66 g, 15.8 mmol, 1.10 eq) in THF (43.0 mL) was added t-BuOK (1 M, 14.3 mL, 1.00 eq). Compound 6_5 (7.24 g, 14.32 mmol, 1 eq) was added in the mixture when the solution became muddy. The mixture was stirred at 0-25° C. for 5 h. LC-MS showed reactant was consumed completely and one main peak with desired m/z or desired mass was detected. Quenched with aq.NH$_4$Cl (4.00 mL) and then extracted with ethyl acetate (2×4 mL), dried over Na$_2$SO$_4$, and concentrated to dryness. The residue was purified by column chromatography (SiO$_2$, dichloromethane:methanol=10:1). Compound 6_6 (0.88 g, 1.22 mmol, 8.54% yield, 85.0% purity) was obtained as a white solid.

Step 8G: Synthesis of Compound 6_7

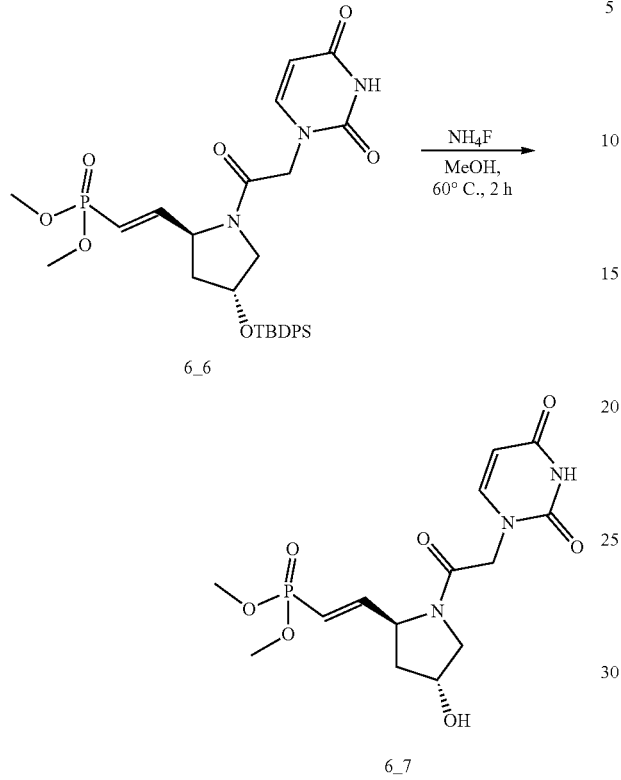

To a solution of compound 6_6 (1.33 g, 2.17 mmol, 1.00 eq) in MeOH (7.90 mL) was added NH₄F (242 mg, 6.52 mmol, 3.00 eq). The mixture was stirred at 60° C. for 4 h. LC-MS showed reactant was consumed completely and one main peak with desired m/z or desired mass was detected. The reaction mixture was concentrated under reduced pressure to give a residue. Filtered the mixture and collected the solution. The residue was purified by prep-HPLC (column: Agela DuraShell C18 250×70 mm×10 um: mobile phase: [water (10 mM NH₄HCO₃)-ACN]; B %: 1%-10%, 22 min). Compound 6_7 (0.67 g, 1.62 mmol, 74.3% yield, 90.0% purity) was obtained as a colorless solid.

Step 8H: Synthesis of Compound vpU4

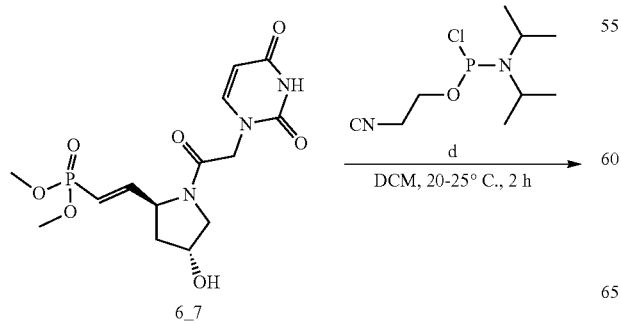

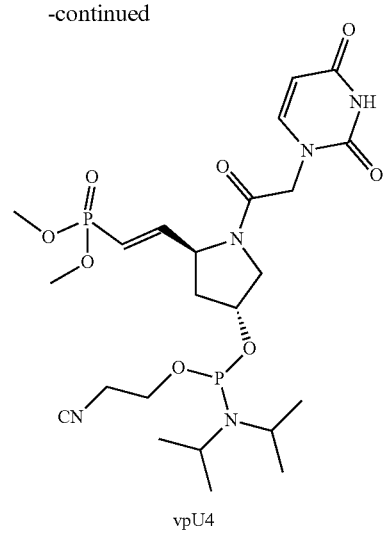

To a solution of compound 6_7 (0.23 g, 669.7 umol, 1.00 eq) in DCM 2.50 mL) was added DIEA (259.6 mg, 2.01 mmol, 349.9 uL, 3.00 eq) and compound d (317.0 mg, 1.34 mmol, 2.00 eq). The mixture was stirred at 0° C. for 2 hr. LC-MS showed compound 6_7 was not remained. Several new peaks were shown on LC-MS and desired compound was detected. The reaction mixture was quenched by addition NaHCO₃10 mL, and extracted with DCM (15 mL×2). The combined organic layers were dried over Na2SO4, filtered and concentrated under reduced pressure to give a residue. The residue was purified by column chromatography (SiO2, Ethyl acetate/acetone=100/1 to 5/1. Compound target 6 (0.15 g, 167.3 umol, 24.9% yield, 80.0% purity) was obtained as a white solid.

Example 9: 2-Cyanoethyl ((S)-6-(dimethoxyphosphoryl)hexan-2-yl) diisopropylphosphoramidite 2-Cyanoethyl ((S)-6-(dimethoxyphosphoryl)hexan-2-yl) diisopropylphosphoramidite is prepared from (S)-hexane-1,5-diol according to the following synthetic scheme.

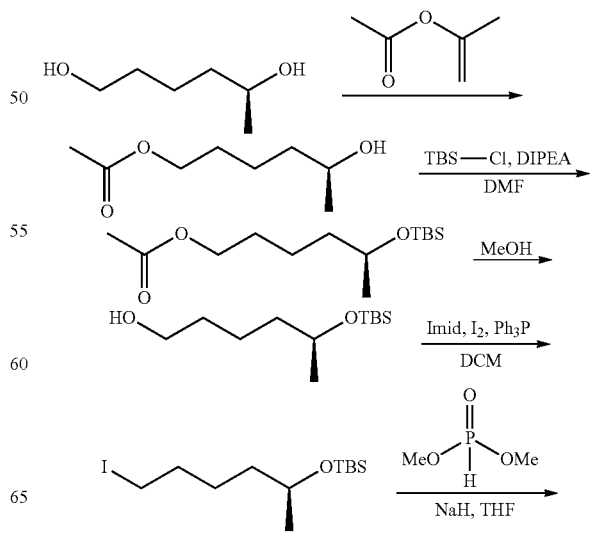

Example 10: 2-cyanoethyl (5-(dimethoxyphosphoryl)-3-methoxypentyl) diisopropylphosphoramidite 2-cyanoethyl (5-(dimethoxyphosphoryl)-3-methoxypentyl) diisopropylphosphoramidite is prepared from 3-methoxypentane-1,5-diol according to the following synthetic scheme.

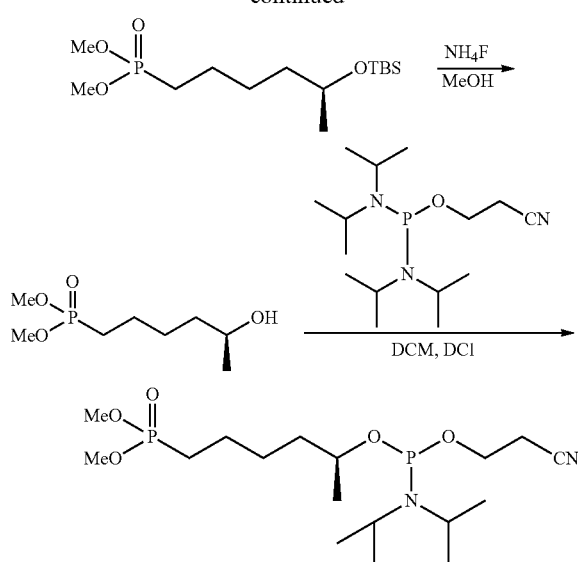
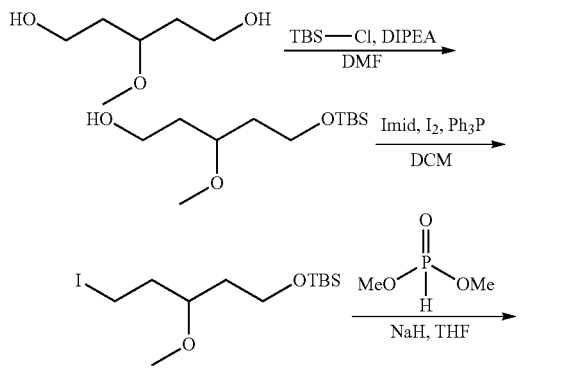
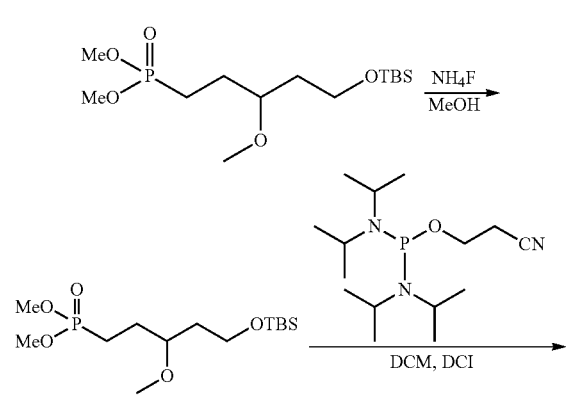

Example 11: 2-Cyanoethyl(2-(2-(dimethoxyphosphoryl)ethoxy)ethyl) diisopropy phosphoramidite Cyanoethyl(2-(2-(dimethoxyphosphoryl)ethoxy)ethyl) diisopropy phosphoramidite is prepared from diethylene glycol according to the following synthetic scheme.

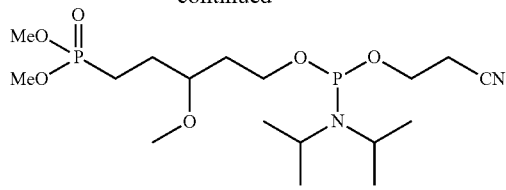
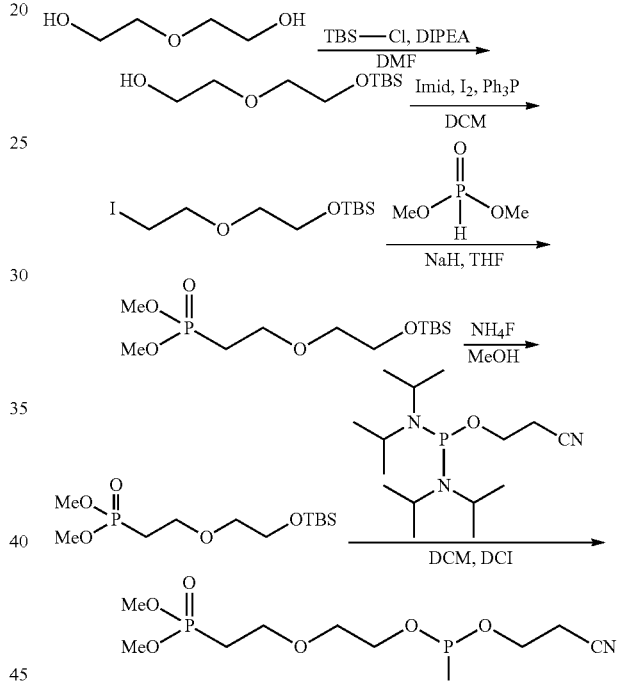

Example 12: 2-Cyanoethyl (24(2-(dimethoxyphosphoryl)ethyl)thio)ethyl) diisopropylphosphoramidite 2-Cyanoethyl (2-((2-(dimethoxyphosphoryl)ethyl)thio)ethyl) diisopropylphosphoramidite is prepared from 2,2'-thiobis(ethan-1-ol) according to the following synthetic scheme.

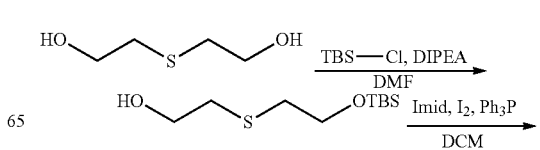

-continued

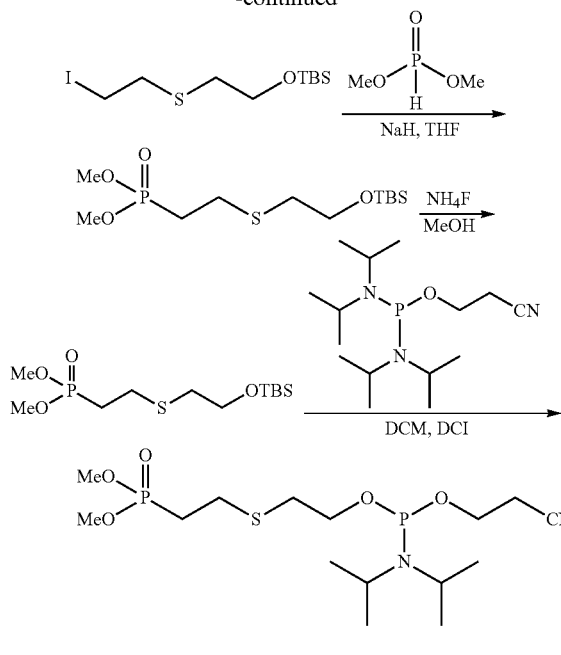

Example 13: 2-cyanoethyl (2-((2-(dimethoxyphosphoryl)ethyl-2,2-d2)thio)ethyl-1,1-d2) diisopropylphosphoramidite 2-cyanoethyl (2-((2-(dimethoxyphosphoryl)ethyl-2,2-d2)thio)ethyl-1,1-d2) diisopropylphosphoramidite is prepared from 2,2'-thiobis(ethan-1,1-d2-1-ol) according to the following synthetic scheme.

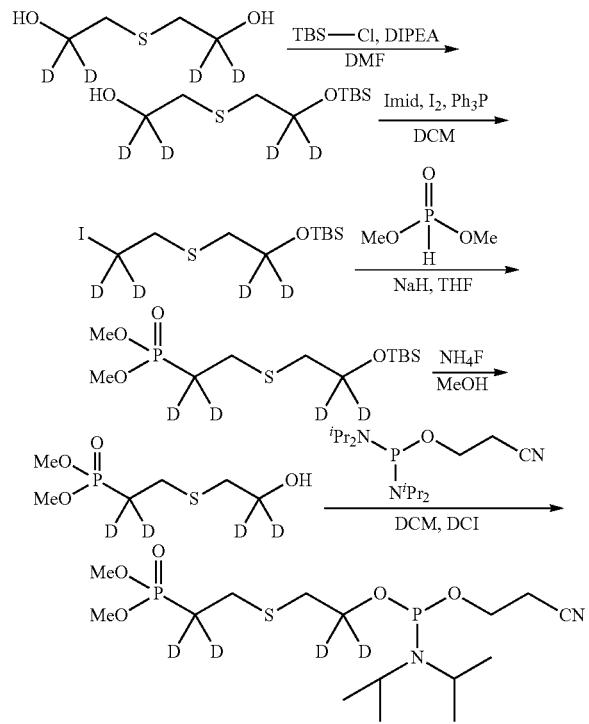

Example 14: 2-Cyanoethyl (24(2-(dimethoxyphosphoryl)ethyl)(methyl)amino)ethyl) diisopropylphosphoramidite Cyanoethyl (2-((2-(dimethoxyphosphoryl)ethyl)(methyl)amino)ethyl) diisopropylphosphoramidite is prepared from 2,2'-(methylazanediyl)bis(ethan-1-ol) according to the following synthetic scheme.

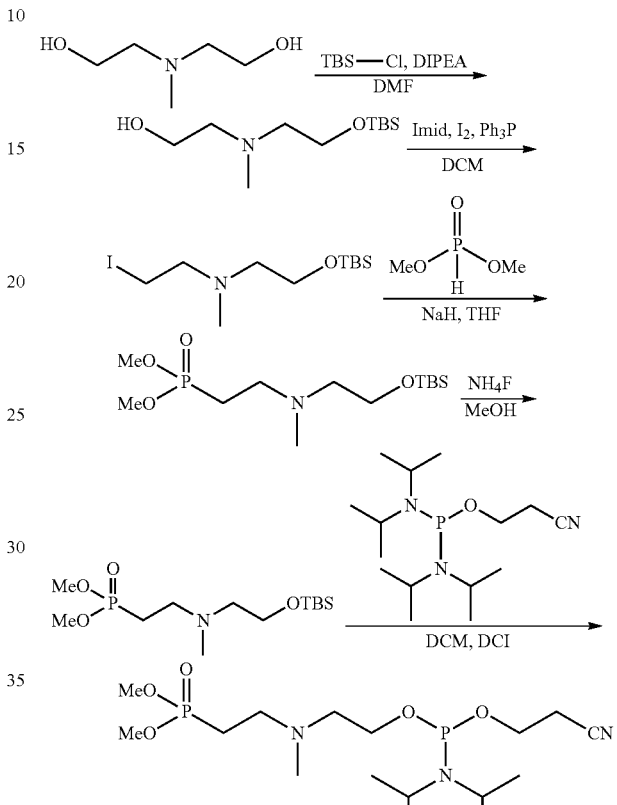

Example 15: 2-Cyanoethyl (4-(2-(dimethoxyphosphoryl)ethylcyclohexyl) diisopropylphosphoramidite 2-Cyanoethyl (4-(2-(dimethoxyphosphoryl)ethyl)cyclohexyl) diisopropylphosphoramidite is prepared from 4-vinylcyclohex-1-ene according to the following synthetic scheme.

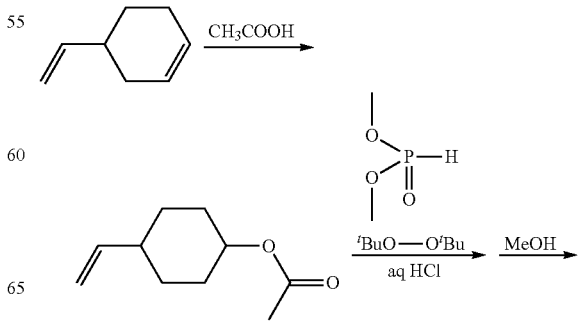

141
-continued

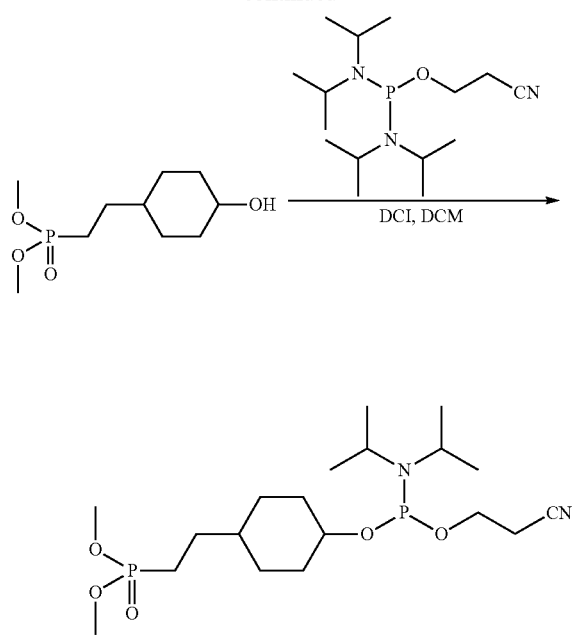

Example 16: 2-Cyanoethyl ((4-(dimethoxyphosphoryl)cyclohexyl)methyl) diisopropylphosphoramidite 2-Cyanoethyl ((4-(dimethoxyphosphoryl)cyclohexyl) methyl) diisopropylphosphoramidite is prepared from 4-(Hydroxymethyl)cyclohexanol according to the following synthetic scheme

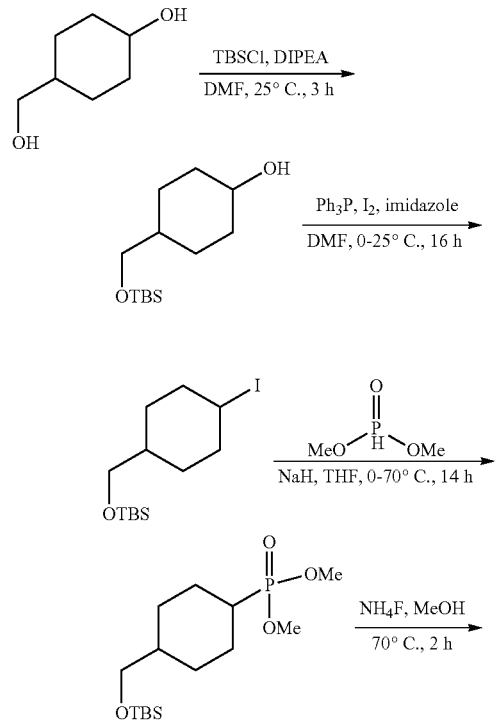

142
-continued

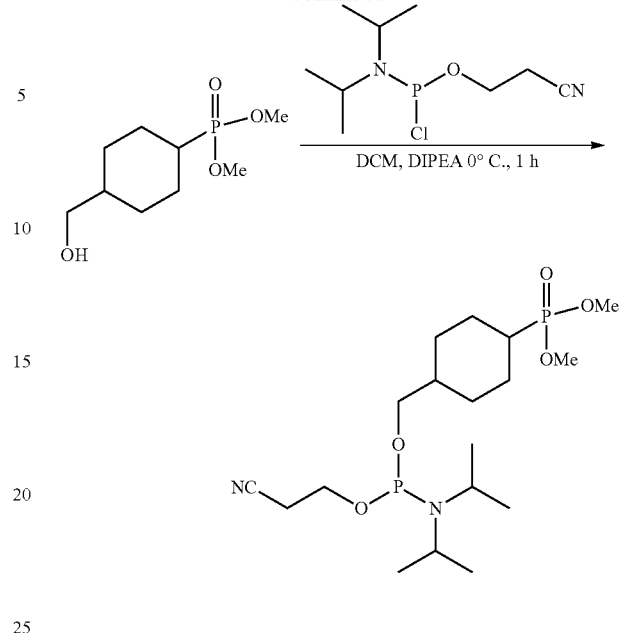

Example 17: 2-Cyanoethyl ((3S,6S)-6-(3-(dimethoxyphosphoryl)propyl)-3,6-dihydro-2H-pyran-3-yl) diisopropylphosphoramidite 2-Cyanoethyl ((3S,6S)-6-(3-(dimethoxyphosphoryl)propyl)-3,6-dihydro-2H-pyran-3-yl) diisopropylphosphoramidite is prepared from (3S,6S)-6-allyl-3,6-dihydro-2H-pyran-3-yl acetate according to the following synthetic scheme.

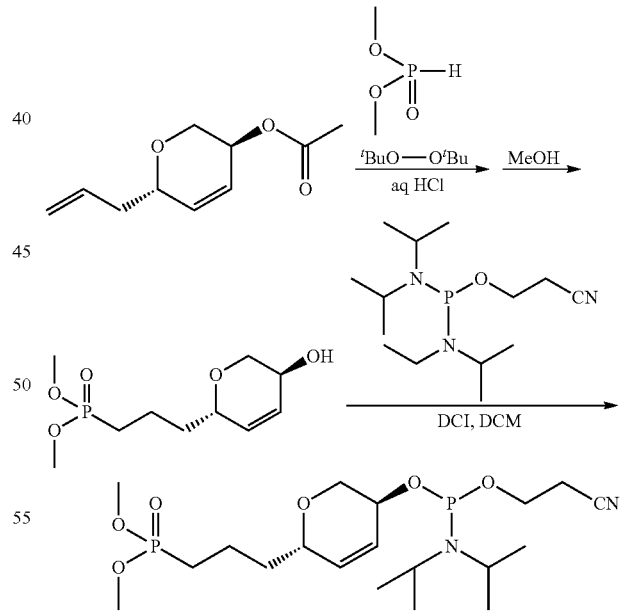

Example 14: 2-Cyanoethyl (4-(2-(dimethoxyphosphoryl)ethyl)benzyl) diisopropylphosphoramidite 2-Cyanoethyl (4-(2-(dimethoxyphosphoryl)ethyl)benzyl) diisopropylphosphoramidite is prepared from 4-vinylbenzyl acetate according to the following synthetic scheme.

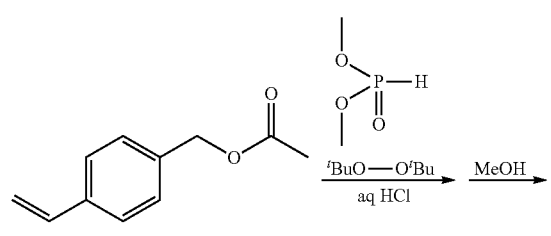

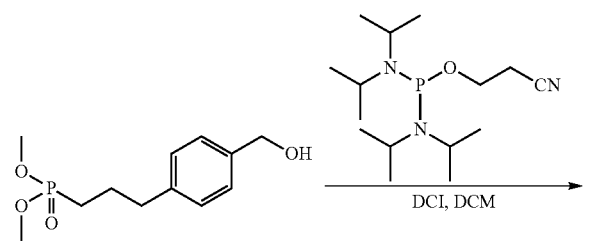

Example 18: 2-Cyanoethyl (4-((dimethoxyphosphoryl)methyl)benzyl) diisopropylphosphoramidite 2-Cyanoethyl (4-((dimethoxyphosphoryl)methyl)benzyl) diisopropylphosphoramidite is prepared from 4-(iodomethyl)benzyl acetate according to the following synthetic scheme.

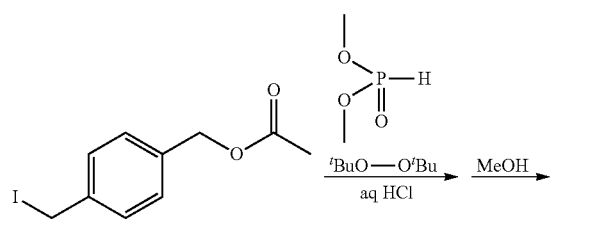

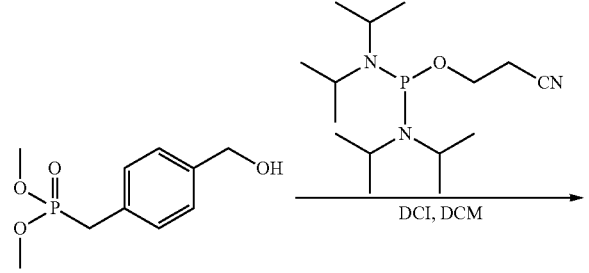

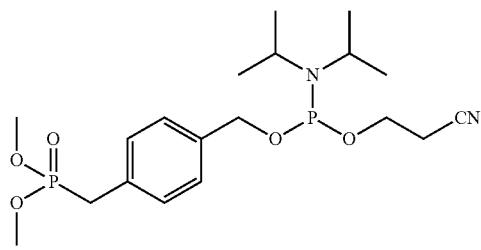

Example 19: 2-Cyanoethyl (4-((dimethoxyphosphoryl)methyl)cyclohexyl) diisopropyl phosphoramidite Cyanoethyl (4-((dimethoxyphosphoryl)methyl)cyclohexyl) diisopropyl phosphoramidite is prepared from tert-butyl-(cyclohex-3-en-1-ylmethoxy)dimethylsilane according to the following synthetic scheme.

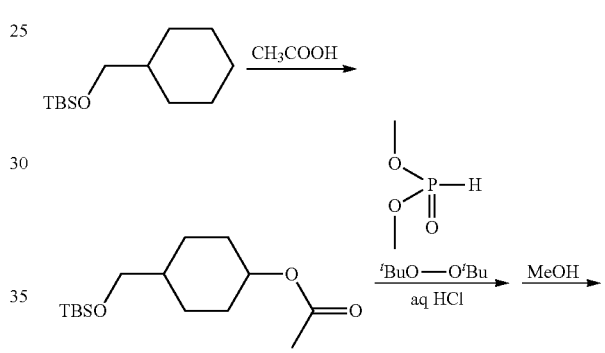

Example 20: (E)-2-Cyanoethyl (4-(2-(dimethoxyphosphoryl)vinyl)benzyl) diisopropylphosphoramidite (E)-2-Cyanoethyl (4-(2-(dimethoxyphosphoryl)vinyl)benzyl) diisopropylphosphoramidite is prepared from 4-(hydroxymethyl)benzaldehyde according to the following synthetic scheme.

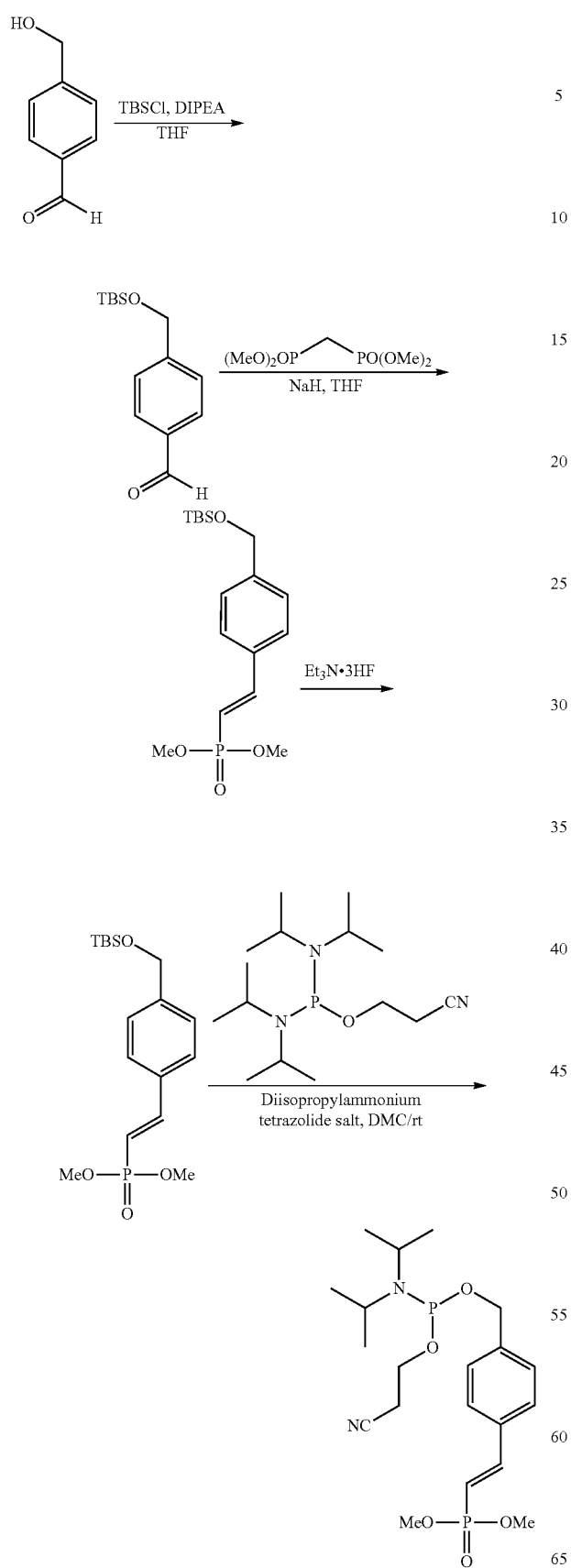
Example 21: dimethyl (E)-(5-((bis(diisopropylamino)phosphaneyl)oxy)pent-1-en-1-yl)phosphonate
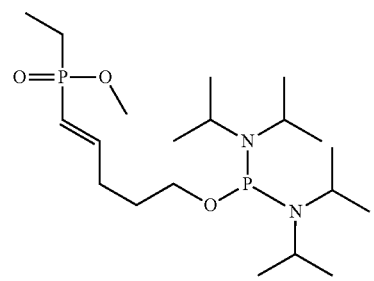 [SMILES: CCP(=O)(/C=C/CCCOP(N(C(C)C)C(C)C)N(C(C)C)C(C)C)OC]
Example 22: dimethyl ((4-((bis(diisopropylamino)phosphanevl)oxy)cyclohexvl)methyl)phosphonate
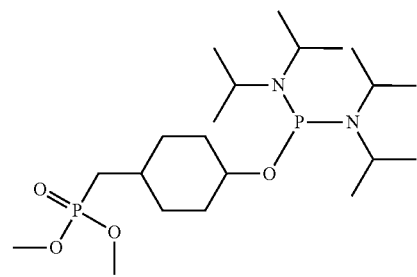 [SMILES: COP(=O)(CC1CCC(OP(N(C(C)C)C(C)C)N(C(C)C)C(C)C)CC1)OC]
Examples 23: dimethyl (3-((bis(diisopropylamino)phosphaneyl)oxy)phenethyl)phosphonate
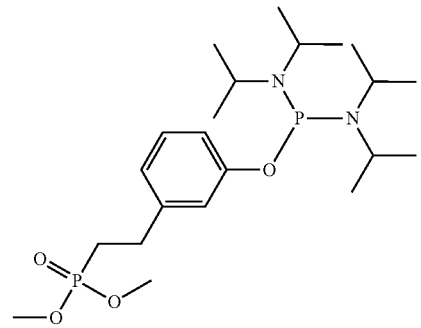 [SMILES: COP(=O)(CCc1cccc(OP(N(C(C)C)C(C)C)N(C(C)C)C(C)C)c1)OC]

Example 24: dimethyl (2 ((bis(diisopropylamino)phosphaneyl)oxy)phenethyl)phosphonate

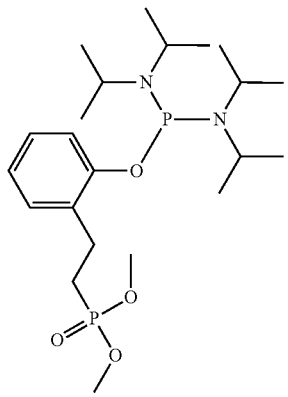 [SMILES: COP(=O)(CCc1ccccc1OP(N(C(C)C)C(C)C)N(C(C)C)C(C)C)OC]

Example 25: dimethyl (E)-2 ((bis(diisopropylamino)phosphaneyl)oxy)styryl)phosphonate

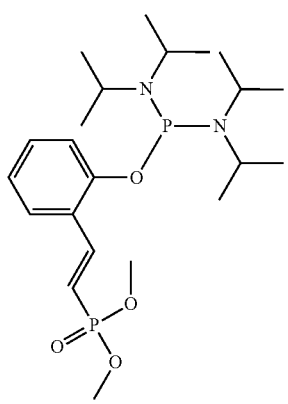 [SMILES: COP(=O)(/C=C/c1ccccc1OP(N(C(C)C)C(C)C)N(C(C)C)C(C)C)OC]

Example 26: 2-cyanoethyl (2-((2-(dimethoxyphosphoryl)ethyl)amino)ethyl) diisopropylphosphoramidite

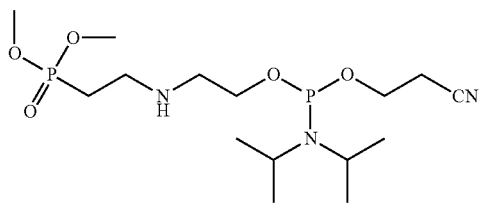 [SMILES: COP(=O)(CCNCCOP(OCCC#N)N(C(C)C)C(C)C)OC]

Example 27: 2-cyanoethyl (2-((2-(dimethoxyphosphoryl)ethyl)amino)ethyl) diisopropylphosphoramidite

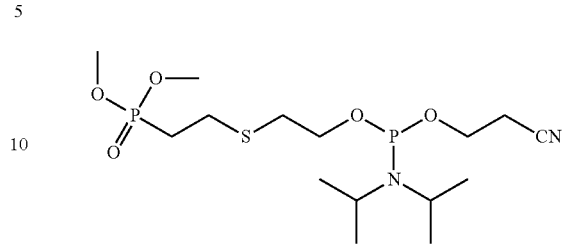

Example 28: 2-cyanoethyl (2-(2-(dimethoxyphosphoryl)ethoxy)ethyl) diisopropylphosphoramidite

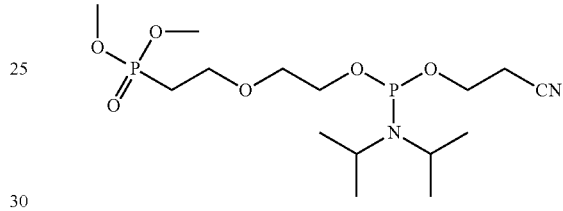

Example 28: 2-cyanoethyl (4-((dimethoxyphosphoryl)methyl)cyclohexyl)ethyl(isopropyl)phosphoramidate

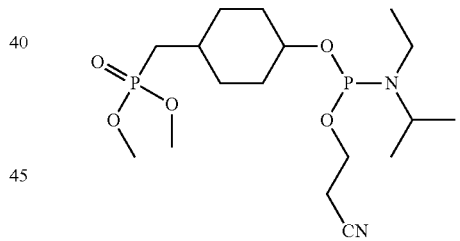

Example 29: 2-cyanoethyl (4-((dimethoxyphosphoryl)methyl)benzyl) diisopropylphosphoramidite

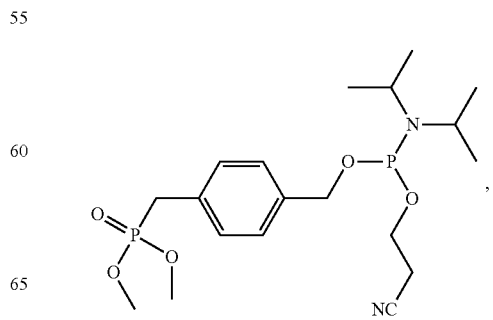

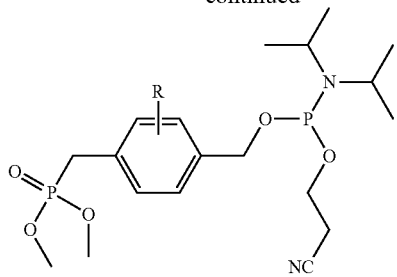

Example 30: Linear Stable Phosphates Substitutions

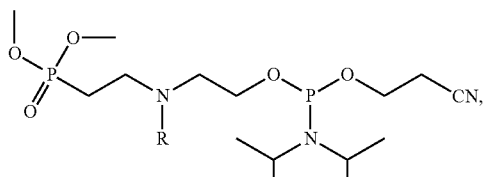

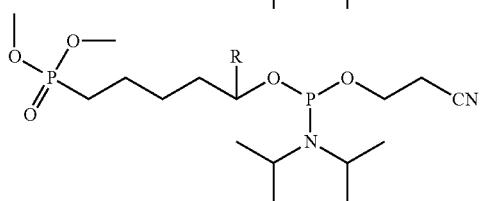

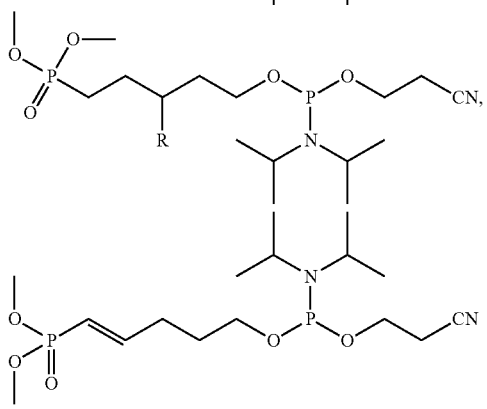

Examples of Alternative Internucleotide Linkages

Example 31: Amide Linkage

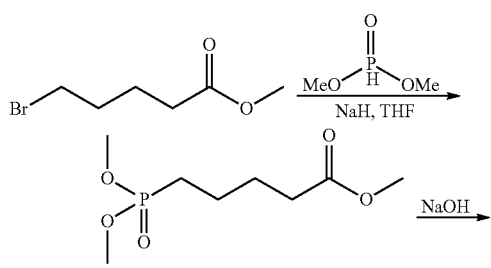

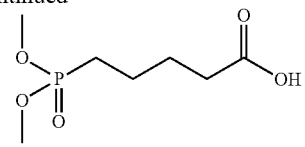

Example 32: Amide Linkage

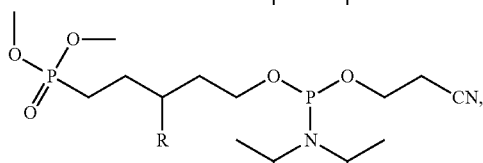

Example 33: Methylphosphonate Linkage

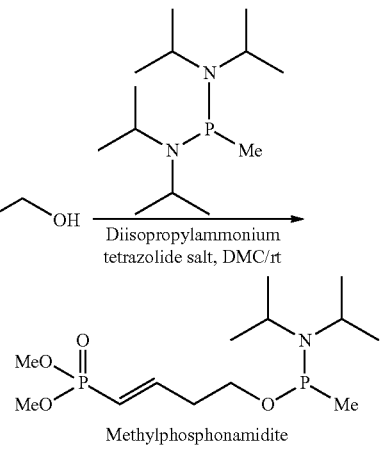

Methylphosphonamidite

Molecular Biology Examples

Example 1. In Vitro Activity of Phosphonates in HCT116 Cells siRNA design and synthesis: A 21mer SSB guide strand was designed against mouse SSB. The sequence (5' to 3') of the guide/antisense strand was UUACAUUAAAGUCU-GUUGUUU. Three versions were made incorporating phosphonate modified nucleotide structures (compounds 1, 2 and 4). The guide and fully complementary RNA passenger strands were assembled on solid phase using standard phospharamidite chemistry, and purified over HPLC. The Base, sugar and phosphate modifications that are well described in the field of RNAi were used to optimize the potency of the duplex and reduce immunogenicity. Purified single strands were duplexed to get the double stranded siRNA described above.

MSTN sequence: The sequence (5' to 3') of the guide/antisense strand was UUAUUAUUUGUUCUUUGCCUU. The guide and fully complementary RNA passenger strands were assembled same as described above.

In vitro study: The different siRNAs were transfected into human colorectal carcinoma HCT116 cells at 100 nM, 10 nM, 1 nM, 0.1 nM, 0.01 nM, 0.001 nM, and 0.0001 nM final concentration. The siRNAs were formulated with commercially available transfection reagent. Lipofectamine RNAiMAX (Life Technologies), according to the manufacturer's "forward transfection" instructions. Cells were plated 24 h prior to transfection in triplicate on 24-well tissue culture plates, with 50000 cells per well. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with SSB-specific and PPIB-specific TaqMan gene expression probes (Thermo Fisher) using TaqMan® Fast Advanced Master Mix (Applied Biosystems). SSB values were normalized within each sample to PPIB gene expression. The quantification of SSB downregulation was performed using the standard $2^{-\Delta\Delta Ct}$ method. All experiments were performed in triplicate, vpUm.SSB.7f8s was used as a control.

$IC_{50}$ values were as follows:

TABLE 2

| | IC50 (pM) | | |
|---|---|---|---|
| Sample | HCT116 | DM1 Ctrl Myoblasts | SJCRH30 |
| vpUm.SSB.7f8s | 4.00 | 11.9 | 14.2 |
| 2, vpUe.MSTN.7f8s | 0.13 | 13.7 | 26.5 |
| 1, vpUh.MSTN.7f8s | 8.41 | 42.2 | 19.4 |
| 4, vpUk.MSTN.7f8s | 2.36 | 17.2 | 24.1 |

Figure 2A:
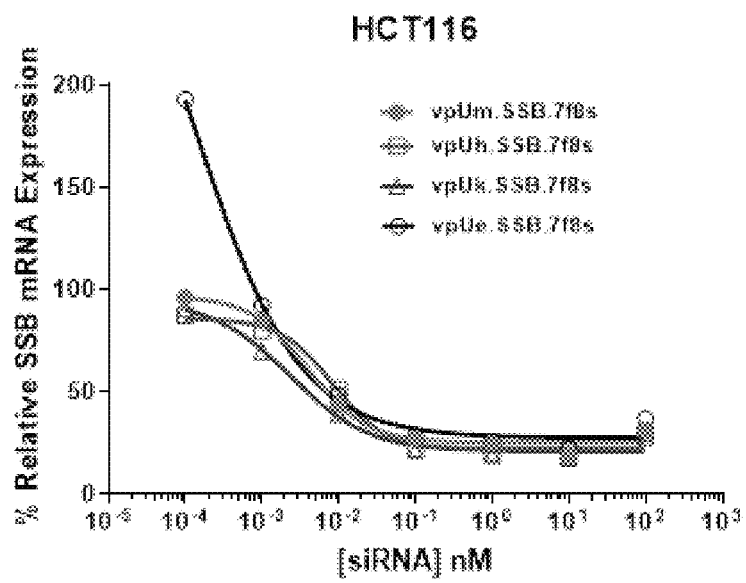
FIG. 2A-C show graphs of relative % SSB mRNA levels in various types of cells.
Figure 2B:
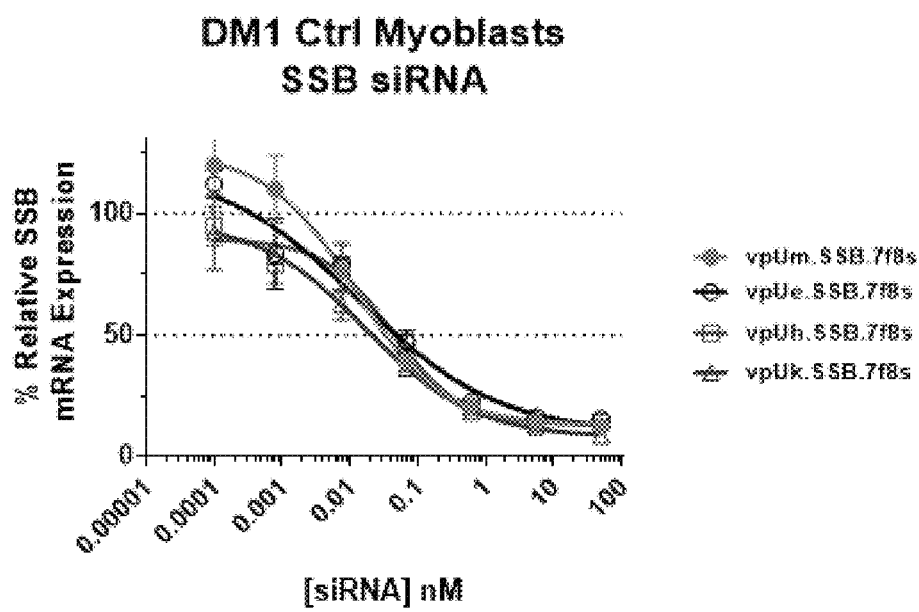
Figure 2C:
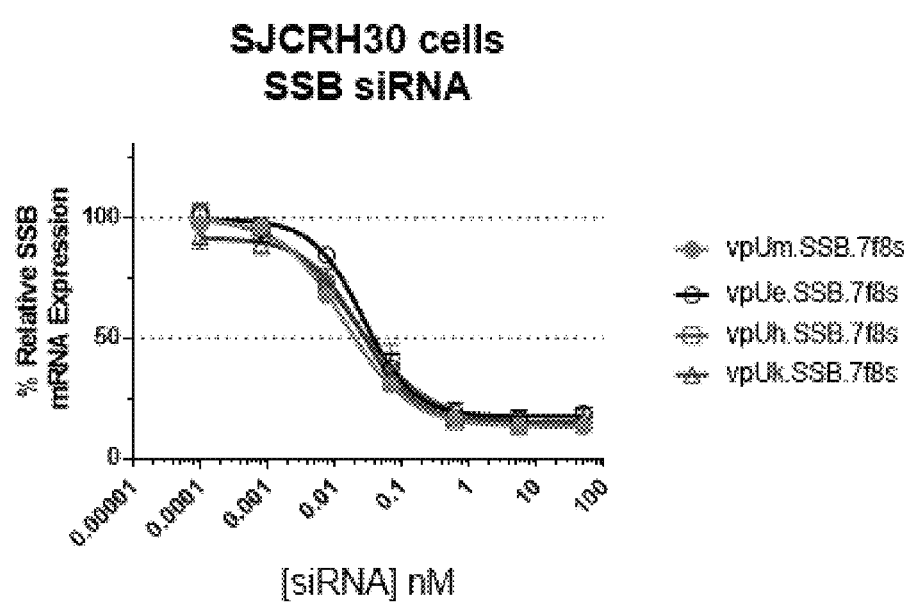
Figure 3A:
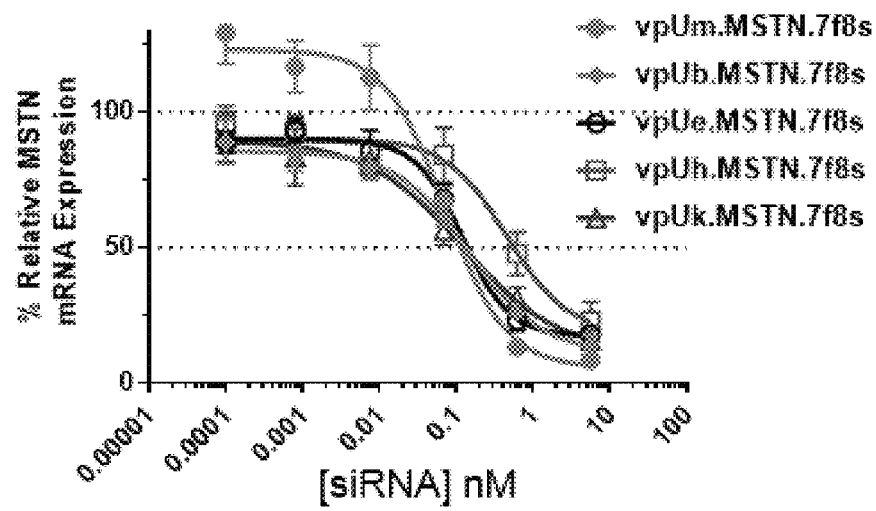
FIG. 3A-B show graphs of relative % MSTN mRNA levels in various types of cells.
Figure 3B:
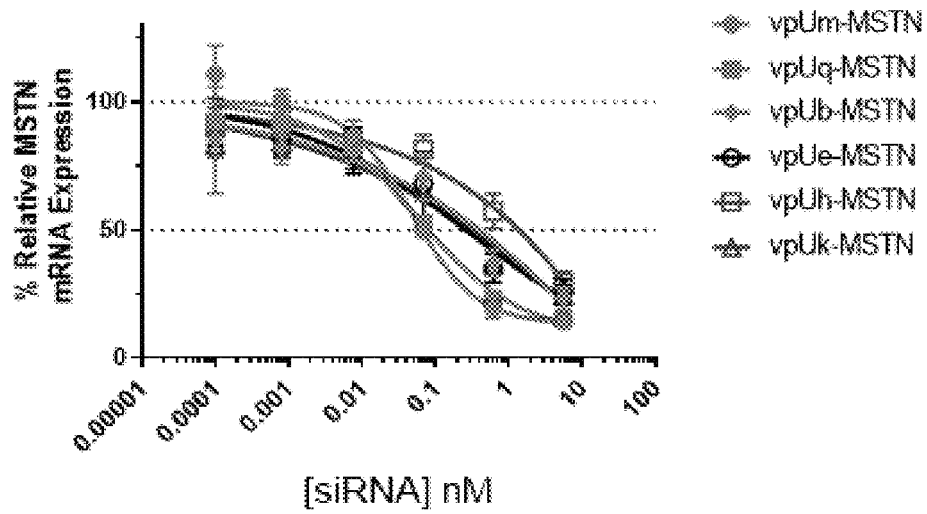
Figure 3C:
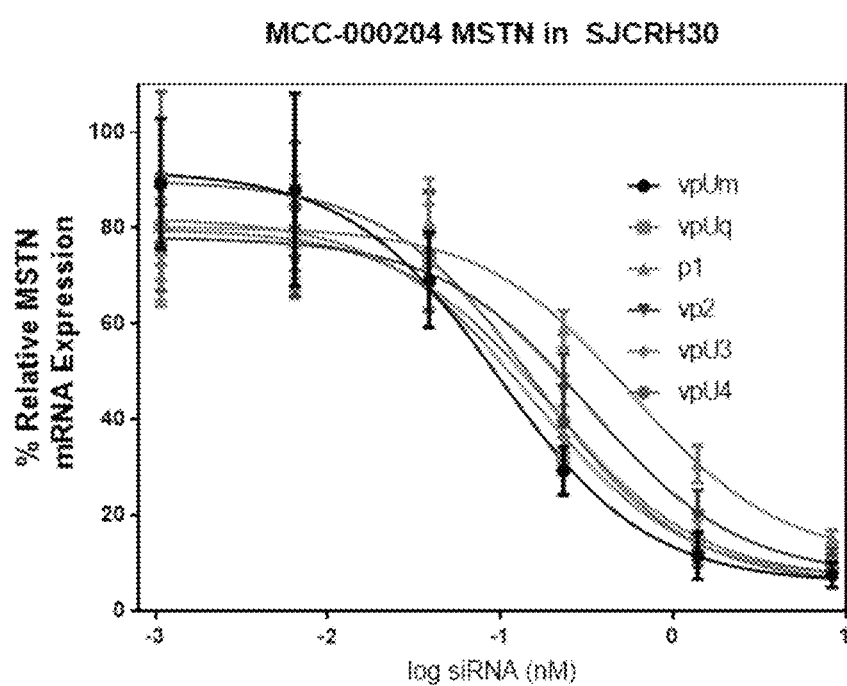
FIG. 3C shows a graph of relative % MSTN mRNA levels upon introduction of MSTN siRNA conjugate with different modified nucleotides to SJCRH30 cells.
Figure 3D:
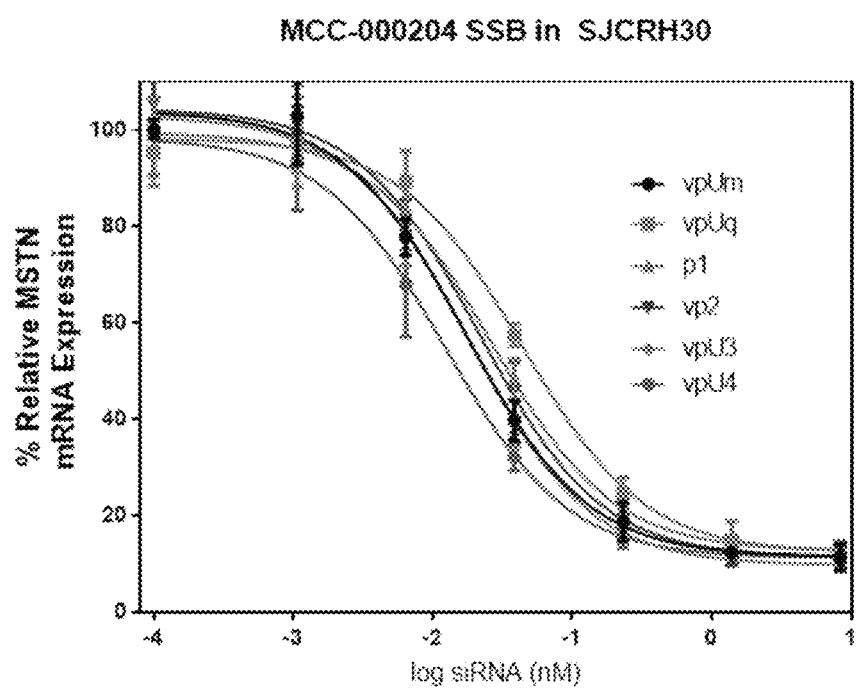
FIG. 3D shows a graph of relative % SSB mRNA levels upon introduction of SSB siRNA conjugate with different modified nucleotides to SJCRH30 cells.
Figure 4:
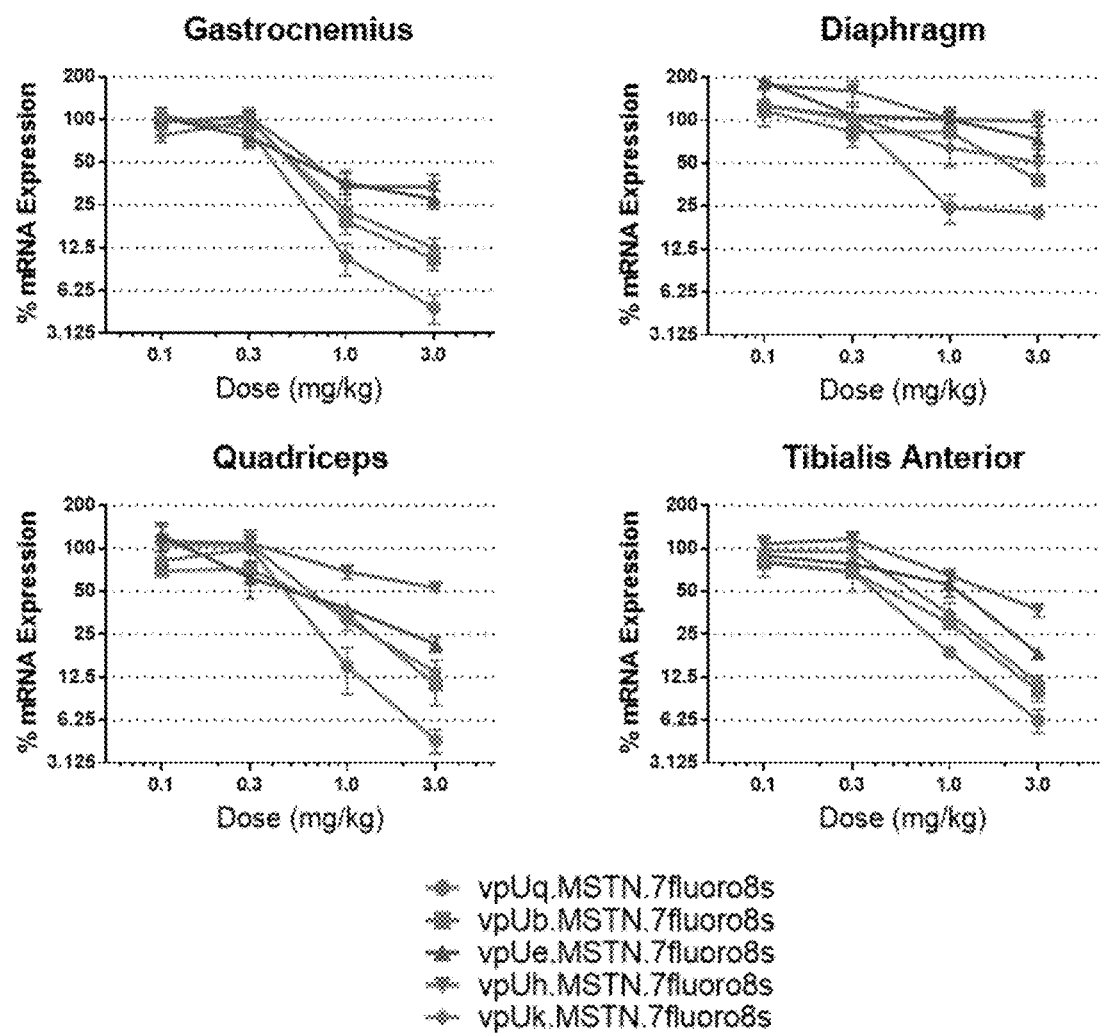
FIG. 4 shows in vivo MSTN mRNA downregulation in (upper left) gastroc, (lower left) quad, (upper right) diaphragm and (lower right) tibialis anterior muscle after IV administration of antibody siRNA conjugates at 0.1, 0.3, 1.0 and 3.0 mg/kg one week post administration, as described in molecular biology example 3.
Figure 5:
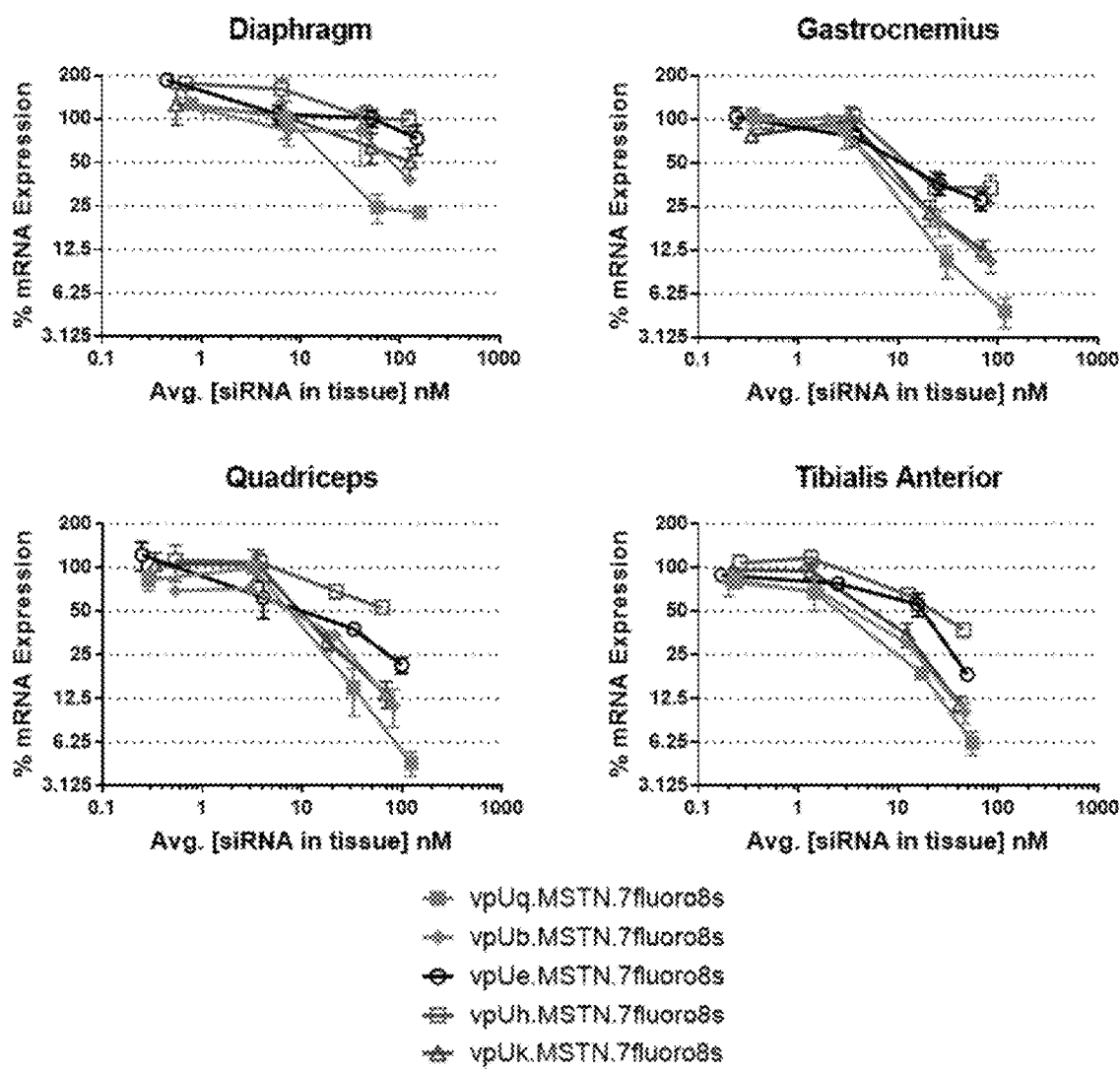
FIG. 5 shows plot of siRNA concentration vs in vivo MSTN mRNA downregulation in (upper left) gastroc, (lower left) quad, (upper right) diaphragm and (lower right) tibialis anterior muscle after IV administration of antibody siRNA conjugates one week post administration, as described in molecular biology example 3.
Figure 6:
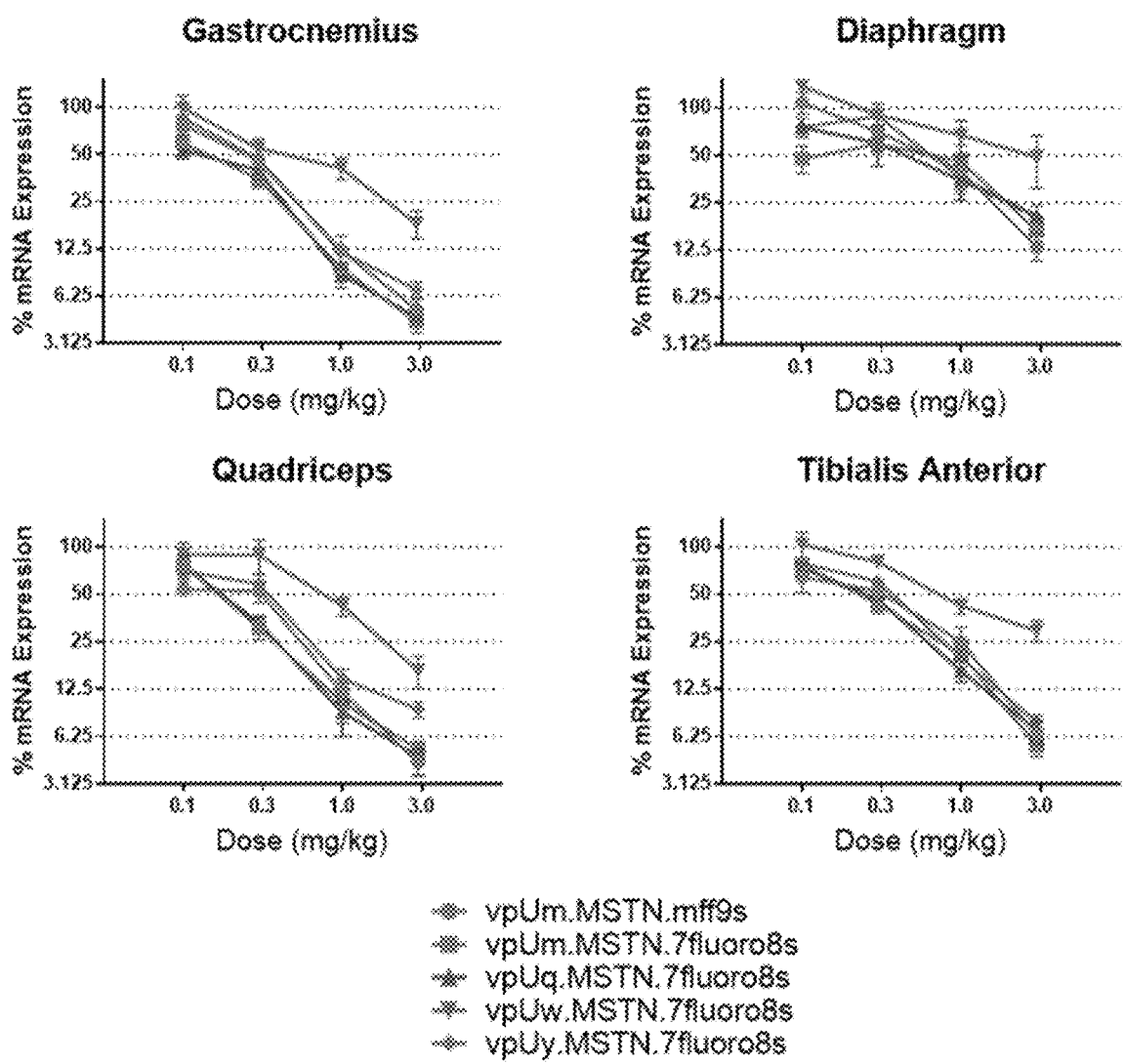
FIG. 6 shows in vivo MSTN mRNA downregulation in (upper left) gastroc, (lower left) quad, (upper right) diaphragm and (lower right) tibialis anterior muscle after IV administration of antibody siRNA conjugates one week post administration, as described in molecular biology example 3.
Figure 7:
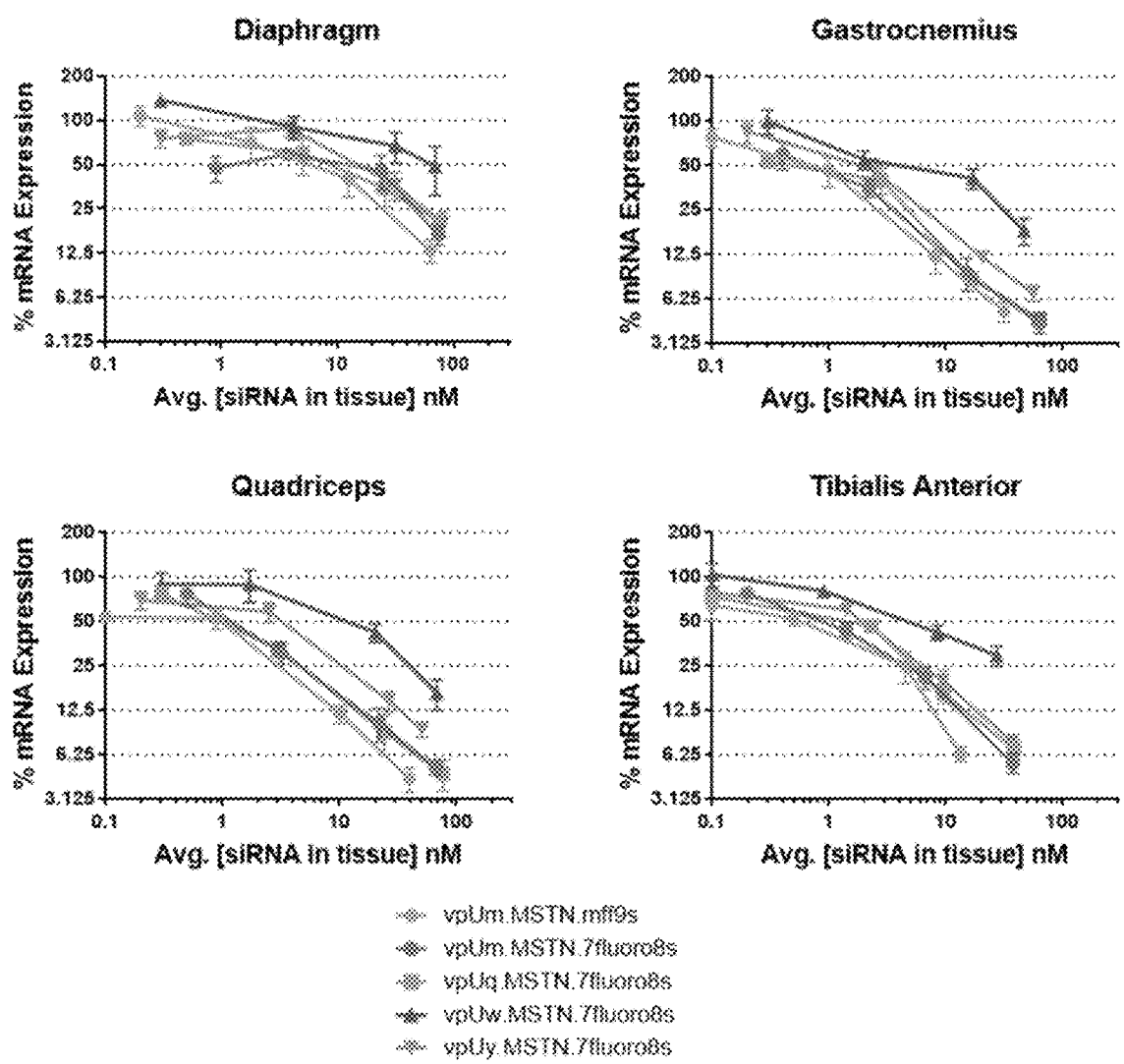
FIG. 7 shows in vivo MSTN mRNA downregulation in (upper left) gastroc, (lower left) quad. (upper right) diaphragm and (lower right) tibialis anterior muscle after IV administration of antibody siRNA conjugates one week post administration in another in vivo dose response studies, as described in molecular biology example 3.
Figure 8A:
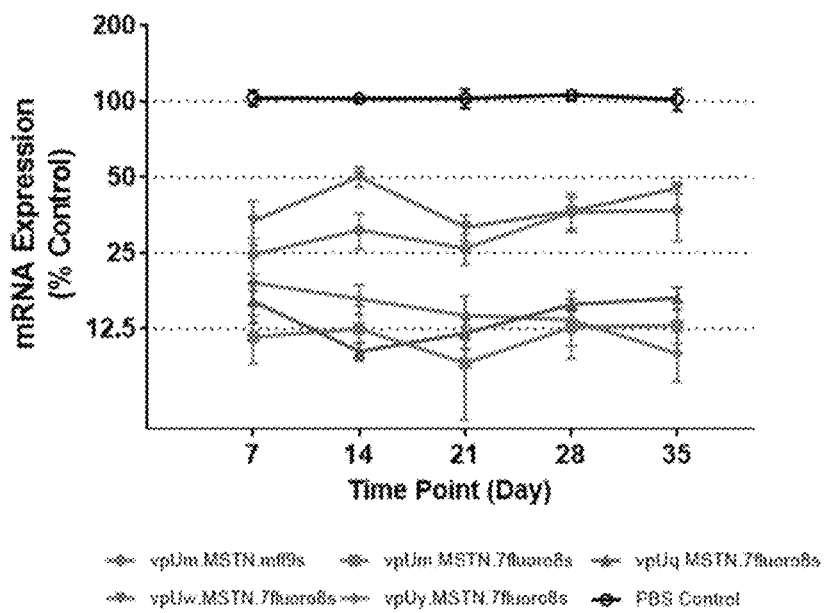
FIGS. 8A-D show graphs of in vivo MSTN mRNA downregulation and siRNA concentration in gastroc in two separate studies.
Figure 8B:
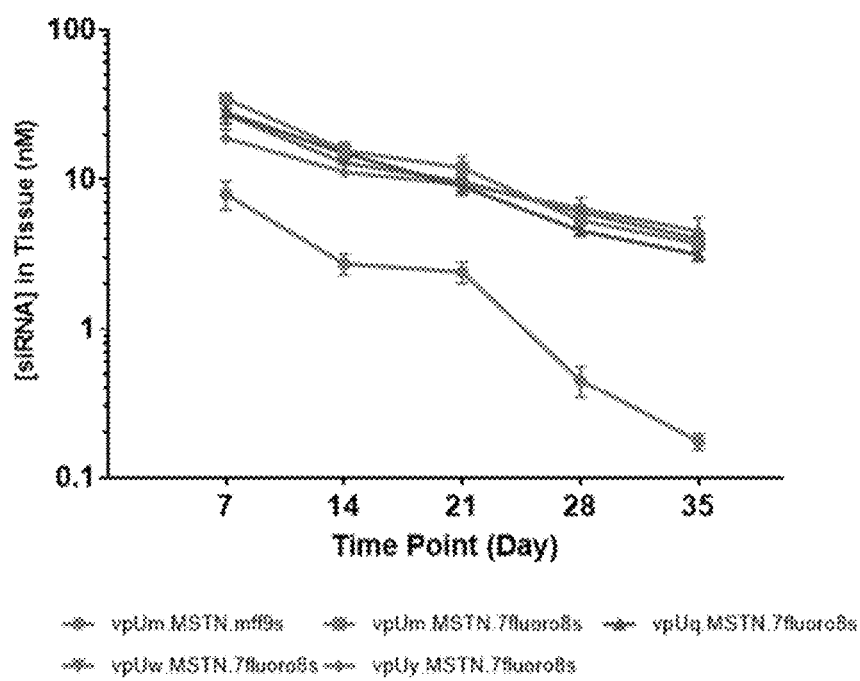
Figure 8C:
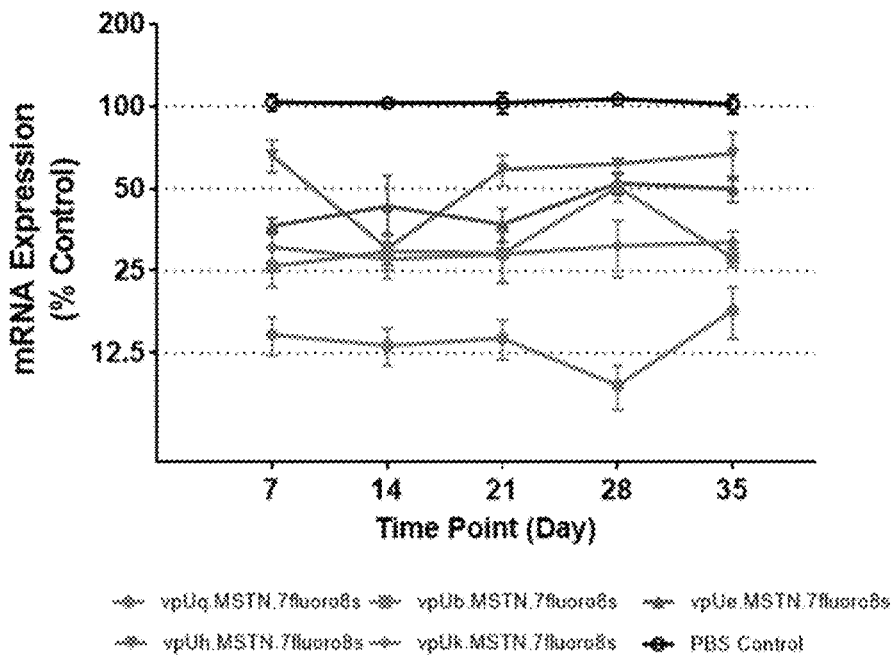
Figure 8D:
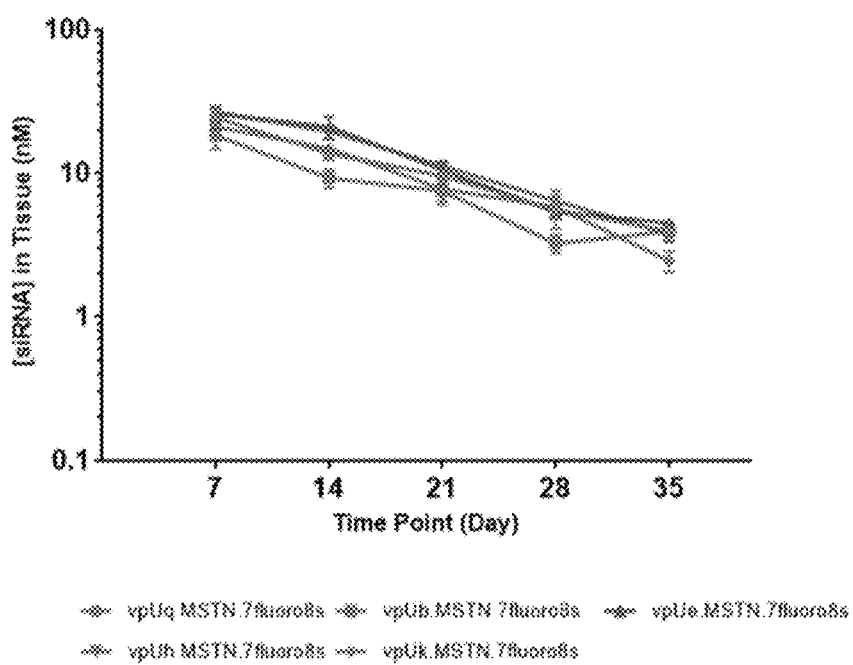
Figure 9:
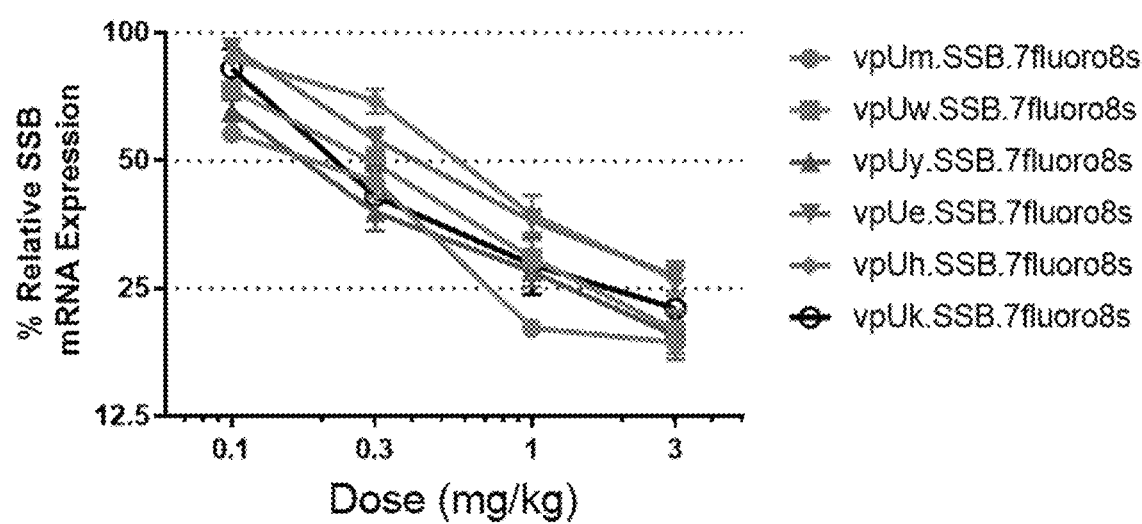
FIG. 9 shows a dose response graph of in vivo SSB mRNA downregulation in liver by different types of SSB-siRNAs as described in molecular biology example 3.

FIGS. 2A-C show the dose response curves demonstrating that novel phosphonate modified nucleotide structures on the 5' end of the guide strands of an SSB siRNA, after in vitro transfection of the duplex, can be loaded into RISC and mediate sequence specific down regulation of the target SSB gene.

Example 2. In Vitro Activity of siRNAs in SJCRH30 Cells and Apparently Healthy Human-Derived Myoblasts The activity of the siRNAs was evaluated in human rhabdomyosarcoma human cells (SJCRH30, ATCC CRL-2061) and in apparently healthy human-derived immortalized skeletal muscle myoblasts (MB) (obtained from Denis Furling, Institut de Myologie, France). SJCRH30 cells were grown in DMEM supplemented with 10% heat inactivated FBS (Gibco) and 10 mM HEPES and 1 mM sodium pyruvate. Human MB were grown in a complete skeletal muscle cell growth medium (PromoCell). Cells were plated 24 h prior to transfection in triplicate on 96-well tissue culture plates, with 8500 (SJCRH30) or 4000 (MB) cells per well, siRNAs were transfected into both cell types at 50 nM, 5.5556 nM, 0.6173 nM, 0.0686 nM, 0.0076 nM, 0.0008 nM, and 0.0001 nM final concentration. The siRNAs were formulated with commercially available transfection reagent Lipofectamine RNAiMAX (Life Technologies), according to the manufacturer's "forward transfection" protocol instructions. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with SSB-specific, MSTN-specific and PPIB-specific TaqMan gene expression probes (Thermo Fisher) using TaqMan® Fast Advanced Master Mix (Applied Biosystems). SSB and MSTN expression values were normalized within each sample to PPIB gene expression. The quantification of SSB and MSTN downregulation was performed using the standard $2^{-\Delta\Delta Ct}$ method. All experiments were performed in triplicate.

Table 3 shows the half maximal inhibitory concentrations of the analogs (compounds 1, 2, 3, and 4) and maximum knockdown achieved relative to the standard phosphonate modified nucleotide (vpUm.SSB.7f8s).

TABLE 3

| | IC50 (pM) | |
|---|---|---|
| Sample | DM1 Ctrl Myoblasts | SJCRH30 |
| vpUm.SSB.7f8s | 72.3 | 47.6 |
| 3, vpUb.SSB.7fEs | 146 | >200 |
| 2, vpUe.SSB.7fEs | 121.5 | 308 |
| 1, vpUh.SSB.7fEs | 451 | >500 |
| 4, vpUk.SSB.7fEs | 120 | >200 |

FIGS. 3A-D show the dose response curves, demonstrating that novel phosphonate modified nucleotide structures on the guide strands of an MSTN siRNA, after in vitro transfection of the duplex, can be loaded into RISC and mediate sequence specific down regulation of the target MSTN gene. Activity of the analogs (compounds 1, 2, 3, and 4) was comparable to the standard vinylphosphonate modified nucleotide (vpUm.SSB.7f8s). Table 4 shows the half maximal inhibitory concentrations of the compounds and maximum knockdown achieved relative to the standard phosphonate modified nucleotide (vpUm).

TABLE 4

| | IC50 (pM) | |
|---|---|---|
| Sample | MSTN | SSB |
| vpUm | 97.13 | 17.27 |
| vpUq | 150.9 | 43.49 |
| p1 | 570 | 26.11 |
| vp2 | 323.9 | 21.44 |
| vpU3 | 192.5 | 18.22 |
| vpU4 | 158.2 | 12.34 |

Example 3. In Vivo Activity of siRNAs in Wild Type CD-1 Mice

The conjugates were assessed for their ability to mediate MSTN mRNA downregulation in muscle tissues in an in vivo experiment (wild type CD-1 mice). Mice were dosed via intravenous (iv) injection with PBS vehicle control and the indicated ASCs and doses. After 168 hours, gastrocnemius (gastroc), quadricepts (quad), tibialis anterior (tib) and diaphragm tissues were harvested and snap-frozen in liquid nitrogen. mRNA knockdown in target tissue was determined using a comparative qPCR assay. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔΔCt).

In vivo efficacy of siRNAs with linear stable phosphates were tested using 8 different TfR1-mAb Conjugates compounds: TfR1.mAb-vpUm.MSTN, TfR1.mAb-vpUq.MSTN, TfR1.mAb-vpUw.MSTN, TfR1.mAb-vpUy.MSTN, TfR1.mAb-vpUb.MSTN, TfR1.mAb-vpUe.MSTN. TfR1.mAb-vpUh.MSTN, TfR1.mAb-vpUk.MSTN. These compounds were used for two in vivo dose response studies at 3, 1, 0.3, 0.1 mg/kg siRNA doses, respectively. Tissues were harvested at 168 hours after administration of TfR1-mAb Conjugates compounds, and MSTN mRNA knockdown were measured.

FIG. 4 and FIG. 6 show in vivo MSTN mRNA downregulations in (upper left) gastroc, (lower left) quad, (upper right) diaphragm and (lower right) tibialis anterior muscle after IV administration of antibody siRNA conjugates (TfR1.mAb-vpUq.MSTN, TfR1.mAb-vpUb.MSTN, TfR1.mAb-vpUe.MSTN, TfR1.mAb-vpUh.MSTN, TfR1.mAb-vpUk.MSTN) at 0.1, 0.3, 1.0 and 3.0 mg/kg one week post administration in two separate doe response studies. FIG. 5 shows plot of siRNA concentration vs in vivo MSTN mRNA downregulation in (upper left) gastroc, (lower left) quad, (upper right) diaphragm and (lower right) tibialis anterior muscle after single IV administration of antibody siRNA conjugates one week post administration.

FIG. 7 shows in vivo MSTN mRNA downregulations in (upper left) gastroc, (lower left) quad, (upper right) diaphragm and (lower right) tibialis anterior muscle after IV administration of various antibody-siRNA conjugates (TfR1.mAb-vpUm.MSTN, TfR1.mAb-vpUq.MSTN, TfR1.mAb-vpUw.MSTN, TfR1.mAb-vpUy.MSTN). FIGS. 8A-D show MSTN mRNA downregulations by various antibody-siRNA conjugates during 5 weeks after administration of the antibody-siRNA conjugates (FIGS. 8A and 8B: TfR1.mAb-vpUm.MSTN, TfR1.mAb-vpUq.MSTN, TfR1.mAb-vpUw.MSTN, TfR1.mAb-vpUy.MSTN; FIGS. 8C and 8D: TfR1.mAb-vpUq.MSTN, TfR1.mAb-vpUb.MSTN, TfR1.mAb-vpUe.MSTN, TfR1.mAb-vpUh.MSTN, TfR1.mAb-vpUk.MSTN), and their concentration during the period in the gastroc tissue.

In vivo efficacy of the antibody-siRNA conjugates were also determined in liver tissues using antibody-SSB siRNA with linear stable phosphates. FIG. 9 shows in vivo SSB mRNA downregulations after single IV administration of antibody-siRNA conjugates (ASGR1 Ab-vpUm.SSB, ASGR1 Ab-vpUw.SSB. ASGR1 Ab-vpUy.SSB, ASGR1 Ab-vpUe.SSB. ASGR1 Ab-vpUh.SSB, or ASGR1 Ab-vpUk.SSB) at 3, 1, 0.3, 0.1 mg/kg siRNA doses, respectively. Tissues were harvested at 168 hours after administration of ASGR1 SSB siRNA Conjugates compounds, and SSB mRNA knockdown were measured. As shown, all antibody-SSB siRNA with linear stable phosphates tested herein could reduce ~75% or more of SSB mRNA expression in 3 mg/kg dose.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCE LISTING

The patent contains a lengthy sequence listing. A copy of the sequence listing is available in electronic form from the USPTO web site (https://seqdata.uspto.gov/?pageRequest=docDetail&DocID=US12365704B2). An electronic copy of the sequence listing will also be available from the USPTO upon request and payment of the fee set forth in 37 CFR 1.19(b)(3).

What is claimed is:

1. An oligonucleotide comprising a compound of Formula (IIa) at one of the termini:

Formula (IIa)

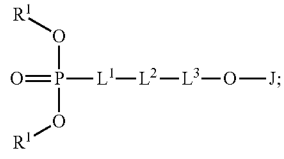

wherein;

each $R^1$ is independently substituted or unsubstituted $C_1$-$C_6$ alkyl, substituted or unsubstituted $C_1$-$C_6$ fluoroalkyl, or substituted or unsubstituted $C_1$-$C_6$ heteroalkyl;

$L^1$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;

$L^2$ is a bond, O, S, $NR^3$, substituted or unsubstituted $C_4$-$C_7$ cycloalkylene, substituted or unsubstituted $C_4$-$C_7$ heterocycloalkylene, substituted or unsubstituted $C_5$-$C_8$ arylene, or substituted or unsubstituted $C_4$-$C_8$ heteroarylene;

wherein $R^3$, when present, is selected from hydrogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted monocyclic carbocycle, and unsubstituted or substituted monocyclic heterocycle;

$L^3$ is a bond, substituted or unsubstituted $C_1$-$C_5$ alkylene, substituted or unsubstituted $C_2$-$C_5$ alkenylene, or substituted or unsubstituted $C_2$-$C_5$ alkynylene;

J is an internucleotide linking group linking to the adjacent nucleotide of the oligonucleotide; and wherein at least two of $L^1$, $L^2$ and $L^3$ are not a bond.

2. The oligonucleotide of claim 1, wherein the oligonucleotide is an RNA oligonucleotide.

3. The oligonucleotide of claim 2, further comprising at least one 2' modified nucleotide selected from 2'-O-methyl, 2'-O-methoxyethyl (2'-O-MOE), 2'-deoxy, 2-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA) modified nucleotide, locked nucleic acid (LNA) or ethylene nucleic acid (ENA).

4. The oligonucleotide of claim 2, further comprising at least one modified internucleotide linkage selected from a phosphorothioate linkage, a phosphorodithioate linkage, a methylphosphonate linkage, a phosphotriester linkage or an amide linkage.

5. The oligonucleotide of claim 2, wherein the compound of Formula (IIa) is located at the 5'-terminus of the oligonucleotide.

6. The oligonucleotide of claim 1, wherein the oligonucleotide is conjugated to a binding moiety.

7. The oligonucleotide of claim 6, wherein the compound of Formula (IIa) is located at the 5'-terminus of the oligonucleotide, and the binding moiety is conjugated to the 3'-terminus of the oligonucleotide.

8. The oligonucleotide of claim 6, wherein the binding moiety comprises a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), a camelid antibody or antigen binding fragment thereof, a peptide, an aptamer, or a small molecule.

9. The oligonucleotide of claim 1, comprising from about 15 to about 25 nucleotides.

10. The oligonucleotide of claim 2, wherein the oligonucleotide is conjugated with a polymer.

11. The oligonucleotide of claim 10, wherein the polymer is polyethylene glycol.

12. A method of treating a subject having a disease or a condition characterized with a defective protein expression or a protein overexpression, comprising administering to the subject an oligonucleotide of claim 2 to modulate expression of a gene encoding the protein, thereby treating the disease or condition characterized with the defective protein expression or characterized with the protein overexpression.

13. The method of claim 12, wherein the disease or the condition is a neuromuscular disease, a muscle dystrophy, a muscle atrophy, a muscle wasting, a genetic disease, cancer, a hereditary disease, or a cardiovascular disease.

* * * * *